US005334576A

United States Patent [19]
Doehner, Jr. et al.

[11] Patent Number: 5,334,576
[45] Date of Patent: Aug. 2, 1994

[54] 5 (AND/OR 6) SUBSTITUTED 2-(2-IMIDAZOLIN-2-YL)NICOTINIC ACIDS, ESTERS AND SALTS, USEFUL AS HERBICIDAL AGENTS AND NOVEL INTERMEDIATES FOR THE PREPARATION OF SAID NICOTINIC ACIDS, ESTERS AND SALTS

[75] Inventors: Robert F. Doehner, Jr., East Windsor; David W. Ladner, Hamilton Square; John M. Finn, Mercerville, all of N.J.

[73] Assignee: American Cyanamid Company, Wayne, N.J.

[21] Appl. No.: 855,259

[22] Filed: Mar. 23, 1992

Related U.S. Application Data

[63] Continuation of Ser. No. 397,699, Aug. 23, 1989, abandoned, which is a continuation of Ser. No. 139,996, Dec. 31, 1987, abandoned, which is a continuation-in-part of Ser. No. 889,999, Jul. 28, 1986, abandoned.

[51] Int. Cl.⁵ .................. A01N 43/40; C07D 401/04; C07D 413/04; C07F 9/58
[52] U.S. Cl. .................... 504/128; 504/250; 504/253; 546/22; 546/24; 546/261; 546/268; 546/278; 546/275

[58] Field of Search ............. 546/278, 22, 24, 268, 546/275, 261; 71/94; 504/250, 253, 128

[56] References Cited

U.S. PATENT DOCUMENTS

| 4,638,068 | 1/1987 | Los | 546/169 |
|---|---|---|---|
| 4,798,619 | 1/1989 | Los | 504/156 |

FOREIGN PATENT DOCUMENTS 62-174069A  7/1987  Japan ................. 546/278

OTHER PUBLICATIONS

Chemical Abstracts, vol. 96 (No. 23) 199,687-Q, Jun. 7, 1982.
Chem. Abstr., vol. 108, Abstract No. 94556j, 1988.

*Primary Examiner*—Alan L. Rotman
*Attorney, Agent, or Firm*—J. W. Hogan, Jr.

[57] ABSTRACT

There are provided novel 5(and/or 6)substituted 2-(2-imidazolin-2-yl) and 2-(2-imidazolidinyl)nicotinic acids, esters and salts, which are useful as herbicidal agents. There are also provided novel substituted pyrrolopyridine acetonitriles, pyrrolopyridine acetamides, imidazopyrrolopyridinediones and carbamoylnicotinic acid esters, that are useful as intermediates for the preparation of the above said herbicidal agents.

30 Claims, No Drawings

5 (AND/OR 6) SUBSTITUTED 2-(2-IMIDAZOLIN-2-YL)NICOTINIC ACIDS, ESTERS AND SALTS, USEFUL AS HERBICIDAL AGENTS AND NOVEL INTERMEDIATES FOR THE PREPARATION OF SAID NICOTINIC ACIDS, ESTERS AND SALTS

This application is a continuation of application Ser. No. 07/397,699, filed Aug. 23, 1989, abandoned, which is a continuation of application Ser. No. 139,996, filed Dec. 31, 1987, abandoned, which is a continuation-in-part of application Ser. No. 889,999, filed Jul. 28, 1986, abandoned.

This invention relates to novel, herbicidal, 5(and/or 6)substituted 2-(2-imidazolin-2-yl)nicotinic acids, esters and salts depicted by formula I and 5(and/or 6)substituted 2-(2-imidazolidinyl)nicotinic acids, esters and salts depicted by formula II,

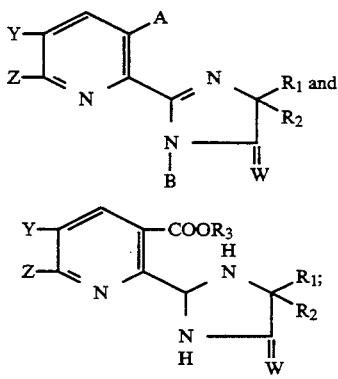

wherein $R_1$ is $C_1$–$C_4$ alkyl;

$R_2$ is $C_1$–$C_4$ alkyl or $C_3$–$C_6$ cycloalkyl; and when $R_1$ and $R_2$ are taken together with the carbon to which they are attached they may represent $C_3$–$C_6$ cycloalkyl optionally substituted with methyl;

A is $COOR_3$, $CONHR_6$, CHO, $CH_2OH$, $COCH_3$, $COC_6H_5$, CN, $CH_3$, CH=NOH, $CH_2COOH$, CONHOH, $CH_2CH_2COOH$, $CHR_8OH$,

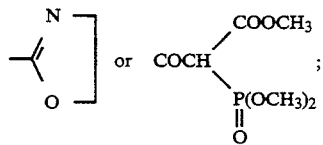

$R_3$ is hydrogen,

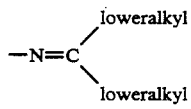

$C_1$–$C_{12}$ alkyl optionally substituted with one of the following groups: $C_1$–$C_3$ alkoxy, $C_1$–$C_3$ alkylthio, halogen, hydroxyl, $C_3$–$C_6$ cycloalkyl, benzyloxy, furyl, phenyl, halophenyl, loweralkylphenyl, loweralkoxyphenyl, nitrophenyl, carboxyl, loweralkoxycarbonyl, cyano or triloweralkylammonium halide;

$C_3$–$C_{12}$ alkenyl optionally substituted with one of the following groups: $C_1$–$C_3$ alkoxy, phenyl, halogen or loweralkoxycarbonyl or with two $C_1$–$C_3$ alkoxy groups or two halogen groups;

$C_3$–$C_6$ cycloalkyl optionally substituted with one or two $C_1$–$C_3$ alkyl groups;

$C_3$–$C_{16}$ alkynyl optionally substituted with one or two $C_1$–$C_3$ alkyl groups; or a cation;

$R_6$ is hydrogen, hydroxyl, $C_3$-alkenyl, $C_3$-alkynyl or $C_1$–$C_4$ alkyl optionally substituted with one hydroxyl or one chlorine group;

B is H, $COR_4$ or $SO_2R_5$, provided that when B is $COR_4$ or $SO_2R_5$; A is $COOR_3$ in which $R_3$ is other than H or a cation, $CH_3$ or CN; W is O; and Y and Z are not alkylamino, hydroxyl, or hydroxyloweralkyl;

$R_4$ is $C_1$–$C_{11}$ alkyl, chloromethyl or phenyl optionally substituted with one chloro, one nitro or one methoxy group;

$R_5$ is $CH_1$–$C_4$ alkyl or phenyl optionally substituted with one methyl group;

W is O or S;

$R_8$ is $C_1$–$C_4$ alkyl or phenyl;

Y and Z are each hydrogen, halogen, $C_1$–$C_6$ alkyl, $C_1$–$C_4$ hydroxyloweralkyl, $C_1$–$C_6$ alkoxy, $C_1$–$C_4$ alkylthio, formyl, phenoxy, $C_1$–$C_4$ haloalkyl, nitro, cyano, $C_1$–$C_4$ alkylamino, di-$C_1$–$C_4$ loweralkylamino, $C_1$–$C_4$ alkylsulfonyl, difluoromethoxy, trifluoromethoxy, 1,1,2,2,-tetrafluoroethoxy, phenyl optionally substituted with one $C_1$–$C_4$ alkyl, $C_1$–$C_4$ alkoxy or halogen;

$C_3$–$C_8$ straight or branched alkenyloxy optionally substituted with 1 to 3 halogens;

$C_3$–$C_8$ straight or branched alkylnyloxy optionally substituted with 1 to 3 halogens;

$C_2$–$C_6$ straight or branched alkenyl optionally substituted with phenyl, $C_1$–$C_4$ alkoxy or 1 to 3 halogens;

$C_2$–$C_6$ straight or branched alkynyl optionally substituted with phenyl, $C_1$–$C_4$ alkoxy, hydroxy, or 1 to 3 halogens;

$C_3$–$C_6$ cycloalkyl optionally substituted with methyl, halogen or $C_1$–$C_4$ alkoxy, and optionally interrupted by 1 oxygen, sulfur, amino, or $C_1$–$C_4$ alkylamino; oxiranyl optionally substituted by one or two $C_1$–$C_4$ alkyl;

$C_1$–$C_4$ alkylcarbonyl optionally substituted with $C_1$–$C_4$ alkoxy or 1 to 3 halogens;

$C_1$–$C_4$ alkylcarbonylamino optionally substituted on nitrogen with $C_1$–$C_2$ alkyl or $C_1$–$C_4$ alkoxy and on carbon with $C_1$–$C_4$ alkoxy or 1 to 3 halogens;

$C_1$–$C_4$ alkylcarbonyloxy optionally substituted with $C_1$–$C_4$ alkoxy or 1 to 3 halogens;

$C_1$–$C_4$ alkyl substituted with one or more of the following groups:

$C_1$–$C_4$ alkoxy optionally substituted with phenyl, thienyl, furyl, cyclopropyl, tetrahydrofuryl, $C_1$–$C_4$ alkoxy, $C_1$–$C_4$ dialkylamino, $C_1$–$C_4$ alkylamino, $C_1$–$C_4$ trialkylammonium, or 1 to 3 halogens; with the proviso that when the substituent on the $C_1$–$C_4$ alkoxy group is $C_1$–$C_4$ alkoxy, $C_1$–$C_4$ alkylamino, $C_1$–$C_4$ dialkylamino, or $C_1$–$C_4$ trialkylammonium, the respective heteroatoms are separated by at least 2 carbon atoms;

$C_1$–$C_4$ alkenyloxy optionally substituted with 1 to 3 halogens;

$C_1$–$C_4$ alkynyloxy optionally substituted with 1 to 3 halogens;

$C_3$–$C_6$ cycloalkoxy; phenyl thio;

$C_1$-$C_4$ alkylthio optionally substituted with phenyl or 1 to 3 halogens;

$C_1$-$C_4$ alkylsulfinyl optionally substituted with phenyl or 1 to 3 halogens;

$C_1$-$C_4$ alkylsulfonyl optionally substituted with phenyl or 1 to 3 halogens;

$C_1$-$C_4$ alkylamino optionally substituted on carbon by phenyl or 1 to 3 halogens;

$C_1$-$C_4$ dialkylamino;

$C_1$-$C_4$ trialkylammonium;

$C_1$-$C_4$ alkylcarbonyloxy; cyano;

phenylamino, optionally substituted in the ring by 1 to 3 halogens; $C_1$-$C_4$ lower alkyl, or $C_1$-$C_4$ lower alkoxy;

phenoxy, optionally substituted in the ring by 1 to 3 halogens; $C_1$-$C_4$ lower alkyl, or $C_1$-$C_4$ lower alkoxy; or $C_1$-$C_3$ alkyl;

2(or 3)-thienyl optionally substituted with halogen or $C_1$-$C_3$ alkyl;

N-methyl-2(or 3)-pyrrolyl; hydroxy; formyl;

amino optionally substituted with $C_1$-$C_4$ alkoxy, $C_1$-$C_4$ alkylsulfonyl, $C_1$-$C_2$ alkyl and $C_1$-$C_4$ alkoxy, $C_1$-$C_4$ alkylsulfonyl and $C_1$-$C_2$ alkyl, amino, $C_1$-$C_4$ monoalkylamino, or $C_1$-$C_4$ dialkly amino;

2(or 4)-pyridyloxy optionally substituted with $C_1$-$C_4$ alkyl, trifluoromethyl or 1 or 2 halogens;

$C_1$-$C_4$ mono or dialkylaminocarbonylamino, optionally substituted on the nitrogen attached to the ring with $C_1$-$C_2$ alkyl or $C_1$-$C_4$ alkoxy;

$C_1$-$C_4$ alkoxycarbonylamino, optionally substituted on nitrogen with $C_1$-$C_2$ alkyl or $C_1$-$C_4$ alkoxy;

$C_1$-$C_4$ mono or dialkylaminocarbonyloxy;

Provided that at least one Y and Z is:

$C_2$-$C_6$ straight or branched alkenyl optionally substituted with phenyl, $C_1$-$C_4$ alkoxy or 1 to 3 halogens;

$C_2$-$C_6$ straight or branched alkynyl optionally substituted with phenyl, $C_1$-$C_4$ alkoxy or 1 to 3 halogens;

$C_3$-$C_6$ cycloalkyl optionally substituted with methyl, halogen or $C_1$-$C_4$ alkoxy;

$C_1$-$C_4$ alkylcarbonyl optionally substituted with $C_1$-$C_4$ alkoxy or 1 to 3 halogens;

$C_1$-$C_4$ alkylcarbonylamino optionally substituted on nitrogen with $C_1$-$C_2$ alkyl or $C_1$-$C_4$ alkoxy and on carbon with $C_1$-$C_4$ alkoxy or 1 to 3 halogens;

$C_1$-$C_4$ alkylcarbonyloxy optionally substituted $C_1$-$C_4$ alkoxy or 1 to 3 halogens;

$C_1$-$C_4$ alkyl substituted with one or more of the following groups:

$C_1$-$C_4$ alkoxy optionally substituted with phenyl, thienyl, furyl, cyclopropyl, tetrahydrofuryl, $C_1$-$C_4$ alkoxy, $C_1$-$C_4$ dialkylamino, $C_1$-$C_4$ alkylamino, $C_1$-$C_4$ trialkylammonium, or 1 to 3 halogens; with the proviso that when the substituent on the $C_1$-$C_4$ alkoxy group is $C_1$-$C_4$ alkoxy, $C_1$-$C_4$ alkylamino, $C_1$-$C_4$ dialkylamino, or $C_1$-$C_4$ trialkylammonium, the respective heteroatoms are separated by at least 2 carbon atoms;

$C_1$-$C_4$ alkenyloxy optionally substituted with 1 to 3 halogens;

$C_1$-$C_4$ alkynyl oxy optionally substituted with 1 to 3 halogens;

$C_3$-$C_6$ cycloalkoxy; phenyl thio;

$C_1$-$C_4$ alkylthio optionally substituted with phenyl or 1 to 3 halogens;

$C_1$-$C_4$ alkylsulfinyl optionally substituted with phenyl or 1 to 3 halogens;

$C_1$-$C_4$ alkylsulfonyl optionally substituted with phenyl or 1 to 3 halogens;

$C_1$-$C_4$ alkylamino optionally substituted on carbon by phenyl or 1 to 3 hologens;

$C_1$-$C_4$ dialkylamino;

$C_1$-$C_4$ trialkylammonium;

$C_1$-$C_4$ alkylcarbonyloxy; cyano;

phenylamino, optionally substituted in the ring by 1 to 3 halogens; $C_1$-$C_4$ lower alkyl, or $C_1$-$C_4$ lower alkoxy;

phenoxy, optionally substituted in the ring by 1 to 3 halogens; $C_1$-$C_4$ lower alkyl, or $C_1$-$C_4$ lower alkoxy;

2(or 3)-furyl optionally substituted with halogen or $C_1$-$C_3$ alkyl;

2(or 3)-thienyl optionally substituted with halogen or $C_1$-$C_3$ alkyl;

N-methyl-2(or 3)-pyrrolyl; hydroxy; formyl;

amino optionally substituted with $C_1$-$C_4$ alkoxy, $C_1$-$C_4$ alkylsulfonyl, $C_1$-$C_2$ alkyl and $C_1$-$C_4$ alkoxy, $C_1$-$C_4$ alkylsulfonyl and $C_1$-$C_2$ alkyl, amino, $C_1$-$C_4$ monoalkylamino, or $C_1$-$C_4$ dialkyl amino;

2(or 4)-pyridyloxy optionally substituted by $C_1$-$C_4$ alkyl, trifluoromethyl or 1 to 2 halogens; and $C_1$-$C_4$ mono or dialkylaminocarbonylamino, optionally substituted on the nitrogen attached to the ring with $C_1$-$C_2$ alkyl or $C_1$-$C_4$ alkoxy;

$C_1$-$C_4$ alkoxycarbonylamino, optionally substituted on nitrogen with $C_1$-$C_2$ alkyl or $C_1$-$C_4$ alkoxy;

$C_1$-$C_4$ mono or dialkylaminocarbonyloxy;

Provided also that when Y is hydroxy, Z cannot be hydrogen; the N-oxides thereof when W is O provided that $R_3$ cannot be unsaturated alkyl and Y and Z cannot be alkylthioalkyl, alkylaminoalkyl, dialkylaminoalkyl, trialkylammoniumalkyl, amino, 2(or 4)-pyridyloxy, alkoxyamino or unsaturated alkyl; the optical isomers thereof when $R_1$ and $R_2$ are not the same; the tautomers thereof; and the acid addition salts thereof except when $R_3$ is a cation.

The present invention also relates to novel substituted pyrrolopyridine acetonitriles depicted by formula III, substituted pyrrolopyridine acetamides illustrated by formula IV, imidazopyrrolopyridinediones illustrated formulas V and VI, and carbamoyl nicotinic acids, esters and salts depicted by formula VII. These compounds have the structures illustrated below and are useful as intermediates for the preparation of the herbicidal nicotinic acids, esters and salts of formulas I and II.

Formula III, IV, V, VI and VII, compounds have the structures:

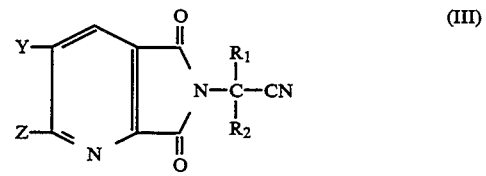

(III)

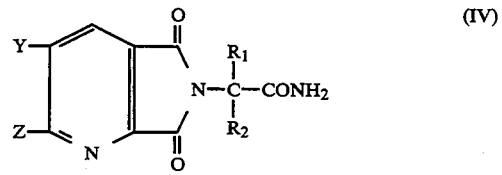

(IV)

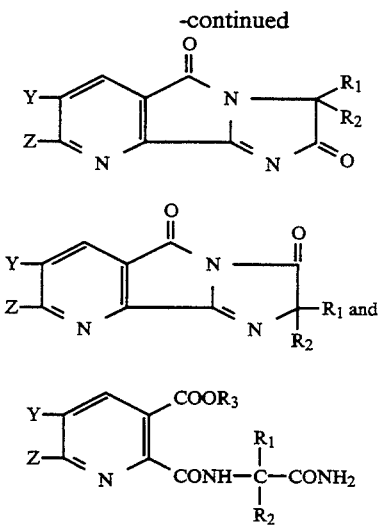

wherein $R_1$, $R_2$, $R_3$, Y and Z are as described above.

DESCRIPTION OF THE PREFERRED EMBODIMENTS

A preferred group of compounds of this invention are the 5(and/or 6)substituted 2-(2-imidazolin-2-yl)nicotinic acid, esters and salts represented by formula I above, wherein A, B, W, $R_1$ and $R_2$ are as described in said claim 1, and one of Y and Z represents hydrogen or methyl while the other of Y and Z represents $C_2$–$C_6$ straight or branches alkenyl optionally substituted with phenyl, $C_1$–$C_4$ alkoxy or 1 to 3 halogens;

$C_2$–$C_6$ straight or branched alkynyl optionally substituted with phenyl, $C_1$–$C_4$ alkoxy or 1 to 3 halogens;

$C_3$–$C_6$ cycloalkyl optionally substituted with methyl, halogen or $C_1$–$C_4$ alkoxy;

$C_1$–$C_4$ alkylcarbonyl optionally substituted with $C_1$–$C_4$ alkoxy or 1 to 3 halogens;

$C_1$–$C_4$ alkylcarbonylamino optionally substituted on nitrogen with $C_1$–$C_2$ alkyl or $C_1$–$C_4$ alkoxy and on carbon with $C_1$–$C_4$ alkoxy or 1 to 3 halogens;

$C_1$–$C_4$ alkylcarbonyloxy optionally substituted with $C_1$–$C_4$ alkoxy or 1 to 3 halogens;

$C_1$–$C_4$ alkyl substituted with $C_1$–$C_4$ alkoxy, $C_1$–$C_4$ alkylthio, $C_1$–$C_4$ alkylamino, $C_1$–$C_4$ dialkylamino, $C_1$–$C_4$ trialkylammonium or $C_1$–$C_4$ alkylcarbonyloxy;

2(or 3)-furyl optionally substituted with halogen or $C_1$–$C_3$ alkyl;

2(or 3)-thienyl optionally substituted with halogen or $C_1$–$C_3$ alkyl;

N-methyl-2(or 3)-pyrrolyl; hydroxy;

amino optionally substituted with $C_1$–$C_4$ alkoxy or $C_1$–$C_2$ alkyl and $C_1$–$C_4$ alkoxy;

2(or 4)-pyridyloxy optionally substituted with $C_1$–$C_4$ alkyl, trifluoromethyl or 1 or 2 halogens;

$C_1$–$C_4$ mono or dialkylaminocarbonylamino, optionally substituted on the nitrogen attached to the ring with $C_1$–$C_2$ alkyl or $C_1$–$C_4$ alkoxy;

$C_1$–$C_4$ alkoxycarbonylamino, optionally substituted on nitrogen with $C_1$–$C_2$ alkyl or $C_1$–$C_4$ alkoxy;

$C_1$–$C_4$ mono or dialkylaminocarbonyloxy; the N-oxides thereof when W is O, provided that $R_3$ cannot be unsaturated alkyl; the optical isomers thereof when $R_1$ and $R_2$ are not the same; the tautomers and geometric isomers thereof; and the acid addition salts thereof except when $R_3$ is a salt forming cation.

In this application the term cation means all cations, but preferably alkali metals, alkaline earth metals, ammonium, organic ammonium and inorganic metals such as copper, nickel, zinc, silver, lead, manganese, cobalt, iron and the like.

The term organic ammonium means a positively charged nitrogen atom joined to form one to four aliphatic groups, each containing from one to twenty carbon atoms and preferably one to six carbon atoms.

The compounds of the present invention are analogs of 2-(2-imidazolin-2-yl)pyridines of M. Los, described in the EPO application 81103638.3 published Dec. 16, 1981 and EPO patent specification publication number 0,041,623; published Jul. 28, 1985. However, the compounds of the present invention differ from those of M. Los in the 5(and/or 6) substitution of the pyridine ring. These differences may appear to be minimal but, in fact, are significant since they represent novel substitution of the imidazolinones and can provide new avenues to other herbicidally useful products or plant growth regulating agents.

Heretofore, 5(and/or 6) substitution on the pyridine ring was limited by the unavailability of methods for the preparation of substituted intermediates that would yield the 5(and/or 6) alkenyl, alkynyl, cycloalkyl, alkylcarbonyl, alkylcarbonylamino, 2(or 3)-furyl, 2(or 3)'-thienyl, 2(or 4) pyridyloxy or the like, formula I-VII compounds of the present invention.

It is therefore an object of the present invention to provide novel 5(and/or 6)substituted 2-(2-imidazolin-2-yl)nicotinic acids, esters and salts and novel 5(and/or 6)substituted intermediates therefore.

In the following descriptions for the preparation of the formula I 5(and/or 6)substituted 2-(2-imidazolin-2-yl)nicotinic acids, esters and salts, the imidazolinyl function, has the following structure:

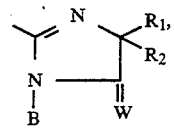

wherein $R_1$, $R_2$, B and W are as described above; however, to avoid the repeated use of this structure in the specification, a specific imidazolinyl function is used as representative of the above structure. The specific imidazolinyl function is (4-isopropyl-4-methyl-5-oxo-2-imidazolin-2-yl), and is used in the specification simply as a convenience in describing the reactions in which the above illustrated function can be involved. It is not meant to limit the invention or the reaction described. In practice, the structure can be substituted for the above-said terminology and the substituents identified as $R_1$, $R_2$, B and W, can be any of those selected from definitions for $R_1$, $R_2$, B and W mentioned above.

In accordance with this invention, 6-(4-isopropyl-4-methyl-5-oxo-2-imidazolin-2-yl)pyridine-3-carboxaldehyde is prepared by oxidation of 2-(5-hydroxymethyl-2-pyridyl)-4-isopropyl-4-methyl-2-imidazolin-5-one with manganese dioxide at an elevated temperature in the presence of an inert organic solvent such as a chlorinated hydrocarbon.

The thus prepared carboxaldehyde can then be converted to the desired 2-(5-alkenyl-2-pyridyl)-4-isopropyl-4-methyl-5-oxo-2-imidazolin-4-one by reaction of said aldehyde with the appropriate alkyl triphenylphosphonium halide in the presence of an alkali metal hydride, mineral oil and dimethylsulfoxide. Lithiation of this 5-alkenyl derivative, using methyl lithium and carbon dioxide in the presence of tetrahydrofuran, affords the corresponding, herbicidally active, 2-(4-isopropyl-4-methyl-5-oxo-2-imidazolin-2-yl)-5-alkenylnicotinic acid.

Esterification of the thus prepared nicotinic acid can then be achieved by reaction of said acid with ethereal diazoalkane, preferably in the presence of an inert organic solvent such as chlorinated hydrocarbon.

Preparation of the 5(and/or 6)substituted nicotinic acids wherein the 5(and/or 6)substitution is alkenyl, alkylcarbonyl, 2(or 3)-furyl or 2(or 3)-thienyl, can be accomplished from the appropriate 5(and/or 6)substituted-2,3-dicarboxylate.

In this method the appropriate substituted 5(and/or 6)pyridine-2,3-dicarboxylate is converted to the corresponding acid by heating with a strong base, such as an alkali metal hydroxide, and then acidifying the reaction mixture with a strong mineral acid. Heating of the thus formed acid with acetic anhydride, preferably in the presence of pyridine and 1,2-dimethoxyethane, yields the 5(and/or 6)substituted pyridine-2,3-dicarboxylic anhydride. The 5(and/or 6)substituted pyridine-2,3-dicarboxylic anhydride is then reacted with an aminocarboxamide to yield an isomeric mixture of the 5(and/or 6)substituted carbamoylnicotinic acid and the 5(and/or 6)substituted carbamoylpicolinic acid.

This reaction is carried out using approximately equimolar amounts of the anhydride and the carboxamide, in the presence of an inert organic solvent such as a chlorinated hydrocarbon or a low-boiling ether such as THF, diethyl ether, or dimethoxyethane. When the reaction is essentially complete, the product mixture is heated with base to give a mixture of the 2-(4-isopropyl-4-methyl-5-oxo-2-imidazolin-2-yl) 5-(and/or 6)substituted nicotinic acid and the 3-(4-isopropyl-4-methyl-5-oxo-2-imidazolin-2-yl)-5-(and/or 6)substituted picolinic acid. Conversion of this acid mixture to the corresponding esters can then be achieved by reaction of said mixture with acetic anhydride, preferably in the presence of an inert organic solvent such as toluene, xylene, benzene or the like. The reaction provides a mixture of the tricyclic diones of formulas V and VI which can be ring opened with an alkali metal alkoxide to yield a mixture of the 2-(4-isopropyl-4-methyl-5-oxo-2-imidazolin-2-yl) 5-(and/or 6)substituted nicotinate and the 3-(4-isopropyl-4-methyl-5-oxo-2-imidazolin-2-yl) 5-(and/or 6)substituted picolinate.

Conversion of the alkyl 2-(4-isopropyl-4-methyl-5-oxo-2-imidazolin-2-yl) 5-(and/or 6)alkenyl nicotinates or the corresponding 5-(and/or 6)alkylthioalkyl or alkoxyalkylnicotinates to the corresponding acid can be achieved by reaction of the ester with alcoholic alkali metal hydroxide at an elevated temperature. After heating the reaction mixture is cooled and acidified with a strong mineral acid. The reaction is concentrated and then partitioned between a chlorinated hydrocarbon solvent and water.

Preparation of formula I, 5(and/or 6)haloalkyl 2-(2-imidazolin-2-yl)nicotinates can be achieved by reacting an alkyl 2-(4-isopropyl-4-methyl-5-oxo-2-imidazolin-2-yl)-5-alkylnicotinate with an N-halosuccinimide and benzoyl peroxide in the presence of an inert organic solvent such a chlorinated hydrocarbon. This reaction is generally conducted at an elevated temperature, preferably under a blanket of inert gas. The reaction yields the alkyl 2-(4-isopropyl-4-methyl-5-oxo-2-imidazolin-2-yl)-5-(and/or 6)-(1-haloalkyl)nicotinate. If this reaction is conducted using an imidazolinyl function in which B is $COR_4$ as described above, the $COR_4$ function is retained during the reaction but can be removed from the product ester by reaction thereof with aqueous alcohol and a strong mineral acid. These reactions are exemplified by examples 9 and 10 described in detail below. The thus obtained alkyl 2-(4-isopropyl-4-methyl-5-oxo-2-imidazolin-2-yl)-5-(and/or 6)-(1-haloalkyl)nicotinate can then be used as the starting material for the preparation of the corresponding formula I 5(and/or 6)alkyl substituted with alkylcarbonyloxy 2-(2-imidazolin-2-yl)nicotinate. The reaction involves the treatment of the 5(and/or 6)-1-(haloalkyl)nicotinate referred to above, with an organic acid and an alkali metal salt of said organic acid.

Treatment of the thus prepared formula I 2-(2-imidazolin-2-yl)nicotinate, having a 5(and/or 6)alkyl substituent substituted with an alkylcarbonyloxy function, with an alkali metal alkoxide in a lower aliphatic alcohol provides the corresponding 5(and/or 6)hydroxyloweralkyl function on the pyridine ring of the 2-(2-imidazolin-2-yl)nicotinate.

Treatment of this 5-(and/or 6)hydroxy loweralkyl 2-(2-imidazolin-2-yl)nicotinate with pyridinium dichromate and pyridinium trifluoroacetate in the presence of an inert organic solvent such as a chlorinated hydrocarbon, then yields the corresponding 5(and/or 6)alkylcarbonyl 2-(2-imidazolin-2-yl)nicotinate.

To obtain the formula I, 5(and/or 6)alkylthioalkyl substituted 2-(2-imidazolin-2-yl)nicotinates of this invention, a formula I 5(and/or 6)haloalkyl 2-(2-imidazolin-2-yl)nicotinate is dissolved in absolute methanol, treated with a 50% oil dispersion of alkali metal hydride and then with an alkyl mercaptan. These additions are generally made while maintaining the temperature of the mixture below about $-5°$ C. Thereafter, the mixture is acidified with acetic acid to pH 4 and then concentrated in vacuo. The residue can be dissolved in methylene chloride, washed with aqueous sodium bicarbonate, reconcentrated in vacuo and the product recovered.

Additional methods for the preparation of the compounds of this invention are described in the examples below.

Among the compounds of this invention that can be prepared by the methods described above and/or exemplified below are those having the following structure:

| Y | Z |
|---|---|
| vinyl | hydrogen |
| 1-propenyl | hydrogen |
| allyl | hydrogen |
| allyl | allyl |
| 3-methoxy propenyl | hydrogen |

-continued

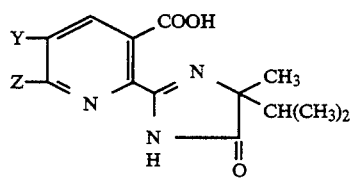

| Y | Z |
|---|---|
| 3-chloropropenyl | methoxy |
| 2-trichloromethylvinyl | hydrogen |
| 1-chlorovinyl | dimethylamino |
| 2-chlorovinyl | hydrogen |
| isopropenyl | hydrogen |
| 2-phenylvinyl (cis) | hydrogen |
| 2-phenylvinyl (trans) | hydrogen |
| ethynyl | hydrogen |
| 1-propynyl | hydrogen |
| 2-propynyl | ethoxy |
| 3-chloro-1-propynyl | hydrogen |
| 3-methoxy-1-propynyl | hydrogen |
| 3-phenyl-1-propynyl | hydrogen |
| 2-trichloromethyl-1-ethynyl | cyano |
| 2-chloro-1-ethynyl | hydrogen |
| cyclopropyl | p-tolyl |
| cyclopropyl | hydrogen |
| cyclopropyl | methoxy |
| cyclobutyl | hydrogen |
| cyclobutyl | phenyl |
| cyclopentyl | hydrogen |
| cyclohexyl | hydrogen |
| 2,2-dimethyl-1-cyclopropyl | hydrogen |
| 2-methyl-1-cyclohexyl | hydrogen |
| 2-chloro-1-cyclohexyl | hydrogen |
| 2-chloro-1-cyclopropyl | hydrogen |
| 2-methoxy-1-cyclohexyl | hydrogen |
| 2-methoxy-1-cyclopropyl | hydrogen |
| acetyl | hydrogen |
| propionyl | hydrogen |
| butyryl | hydrogen |
| methoxyacetyl | hydrogen |
| butoxyacetyl | hydrogen |
| chloroacetyl | hydrogen |
| dichloroacetyl | hydrogen |
| trichloroacetyl | hydrogen |
| 2-chloropropionyl | hydrogen |
| 3-chloropropionyl | hydrogen |
| acetamido | hydrogen |
| propionamido | hydrogen |
| butyramido | hydrogen |
| chloroacetamido | hydrogen |
| dichloroacetamido | hydrogen |
| methoxyacetamido | hydrogen |
| 2-chloropropionamido | hydrogen |
| 3-chloropropionamido | hydrogen |
| N-methylacetamido | hydrogen |
| N-ethylacetamido | hydrogen |
| N-methoxyacetamido | hydrogen |
| N-butoxyacetamido | hydrogen |
| N-methylpropionamido | hydrogen |
| N-methoxypropionamido | hydrogen |
| N-methylchloroacetamido | hydrogen |
| N-methoxychloroacetamido | hydrogen |
| N-methyldichloroacetamido | hydrogen |
| N-methoxydichloroacetamido | hydrogen |
| acetoxy | hydrogen |
| acetoxy | acetamido |
| propionyloxy | hydrogen |
| butyryloxy | hydrogen |
| methoxyacetoxy | hydrogen |
| chloroacetoxy | hydrogen |
| dichloroacetoxy | hydrogen |
| trichloroacetoxy | hydrogen |
| 2-chloropropionyloxy | hydrogen |
| 3-chloropropionyloxy | hydrogen |
| 2,2-dichloropropionyloxy | hydrogen |
| methoxymethyl | hydrogen |
| methoxymethyl | methoxymethyl |
| ethoxymethyl | hydrogen |
| n-propoxymethyl | hydrogen |
| i-propoxymethyl | hydrogen |

-continued

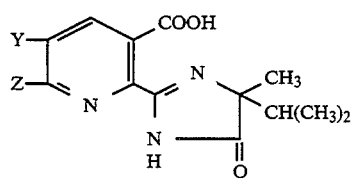

| Y | Z |
|---|---|
| n-butoxymethyl | hydrogen |
| i-butoxymethyl | hydrogen |
| sec-butoxymethyl | hydrogen |
| tert-butoxymethyl | hydrogen |
| 2-methoxyethyl | 3-thienyl |
| 2-methoxyethyl | hydrogen |
| 2-ethoxyethyl | hydrogen |
| 2-methoxypropyl | hydrogen |
| 3-methoxypropyl | hydrogen |
| 2-methoxy-2-methylethyl | hydrogen |
| methylthiomethyl | hydrogen |
| methylthiomethyl | 2-furyl |
| ethylthiomethyl | hydrogen |
| propylthiomethyl | hydrogen |
| butylthiomethyl | hydrogen |
| 1-methylthioethyl | hydrogen |
| 2-methylthioethyl | hydrogen |
| 1-methylthiopropyl | hydrogen |
| 2-methyl-2-methylthioethyl | hydrogen |
| methylaminomethyl | hydrogen |
| methylaminomethyl | p-chlorophenyl |
| ethylaminomethyl | hydrogen |
| n-propylaminomethyl | hydrogen |
| i-propylaminomethyl | hydrogen |
| n-butylaminomethyl | hydrogen |
| i-butylaminomethyl | hydrogen |
| sec-butylaminomethyl | hydrogen |
| tert-butylaminomethyl | hydrogen |
| 2-methylaminoethyl | hydrogen |
| 2-methylaminopropyl | hydrogen |
| 2-methylaminobutyl | hydrogen |
| 2-methyl-2-methylaminoethyl | hydrogen |
| 3-methylaminopropyl | hydrogen |
| dimethylaminomethyl | hydrogen |
| diethylaminomethyl | hydrogen |
| methyl(ethyl)aminomethyl | hydrogen |
| dipropylaminomethyl | hydrogen |
| methyl(propyl)aminomethyl | hydrogen |
| ethyl(propyl)aminomethyl | hydrogen |
| 1-dimethylaminoethyl | hydrogen |
| 2-dimethylaminoethyl | hydrogen |
| 1-diethylaminoethyl | hydrogen |
| 2-diethylaminoethyl | hydrogen |
| 3-dimethylaminopropyl | hydrogen |
| (trimethylammonium)methyl | hydrogen |
| (triethylammonium)methyl | hydrogen |
| 1-(trimethylammonium)ethyl | hydrogen |
| 2-(trimethylammonium)ethyl | hydrogen |
| 3-(trimethylammonium)propyl | hydrogen |
| acetoxymethyl | hydrogen |
| propionyloxymethyl | hydrogen |
| butyroyloxymethyl | hydrogen |
| 1-acetoxyethyl | hydrogen |
| 2-acetoxyethyl | hydrogen |
| 3-acetoxypropyl | hydrogen |
| 2-acetoxy-2-methylethyl | hydrogen |
| 2-furyl | hydrogen |
| 3-furyl | hydrogen |
| 3-chloro-2-furyl | hydrogen |
| 4-chloro-2-furyl | hydrogen |
| 5-chloro-2-furyl | hydrogen |
| 2-chloro-3-furyl | hydrogen |
| 4-chloro-3-furyl | hydrogen |
| 5-chloro-3-furyl | hydrogen |
| 3-methyl-2-furyl | hydrogen |
| 5-methyl-2-furyl | hydrogen |
| 2-methyl-3-furyl | hydrogen |
| 5-methyl-3-furyl | hydrogen |
| 2-thienyl | hydrogen |
| 3-thienyl | hydrogen |
| 3-chloro-2-thienyl | hydrogen |
| 4-chloro-2-thienyl | hydrogen |

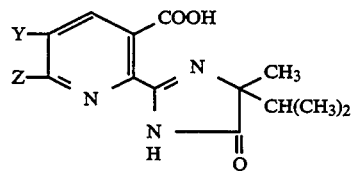

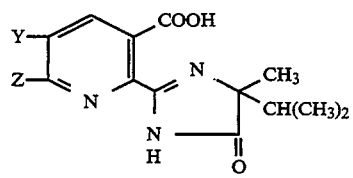

| Y | Z |
|---|---|
| 5-chloro-2-thienyl | hydrogen |
| 2-chloro-3-thienyl | hydrogen |
| 4-chloro-3-thienyl | hydrogen |
| 5-chloro-3-thienyl | hydrogen |
| 3-methyl-2-thienyl | hydrogen |
| 5-methyl-2-thienyl | hydrogen |
| 2-methyl-3-thienyl | hydrogen |
| 5-methyl-3-thienyl | hydrogen |
| 5-bromo-2-furyl | hydrogen |
| 5-bromo-2-thienyl | hydrogen |
| N-methyl-2-pyrrolyl | hydrogen |
| N-methyl-3-pyrrolyl | hydrogen |
| amino | hydrogen |
| methoxyamino | hydrogen |
| ethoxyamino | hydrogen |
| n-propyloxyamino | hydrogen |
| i-propyloxyamino | hydrogen |
| n-butoxyamino | hydrogen |
| i-butoxyamino | hydrogen |
| sec-butoxyamino | hydrogen |
| tert-butoxyamino | hydrogen |
| methyl(methoxy)amino | hydrogen |
| ethyl(methoxy)amino | hydrogen |
| methyl(ethoxy)amino | hydrogen |
| ethyl(ethoxy)amino | hydrogen |
| 2-pyridyloxy | hydrogen |
| 4-pyridyloxy | hydrogen |
| 3-fluoro-2-pyridyloxy | hydrogen |
| 3-chloro-2-pyridyloxy | hydrogen |
| 3-methyl-2-pyridyloxy | hydrogen |
| 3,5-dichloro-2-pyridyloxy | hydrogen |
| 3,5-difluoro-2-pyridyloxy | hydrogen |
| 5-trifluoromethyl-2-pyridyloxy | hydrogen |
| 3-fluoro-5-trifluoromethyl-2-pyridyloxy | hydrogen |
| hydrogen | vinyl |
| hydrogen | 1-propenyl |
| hydrogen | allyl |
| hydrogen | 3-methoxypropenyl |
| hydrogen | 3-chloropropenyl |
| hydrogen | 2-trichloromethyl vinyl |
| hydrogen | 1-chlorovinyl |
| hydrogen | 2-chlorovinyl |
| hydrogen | isopropenyl |
| hydrogen | 2-phenylvinyl(cis) |
| hydrogen | 2-phenylvinyl(trans) |
| hydrogen | ethynyl |
| hydrogen | 1-propynyl |
| hydrogen | 2-propynyl |
| hydrogen | 3-chloro-1-propynyl |
| hydrogen | 3-methoxy-1-propynyl |
| hydrogen | 2-trichloromethylethynyl |
| hydrogen | 2-chloro-1-ethynyl |
| trifluoromethoxy | 1-chlorovinyl |
| methylthio | 2-chlorovinyl |
| methylsulfonyl | ethynyl |
| 2-chlorovinyl | 2-chlorovinyl |
| hydrogen | cyclopropyl |
| phenyl | cyclopropyl |
| hydrogen | cyclobutyl |
| hydrogen | cyclopentyl |
| hydrogen | cyclohexyl |
| hydrogen | 2,2-dimethyl-1-cyclopropyl |
| hydrogen | 2-methyl-1-cyclohexyl |
| hydrogen | 2-methoxy-1-cyclopropyl |
| hydrogen | acetyl |
| dimethylamino | acetyl |
| hydrogen | propionyl |
| hydrogen | butyryl |
| hydrogen | methoxyacetyl |
| hydrogen | butoxyacetyl |
| 2-thienyl | chloroacetyl |
| hydrogen | chloroacetyl |
| hydrogen | dichloroacetyl |
| hydrogen | trichloroacetyl |
| hydrogen | 2-chloropropionyl |
| hydrogen | 3-chloropropionyl |
| hydrogen | acetamido |
| hydrogen | propionamido |
| hydrogen | butyramido |
| hydrogen | chloroacetamido |
| hydrogen | dichloroacetamido |
| hydrogen | trichloroacetamido |
| hydrogen | methoxyacetamido |
| hydrogen | 2-chloropropionamido |
| hydrogen | 3-chloropropionamido |
| hydrogen | N-methylacetamido |
| hydrogen | N-ethylacetamido |
| hydrogen | N-methoxyacetamido |
| hydrogen | N-butoxyacetamido |
| hydrogen | N-methylpropionamido |
| hydrogen | N-methoxypropionamido |
| hydrogen | N-methylchloroacetamido |
| hydrogen | N-methoxychloroacetamido |
| hydrogen | N-methyldichloroacetamido |
| hydrogen | N-methoxydichloroacetamido |
| hydrogen | acetoxy |
| hydrogen | propionyloxy |
| hydrogen | butyroyloxy |
| hydrogen | methoxyacetoxy |
| hydrogen | chloroacetoxy |
| hydrogen | dichloroacetoxy |
| hydrogen | trichloroacetoxy |
| hydrogen | 2-chloropropionyloxy |
| hydrogen | 3-chloropropionyloxy |
| hydrogen | 2,2-dichloropropionyloxy |
| hydrogen | methoxymethyl |
| hydrogen | ethoxymethyl |
| hydrogen | n-propoxymethyl |
| hydrogen | i-propoxymethyl |
| hydrogen | n-butoxymethyl |
| hydrogen | i-butoxymethyl |
| hydrogen | sec-butoxymethyl |
| hydrogen | tert-butoxymethyl |
| hydrogen | 2-methoxyethyl |
| hydrogen | 2-ethoxyethyl |
| hydrogen | 2-methoxypropyl |
| hydrogen | 3-methoxypropyl |
| hydrogen | 2-methoxy-2-methylethyl |
| hydrogen | methylthiomethyl |
| hydrogen | ethylthiomethyl |
| hydrogen | propylthiomethyl |
| hydrogen | butylthiomethyl |
| hydrogen | 1-methylthioethyl |
| hydrogen | 2-methylthioethyl |
| hydrogen | 1-methylthiopropyl |
| hydrogen | 2-methyl-2-methylthioethyl |
| hydrogen | methylaminomethyl |
| hydrogen | ethylaminomethyl |
| hydrogen | n-propylaminomethyl |
| hydrogen | i-propylaminomethyl |
| hydrogen | n-butylaminomethyl |
| hydrogen | i-butylaminomethyl |
| hydrogen | sec-butylaminomethyl |
| hydrogen | tert-butylaminomethyl |
| hydrogen | 2-methylaminoethyl |
| hydrogen | 2-methylaminopropyl |
| hydrogen | 2-methylaminobutyl |
| hydrogen | 2-methyl-2-methylaminoethyl |
| hydrogen | 3-methylaminpropyl |
| hydrogen | dimethylaminomethyl |
| hydrogen | diethylaminomethyl |
| hydrogen | methyl(ethyl)aminomethyl |
| hydrogen | dipropylaminomethyl |

-continued

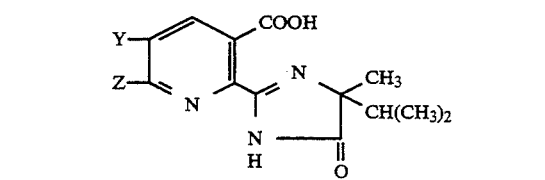

| Y | Z |
|---|---|
| hydrogen | methyl(propyl)aminomethyl |
| hydrogen | ethyl(propyl)aminomethyl |
| hydrogen | 1-dimethylaminoethyl |
| hydrogen | 2-dimethylaminoethyl |
| hydrogen | 1-diethylaminoethyl |
| hydrogen | 2-diethylaminoethyl |
| hydrogen | 3-dimethylaminopropyl |
| hydrogen | (trimethylammonium)methyl |
| hydrogen | (triethylammonium)methyl |
| hydrogen | 1-(trimethylammonium)ethyl |
| hydrogen | 2-(trimethylammonium)ethyl |
| hydrogen | 3-(trimethylammonium)propyl |
| hydrogen | acetoxymethyl |
| hydrogen | propionyloxymethyl |
| hydrogen | butyroyloxymethyl |
| hydrogen | 1-acetoxyethyl |
| hydrogen | 2-acetoxyethyl |
| hydrogen | 3-acetoxypropyl |
| hydrogen | 2-acetoxy-2-methylethyl |
| hydrogen | 2-furyl |
| hydrogen | 3-furyl |
| hydrogen | 3-chloro-2-furyl |
| hydrogen | 4-chloro-2-furyl |
| hydrogen | 5-chloro-2-furyl |
| hydrogen | 2-chloro-3-furyl |
| hydrogen | 4-chloro-3-furyl |
| hydrogen | 5-chloro-3-furyl |
| hydrogen | 3-methyl-2-furyl |
| hydrogen | 5-methyl-2-furyl |
| hydrogen | 2-methyl-3-furyl |
| hydrogen | 5-methyl-3-furyl |
| hydrogen | 2-thienyl |
| hydrogen | 3-thienyl |
| hydrogen | 3-chloro-2-thienyl |
| hydrogen | 4-chloro-2-thienyl |
| hydrogen | 5-chloro-2-thienyl |
| hydrogen | 2-chloro-3-thienyl |
| hydrogen | 4-chloro-3-thienyl |
| hydrogen | 5-chloro-3-thienyl |
| hydrogen | 3-methyl-2-thienyl |
| hydrogen | 5-methyl-2-thienyl |
| hydrogen | 2-methyl-3-thienyl |
| hydrogen | 5-methyl-3-thienyl |
| hydrogen | 5-bromo-2-furyl |
| hydrogen | 5-bromo-2-thienyl |
| hydrogen | N-methyl-2-pyrrolyl |
| hydrogen | N-methyl-3-pyrrolyl |
| hydrogen | amino |
| hydrogen | methoxyamino |
| hydrogen | ethoxyamino |
| hydrogen | n-propyloxyamino |
| hydrogen | i-propyloxyamino |
| hydrogen | n-butoxyamino |
| hydrogen | i-butoxyamino |
| hydrogen | sec-butoxyamino |
| hydrogen | tert-butoxyamino |
| hydrogen | methyl(methoxy)amino |
| hydrogen | ethyl(methoxy)amino |
| hydrogen | methyl(ethoxy)amino |
| hydrogen | ethyl(ethoxy)amino |
| hydrogen | 2-pyridyloxy |
| hydrogen | 4-pyridyloxy |
| hydrogen | 3-fluoro-2-pyridyloxy |
| hydrogen | 3-chloro-2-pyridyloxy |
| hydrogen | 3-methyl-2-pyridyloxy |
| hydrogen | 3,5-dichloro-2-pyridyloxy |
| hydrogen | 3,5-difluoro-2-pyridyloxy |
| hydrogen | 5-trifluoromethyl-2-pyridyloxy |
| hydrogen | 3-fluoro-5-trifluoromethyl-2-pyridyloxy |
| hydrogen | hydroxy |
| vinyl | methyl |

-continued

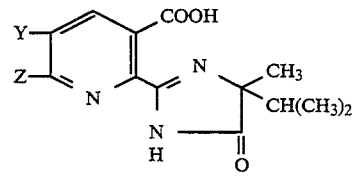

| Y | Z |
|---|---|
| 1-propenyl | methyl |
| allyl | methyl |
| 3-methoxypropenyl | methyl |
| 3-chloropropenyl | methyl |
| 2-trichloromethylvinyl | methyl |
| 1-chlorovinyl | methyl |
| 2-chlorovinyl | methyl |
| isopropenyl | methyl |
| 2-phenylvinyl(cis) | methyl |
| 2-phenylvinyl(trans) | methyl |
| ethynyl | methyl |
| 1-propynyl | methyl |
| 2-propynyl | methyl |
| 3-chloro-1-propynyl | methyl |
| 3-methoxy-1-propynyl | methyl |
| 3-phenyl-1-propynyl | methyl |
| 2-trichloromethyl-1-ethynyl | methyl |
| 2-chloro-1-ethynyl | methyl |
| cyclopropyl | methyl |
| cyclobutyl | methyl |
| cyclopentyl | methyl |
| cyclohexyl | methyl |
| 2,2-dimethyl-1-cyclopropyl | methyl |
| 2-methyl-1-cyclohexyl | methyl |
| 2-chloro-1-cyclohexyl | methyl |
| 2-chloro-1-cyclopropyl | methyl |
| 2-methoxy-1-cyclohexyl | methyl |
| 2-methoxy-1-cyclopropyl | methyl |
| acetyl | methyl |
| propionyl | methyl |
| butyryl | methyl |
| methoxyacetyl | methyl |
| butoxyacetyl | methyl |
| chloroacetyl | methyl |
| dichloroacetyl | methyl |
| trichlororacetyl | methyl |
| 2-chloropropionyl | methyl |
| 3-chloropropionyl | methyl |
| acetamido | methyl |
| propionamido | methyl |
| butyramido | methyl |
| chloroacetamido | methyl |
| dichloroacetamido | methyl |
| trichloroacetamido | methyl |
| methoxyacetamido | methyl |
| 2-chloropropionamido | methyl |
| 3-chloropropionamido | methyl |
| N-methylacetamido | methyl |
| N-ethylacetamido | methyl |
| N-methoxyacetamido | methyl |
| N-butoxyacetamido | methyl |
| N-methylpropionamido | methyl |
| N-methoxypropionamido | methyl |
| N-methylchloroacetamido | methyl |
| N-methoxychloroacetamido | methyl |
| N-methyldichloroacetamido | methyl |
| N-methoxydichloroacetamido | methyl |
| acetoxy | methyl |
| propionyloxy | methyl |
| butyroyloxy | methyl |
| methoxyacetoxy | methyl |
| chloroacetoxy | methyl |
| dichloroacetoxy | methyl |
| trichloroacetoxy | methyl |
| 2-chloropropionyloxy | methyl |
| 3-chloropropionyloxy | methyl |
| 2,2-dichloropropionyloxy | methyl |
| methoxymethyl | methyl |
| ethoxymethyl | methyl |
| n-propoxymethyl | methyl |
| i-propoxymethyl | methyl |
| n-butoxymethyl | methyl |

-continued

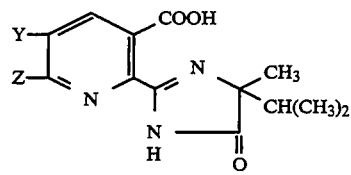

| Y | Z |
|---|---|
| i-butoxymethyl | methyl |
| sec-butoxymethyl | methyl |
| tert-butoxymethyl | methyl |
| 2-methoxyethyl | methyl |
| 2-ethoxyethyl | methyl |
| 2-methoxypropyl | methyl |
| 3-methoxypropyl | methyl |
| 2-methoxy-2-methylethyl | methyl |
| methylthiomethyl | methyl |
| ethylthiomethyl | methyl |
| propylthiomethyl | methyl |
| butylthiomethyl | methyl |
| 1-methylthioethyl | methyl |
| 2-methylthioethyl | methyl |
| 1-methylthiopropyl | methyl |
| 2-methyl-2-methylthioethyl | methyl |
| methylaminomethyl | methyl |
| ethylaminomethyl | methyl |
| n-propylaminomethyl | methyl |
| i-propylaminomethyl | methyl |
| n-butylaminomethyl | methyl |
| i-butylaminomethyl | methyl |
| sec-butylaminomethyl | methyl |
| tert-butylaminomethyl | methyl |
| 2-methylaminoethyl | methyl |
| 2-methylaminopropyl | methyl |
| 2-methylaminobutyl | methyl |
| 2-methyl-2-methylaminoethyl | methyl |
| 3-methylaminpropyl | methyl |
| dimethylaminopropyl | methyl |
| diethylaminomethyl | methyl |
| methyl(ethyl)aminomethyl | methyl |
| dipropylaminomethyl | methyl |
| methyl(propyl)aminomethyl | methyl |
| ethyl(propyl)aminomethyl | methyl |
| 1-dimethylaminoethyl | methyl |
| 2-dimethylaminoethyl | methyl |
| 1-diethylaminoethyl | methyl |
| 2-diethylaminoethyl | methyl |
| 3-dimethylaminopropyl | methyl |
| (trimethylammonium)methyl | methyl |
| (triethylammonium)methyl | methyl |
| 1-(trimethylammonium)ethyl | methyl |
| 2-(trimethylammonium)ethyl | methyl |
| 3-(trimethylammonium)propyl | methyl |
| acetoxymethyl | methyl |
| propionyloxymethyl | methyl |
| butyroyloxymethyl | methyl |
| 1-acetoxyethyl | methyl |
| 2-acetoxyethyl | methyl |
| 3-acetoxypropyl | methyl |
| 2-acetoxy-2-methylethyl | methyl |
| 2-furyl | methyl |
| 3-furyl | methyl |
| 3-chloro-2-furyl | methyl |
| 4-chloro-2-furyl | methyl |
| 5-chloro-2-furyl | methyl |
| 2-chloro-3-furyl | methyl |
| 4-chloro-3-furyl | methyl |
| 5-chloro-3-furyl | methyl |
| 3-methyl-2-furyl | methyl |
| 5-methyl-2-furyl | methyl |
| 2-methyl-3-furyl | methyl |
| 5-methyl-3-furyl | methyl |
| 2-thienyl | methyl |
| 3-thienyl | methyl |
| 3-chloro-2-thienyl | methyl |
| 4-chloro-2-thienyl | methyl |
| 5-chloro-2-thienyl | methyl |
| 2-chloro-3-thienyl | methyl |
| 4-chloro-3-thienyl | methyl |
| 5-chloro-3-thienyl | methyl |

-continued

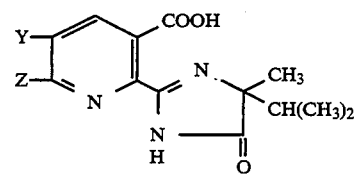

| Y | Z |
|---|---|
| 3-methyl-2-thienyl | methyl |
| 5-methyl-2-thienyl | methyl |
| 2-methyl-3-thienyl | methyl |
| 5-methyl-3-thienyl | methyl |
| 5-bromo-2-furyl | methyl |
| 5-bromo-2-thienyl | methyl |
| N-methyl-2-pyrrolyl | methyl |
| N-methyl-3-pyrrolyl | methyl |
| amino | methyl |
| methoxyamino | methyl |
| ethoxyamino | methyl |
| n-propyloxyamino | methyl |
| i-propyloxyamino | methyl |
| n-butoxyamino | methyl |
| i-butoxyamino | methyl |
| sec-butyamino | methyl |
| tert-butoxyamino | methyl |
| methyl(methoxyamino | methyl |
| ethyl(methoxy)amino | methyl |
| methyl(ethoxy)amino | methyl |
| ethyl(ethoxy)amino | methyl |
| 2-pyridyloxy | methyl |
| 4-pyridyloxy | methyl |
| 3-fluoro-2-pyridyloxy | methyl |
| 3-chloro-2-pyridyloxy | methyl |
| 3-methyl-2-pyridyloxy | methyl |
| 3,5-dichloro-2-pyridyloxy | methyl |
| 3,5-difluoro-2-pyridyloxy | methyl |
| 5-trifluoromethyl-2-pyridyloxy | methyl |
| 3-fluoro-5-trifluoromethyl-2-pyridyloxy | methyl |
| hydroxy | methyl |
| methyl | vinyl |
| methyl | 1-propenyl |
| methyl | allyl |
| methyl | 1-chlorovinyl |
| methyl | 2-chlorovinyl |
| methyl | ethynyl |
| methyl | acetyl |
| methyl | chloroacetyl |
| methyl | acetamido |
| methyl | chloroacetamido |
| methyl | N-methylacetamido |
| methyl | acetoxy |
| methyl | chloroacetoxy |
| methyl | methoxymethyl |
| methyl | methylthiomethyl |
| methyl | methylaminomethyl |
| methyl | dimethylaminomethyl |
| methyl | acetoxymethyl |
| methyl | 2-furyl |
| methyl | 2-thienyl |
| methyl | amino |
| methyl | hydroxy |
| methyl | methoxyamino |
| methyl | 3-fluoro-5-trifluoromethyl-2-pyridyloxy |
| chloro | vinyl |
| chloro | acetyl |
| chloro | ethynyl |
| chloro | acetamido |
| chloro | acetoxy |
| chloro | methoxymethyl |
| chloro | acetoxymethyl |
| chloro | 2-furyl |
| chloro | 2-thienyl |
| chloro | amino |
| chloro | hydroxy |
| chloro | methoxyamino |
| vinyl | chloro |
| 1-propenyl | chloro |
| isopropenyl | chloro |

-continued

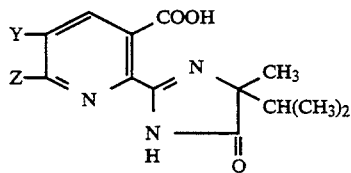

| Y | Z |
|---|---|
| allyl | chloro |
| 1-chlorovinyl | chloro |
| 2-chlorovinyl | chloro |
| ethynyl | chloro |
| acetyl | chloro |
| chloroacetyl | chloro |
| acetamido | chloro |
| chloroacetamido | chloro |
| N-methylacetamido | chloro |
| acetoxy | chloro |
| chloroacetoxy | chloro |
| methoxymethyl | chloro |
| methylthiomethyl | chloro |
| methylaminomethyl | chloro |
| dimethylaminomethyl | chloro |
| acetoxymethyl | chloro |
| 2-furyl | chloro |
| 2-thienyl | chloro |
| 3-furyl | chloro |
| 3-thienyl | chloro |
| amino | chloro |
| hydroxy | chloro |
| methoxyamino | chloro |
| 3-fluoro-5-trifluoromethyl-2-pyridyloxy | chloro |
| vinyl | fluoro |
| 1-propenyl | fluoro |
| isopropenyl | fluoro |
| allyl | fluoro |
| 1-chlorovinyl | fluoro |
| 2-chlorovinyl | fluoro |
| ethynyl | fluoro |
| acetyl | fluoro |
| chloroacetyl | fluoro |
| acetamido | fluoro |
| chloroacetamido | fluoro |
| N-methylacetamido | fluoro |
| acetoxy | fluoro |
| chloroacetoxy | fluoro |
| methoxymethyl | fluoro |
| methylthiomethyl | fluoro |
| methylaminomethyl | fluoro |
| dimethylaminomethyl | fluoro |
| acetoxymethyl | fluoro |
| 2-furyl | fluoro |
| 2-thienyl | fluoro |
| 3-furyl | fluoro |
| 3-thienyl | fluoro |
| amino | fluoro |
| hydroxy | fluoro |
| methoxyamino | fluoro |
| 3-fluoro-5-trifluoromethyl-2-pyridyloxy | fluoro |

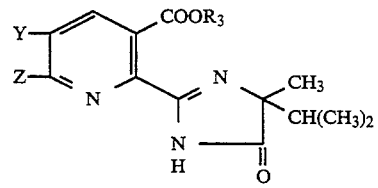

| Y | Z | R₃ |
|---|---|---|
| vinyl | hydrogen | methyl |
| ethynyl | hydrogen | ethyl |
| 2-furyl | hydrogen | 2-methoxyethyl |

-continued

| Y | Z | R₃ |
|---|---|---|
| methylthiomethyl | hydrogen | furfuryl |
| acetoxymethyl | hydrogen | propargyl |
| hydrogen | methoxymethyl | methyl |
| hydrogen | N-methylacetamido | 2-methoxyethyl |
| hydrogen | chloroacetoxy | allyl |

The formula I compounds of this invention are effective herbicidal agents useful for the control of a variety of monocotyledonous and dicotyledonous plants. These compounds are herbicidally effective for controlling weeds indigenous to both dry land and wet land areas. They are also useful as aquatic herbicides and are effective for controlling the above-said plants when applied to the foliage thereof or to the soil or water containing seeds or other propagating organs of said plants such as tubers, rhizomes or stolons, at rates of from about 0.016 to 8.0 kg/ha.

The formula I and formula II compounds of this invention can be formulated as wettable powders, flowable concentrates, granular formulations and the like.

Wettable powders can be prepared by grinding together about 20% to 45% by weight of a finely divided carrier such as kaolin, bentonite, diatomaceous earth, attapulgite, or the like, 45% to 80% by weight of the active compound, 2% to 5% by weight of a dispersing agent such as sodium lignosulfonate, and 2% to 5% by weight of a nonionic surfactant, such as octylphenoxy polyethoxy ethanol, nonylphenoxy polyethoxy ethanol or the like.

A typical flowable fluid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

A typical emulsifiable concentrate can be prepared by dissolving about 5% to 25% by weight of the active ingredient in about 65% to 90% by weight of N-methylpyrrolidone, isophorone, butyl cellosolve, methylacetate or the like and dispersing therein about 5% to 10% by weight of a nonionic surfactant such as an alkylphenoxy polyethoxy alcohol. This concentrate is dispersed in water for application as a liquid spray.

When the compounds of the invention are to be used as herbicides where soil treatments are involved, the compounds may be prepared and applied as granular products. Preparation of the granular product can be achieved by dissolving the active compound in a solvent such as methylene chloride, N-methylpyrrolidone or the like and spraying the thus prepared solution on a granular carrier such as corncob grits, sand, attapulgite, kaolin or the like.

The granular product thus prepared generally comprises about 3% to 20% by weight of the active ingredient and about 97% to 80% by weight of the granular carrier.

In order to facilitate a further understanding of the invention, the following examples are presented primarily for the purpose of illustrating certain more specific details thereof.

EXAMPLE 1

Preparation of 6-(4-isopropyl-4-methyl-5-oxo-2-imidazolin-2-yl)pyridine-3-carboxaldehyde

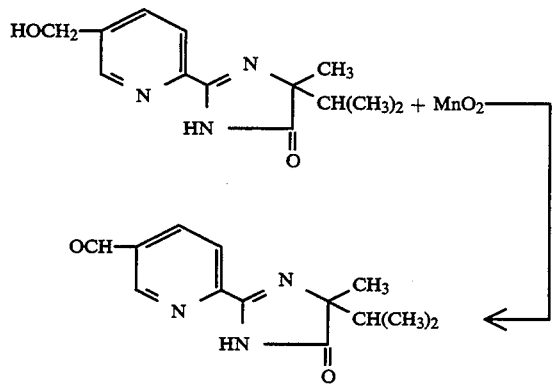

To a stirred solution containing 18 g hydroxymethyl pyridine in 180 mL dry methylene chloride under nitrogen is added 44.3 g of activated manganese dioxide. The mixture is heated under reflux for four hours. The mixture is filtered and the filtrate concentrated. Trituration of the residue with ether-hexane gave a crystalline solid. This is recrystallized from ether-hexane to give analytically pure 6-(4-isopropyl-4-methyl-5-oxo-2-imidazolin-2-yl)pyridine-3-carboxaldehyde, mp 105.5°–108° C.

EXAMPLE 2

Preparation of 2-(5-Styryl-2-pyridyl)-4-isopropyl-4-methyl-2-imidazolin-5-one

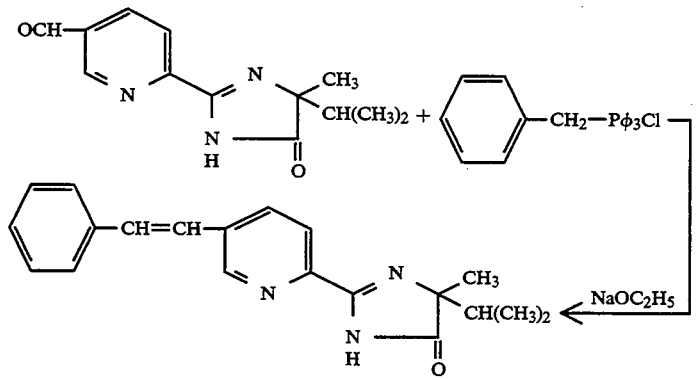

To a solution of 2.72 g of sodium ethoxide (0.04 mol) in 100 mL absolute ethanol, stirred at room temperature under nitrogen, is added 7.9 g (0.02 mol) (benzyl) triphenylphosphonium chloride. After 5 minutes, 5.0 g 6-(4-isopropyl-4-methyl-5-oxo-2-imidazolin-2-yl)pyridine-3-carboxaldehyde (0.02 mol) is added all at once, and the mixture is stirred at room temperature for 24 hours. The mixture is concentrated in vacuo, and the residue is chromatographed on silica gel using ether-hexane as eluant to give 0.4 g of the desired product as the pure cis isomer (oil), 4.5 g product as an isomeric mixture, and 1.25 g of the trans isomer, mp 128°–133° C.

EXAMPLE 3

Preparation of 2-(4-isopropyl-4-methyl-5-oxo-2-imidazolin-2-yl)-5-styrylnicotonic acid, (Z)

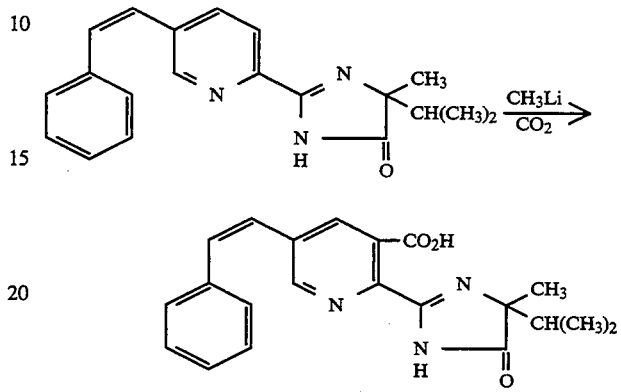

To a solution of 2.07 g of 2-(5-styryl-2-pyridyl)-5-isopropyl-5-methyl-2-imidazolin-4-one in 100 mL dry tetrahydrofuran, stirred at $-70°$ C. under nitrogen, is added slowly 9 mL of 1.6M methyllithium. After stirring the reaction mixture at $-10°$ for 1 hour, it is slowly syringed into a saturated solution of carbon dioxide in tetrahydrofuran. After stirring the resulting mixture overnight, the solvent is removed in vacuo; the residue is dissolved in water, washed with methylene chloride, and the aqueous phase is acidified to pH 3 and extracted with methylene chloride. The combined extracts are dried and concentrated in vacuo to afford the product. Recrystallization from methylene chloride-hexanes affords a solid, mp 122.5°–126°.

Utilizing the above procedure and substituting the appropriate 2-pyridyl-5-isopropy-5-methyl-2-imidazoline-4-one yields the compounds below:

| R | mp |
|---|---|
| 5-styryl (E) | 169–171° |
| 5-CH₂ C— CH₃ | 166.5°–168° |

EXAMPLE 4

Preparation of methyl-5-isopropenyl-2-(4-isopropyl-4-methyl-5-oxo-2-imidazolin-2-yl)nicotinate

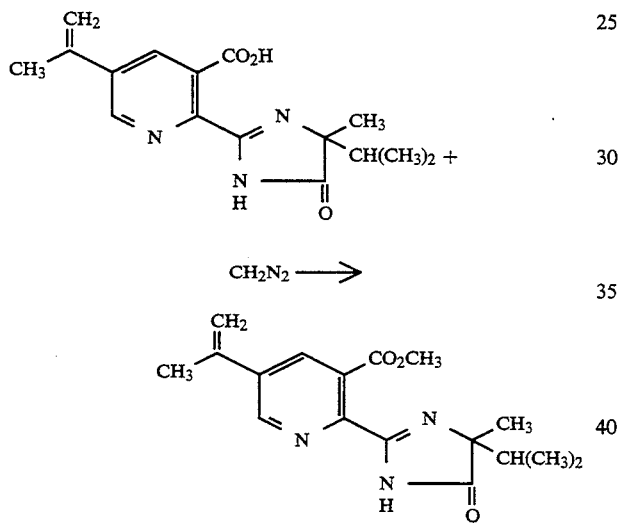

To a solution of 4.9 g of 5-isopropenyl-2-(5-isopropyl-5-methyl-4-oxo-2-imidazolin-2-yl)nicotinic acid in 50 mL of methylene chloride, stirred at 0°, is added 60 mL of 0.25M ethereal diazomethane. After stirring for 15 minutes, the reaction is concentrated on a steam bath. The residue is chromatographed on silica gel using 2:1 ether-hexanes as eluant to afford the desired product. Recrystallization from ether-hexanes affords a solid, mp 90.5°–92.5°.

EXAMPLE 5

Preparation of 5-allylpyridine-2,3-dicarboxylic acid

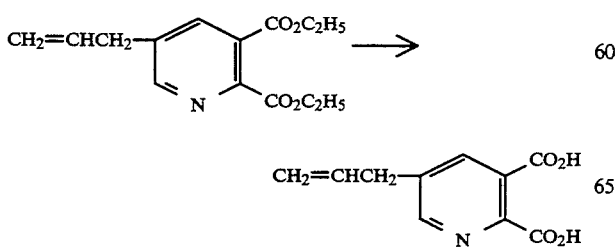

To a solution of 6.07 g of diethyl 5-allylpyridine-2,3-dicarboxylate in 20 mL of methanol, stirred under nitrogen, is added slowly a solution of 3.3 g of sodium hydroxide in 13 mL water. After diluting the reaction mixture with 10 mL each of water and methanol, it is heated at reflux for 1¾ hours. The reaction is cooled in an ice bath, acidified to pH 3 with concentrated hydrochloric acid, and concentrated in vacuo to a damp solid. This solid is reevaporated from pyridine to afford the product as a brown solid, mp>250°(dec).

The following are prepared in similar fashion:

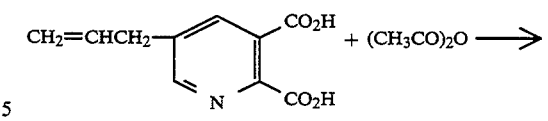

| Y | Z | mp |
|---|---|---|
| CH₃OC— | CH₃ | solid |
| H | (furan) | solid |
| (thiophene) | H | solid |
| H | (thiophene) | solid |
| (thiophene) | H | solid |
| H | (cyclohexyl) | 250–252° (dec) |
| CH₃CONH | CH₃ | 198–200° (dec) |

EXAMPLE 6

Preparation of 5-allylpyridine-2,3-dicarboxylic anhydride

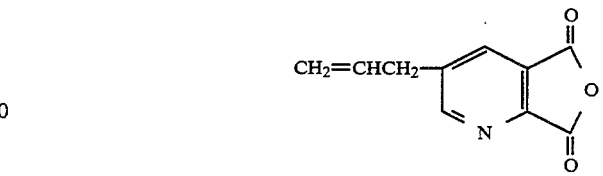

A mixture of 7 g of crude 5-allylpyridine-2,3-dicarboxylic acid, 9.8 mL acetic anhydride, and 3.3 mL pyridine in 100 mL dry 1,2-dimethoxyethane is stirred under nitrogen and heated at 65° for 1 hour. After adding an additional 1 mL of acetic anhydride, the reaction is heated for 2 hours at 65°, then at reflux overnight. The reaction mixture is filtered, and the solids are washed with ether and ethyl acetate. The combined filtrates are concentrated in vacuo and reevaporated from xylenes to afford the product as a solid.

Similarly were prepared the following:

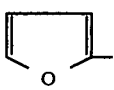

| Y | Z | mp |
|---|---|---|
| CH₃C(=O) | CH₃ | solid |
| H | —O—C(=O)CH₃ | solid |
| H | (furan-2-yl) | solid |
| (thien-2-yl) | H | solid |
| H | (thien-2-yl) | solid |
| (thien-2-yl) | H | solid |

EXAMPLE 7

Preparation of 2-(4-isopropyl-4-methyl-5-oxo-2-imidazolin-2-yl)-5-propenylnicotinic acid and its picolinic acid isomer

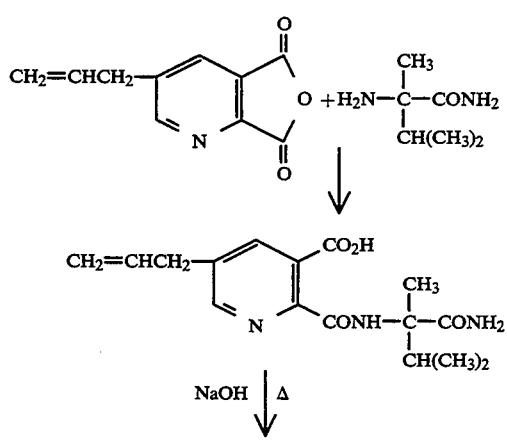

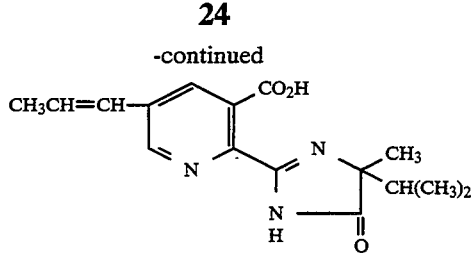

A mixture of 2.88 g of 5-allylpyridine-2,3-dicarboxylic anhydride and 2.0 g of 2-amino-2,3-dimethylbutyramide in 40 mL of dry tetrahydrofuran is stirred under nitrogen and heated at reflux for 2 hours. The reaction is cooled and concentrated in vacuo to afford a mixture if acid-diamides as a gum.

The gum can be redigested in hot tetrahydrofuran, heated at reflux overnight, cooled, diluted with some ether, and filtered to afford the isomerically pure intermediate, 5-allyl-2-[(1-carbamoyl-1,2-dimethylpropyl)-carbamoyl]nicotinic acid as a solid.

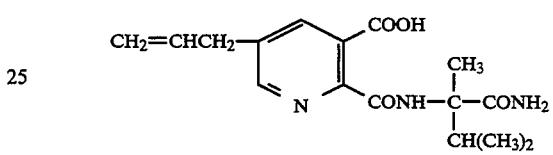

Using essentially the same procedure, but substituting 2-amino-2,3-dimethylthiobutyramide for 2-amino-2,3-dimethylbutyramide affords the corresponding 2-(4-isopropyl-4-methyl-5-thioxo-2-imidazolin-2-yl)-5-propenylnicotinic acid as a solid. This material is digested in 15.2 mL of 5N sodium hydroxide and heated at 80° for 1 hour. The reaction is cooled, acidified to pH 3 with 4N hydrochloric acid and extracted with methylene chloride and ethyl acetate. The combined extracts are dried and concentrated in vacuo to afford 2.68 g crude product as a gummy isomeric mixture.

As above, followed by fractional crystallization, affords the following:

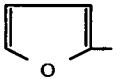

| Y | Z | mp |
|---|---|---|
| CH₃C(=O) | CH₃ | 158–160° |
| H | (furan-2-yl) | 253.0–261.0° (dec) |
| (thien-2-yl) | H | 211.5–213.0° |
| H | (thien-2-yl) | 255.0–261.0° (dec) |

-continued

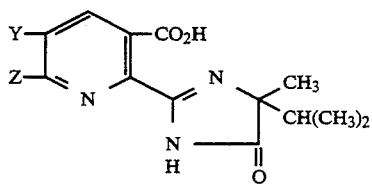

| Y | Z | mp |
|---|---|---|
| ⟨thiophene⟩ | H | 172.0–174.0° |
| ⟨cyclohexyl⟩ | H | 207.0–209.0° |
| CH₃SO₂N(CH₃)— | CH₃ | 213.0–216.0° |
| CH₃OCH₂— | CH₃ | 89.0–92.0° |
| CH₃ | CH₃OCH₂— | — |
| H | CH₃OCH₂ | 160.0–163.0° |
| H | CH₃—CH(OCH₃)— | 150.0–154.0° |

EXAMPLE 8

Preparation of methyl 2-(4-isopropyl-4-methyl-5-oxo-2-imidazolin-2-yl)-5-propenylnicotinate and its picolinate isomer

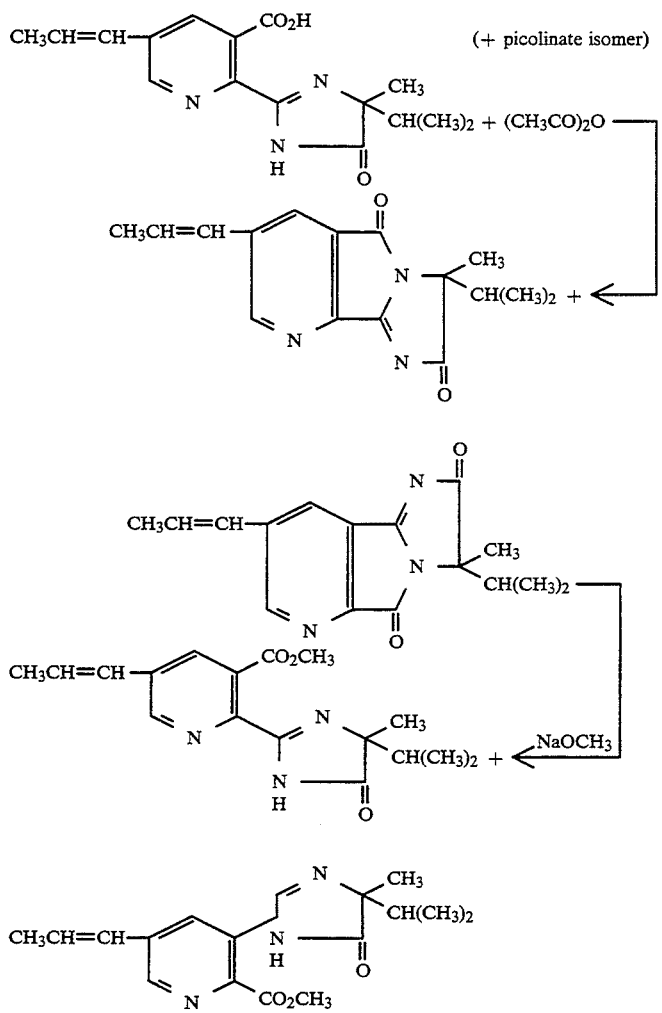

(+ picolinate isomer)

A mixture of 2.68 g of 2-(4-isopropyl-4-methyl-5-oxo-2-imidazolin-2-yl)-5-propenylnicotinic acid and its picolinic acid isomer and 1.85 mL of acetic anhydride in 20 mL toluene is stirred under nitrogen and heated at reflux for 2½ hours. Solvent is removed in vacuo, and the residual gum is reevaporated from xylenes. The residue is dissolved in 20 mL methanol, 0.75 g of sodium methoxide is added, and the mixture is stirred at room temperature for 3 hours. The reaction is then acidified with glacial acetic acid to pH 5, stirred overnight, and concentrated in vacuo. The residue is partitioned between methylene chloride and water, and the aqueous phase is further extracted with methylene chloride. The combined extracts are dried and concentrated in vacuo to an oil. Chromatography on silica gel using ether-hexane mixtures affords 1.85 g of the nicotinate, and 0.56 g of the picolinate. Using the same procedure on isomerically pure 2-(4-isopropyl-4-methyl-5-oxo-2-imidazolin-2-yl)-5-propenylnicotinic acid affords the isomerically pure intermediate, 3-isopropyl-3-methyl-7-propenyl-5H-imidazo[1:2:1,2]pyrrdo[3,4-b]pyridine-2(3H),5-dione, as a solid.

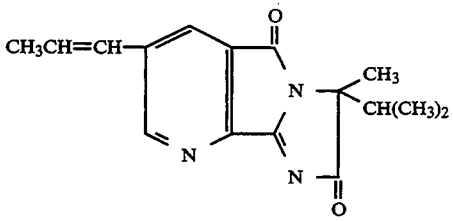

Recrystallization of the nicotinate from methylene chloride-hexanes gives 1.37 g of a solid, mp 122.5°–124.5°.

Using essentially the same procedure, and substituting the appropriate pyridine precursor and the appropriate nucleophile, the following were prepared.

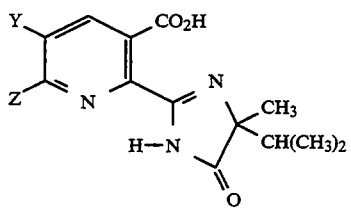

| Y | Z | R | mp |
|---|---|---|---|
| CH≡C— | H | CH₃ | 118–124° |
| CH₃C≡C— | H | CH₃ | 118–120° |
| H | (thienyl) | CH₃ | 138–140.5° |
| H | (furyl) | CH₃ | 168–173.5° |
| NH₂— | CH₃ | CH₃ | 169–173° |
| CH₃CONH— | CH₃ | CH₃ | 162–165° |
| CH₃CONH— | CH₃ | ØCH₂ | 195–196° |
| CH₃CON(CH₃)— | CH₃ | CH₃ | 191–195° |

EXAMPLE 9

Preparation of 2-(4-isopropyl-4-methyl-5-oxo-2-imidazolin-2-yl)-5-propenylnicotinic acid

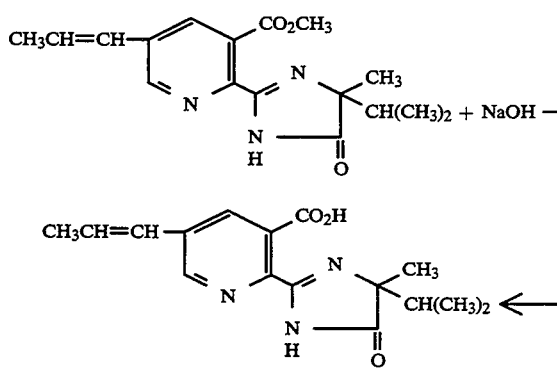

A mixture of 1.5 g methyl 2-(4-isopropyl-4-methyl-5-oxo-2-imidazolin-2-yl)-5-propenylnicotinate and 3.2 mL of 2N sodium hydroxide in 15 mL methanol is stirred under nitrogen and heated at 45° for 3½ hours. The reaction is cooled to 10°, acidified to pH 3 with 2N hydrochloric acid, and concentrated in vacuo. The residue is partitioned between methylene chloride and water, and the aqueous phase is further extracted with methylene chloride. The combined organic phases are dried and concentrated in vacuo to a solid. Recrystallization from methylene chloride-hexanes gives a solid, mp 175°–176°.

Using essentially the same conditions, and substituting the appropriate nicotinate precursor, the following are obtained:

| Y | Z | mp |
|---|---|---|
| CH₃OC— | H | 191.5–192.5° |
| CH₃SCH₂— | H | 162.0–165.0° |
| H | CH₃SCH₂— | 113.0–116.0° |
| CH₃OCH₂ | H | 160.0–162.0° |
| CH₃—C(OH)(CH₃)—C≡C— | H | 158.0–160.0° |
| CH₂=CH— | H | 183.0–184.0° |
| C₆H₅SCH₂— | H | 160.0–160.5° |
| CH₃C≡C— | H | 185.0–189.0° |
| C₆H₅SOCH₂— | H | 122.0–123.0° |
| C₆H₅SO₂CH₂— | H | 220.0–224.0° |
| (CH₃O)₂CH— | H | oil |
| CH₃OCH₂— | CH₃O— | 180.0–181.0° |
| CH₃CH(OCH₃)— | H | glass |
| CH₃CH(OCH₃)— | CH₃ | 170.0–171.0° |
| NH₂— | H | 210.0–220.0° |
| CH₃CONH— | H | 275.0–278.0° (dec) |
| CHO | H | 187.0–198.0° |
| CH₃OCONH— | CH₃ | 218.0–221.0° (dec) |
| NH₂ | CH₃ | 265.0–268.0° |
| CH₃CONH— | CH₃ | 208.0–210.0° |

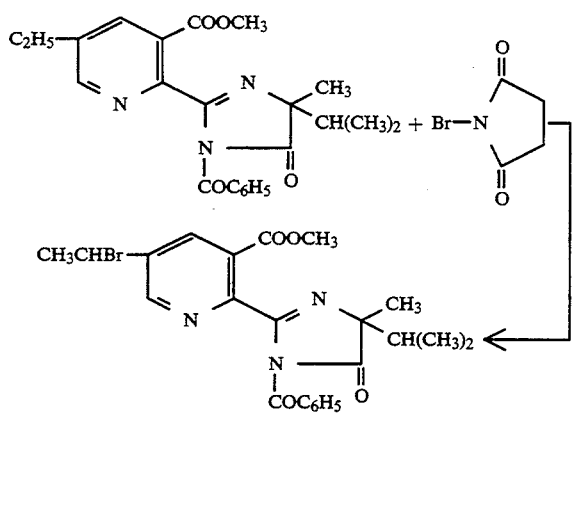

| Y | Z | mp |
|---|---|---|
| CH₃CON(CH₃)— | CH₃ | 196.0–200.0° |

EXAMPLE 10

Preparation of methyl 2-(1-benzoyl-4-isopropyl-4-methyl-5-oxo-2-imidazolin-2-yl)-5-(1-bromoethyl)nicotinate A mixture of 38.6 g methyl 2-(1-benzoyl-4-isopropyl-4-methyl-5-oxo-2-imidazolin-2-yl)-5-ethylnicotinate, 16.9 g N-bromosuccinimide and 2.3 g benzoyl peroxide in 740 mL carbon tetrachloride is stirred under nitrogen and heated at reflux using a sunlamp for 1½ hours. The reaction mixture is cooled, filtered through celite, and the filtrate is concentrated in vacuo to an orange oil. This oil is partitioned between 400 mL each of water and methylene chloride. The aqueous layer is further extracted with methylene chloride, and the combined organic phases are dried over sodium sulfate and concentrated in vacuo to give 49.8 g of a cloudy orange glass; NMR shows the desired product to be the major component.

Using essentially the same conditions, and substituting the appropriate nicotinate precursor, the following are obtained:

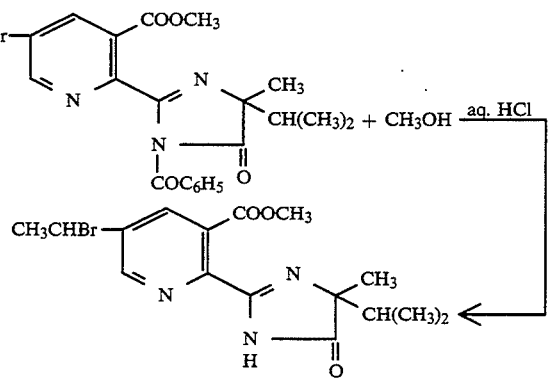

| Y | Z | mp |
|---|---|---|
| BrCH₂ | H | 88–119° |
| Br₂CH | H | 59–68° |

EXAMPLE 11

Preparation of methyl 2-(4-isopropyl-4-methyl-5-oxo-2-imidazolin-2-yl)-5-(1-bromoethyl)nicotinate A solution of 49.6 g of crude methyl 2-(1-benzoyl-4-isopropyl-4-methyl-5-oxo-2-imidazolin-2-yl)-5-(1-bromoethyl) nicotinate (See Exp. 10) in 300 mL of methanol is stirred at room temperature and 400 mL of 50% aqueous methanol (2N in hydrogen chloride) is added dropwise over 1 hour. After stirring the reaction for an additional 2 hours, it is concentrated in vacuo. The pH of the residue is adjusted to 6 with 2N aqueous sodium hydroxide, and the mixture is extracted with 4×200 mL methylene chloride. The combined extracts are dried and concentrated in vacuo to afford the crude desired product as a thick oil. A portion is chromatographed on silica gel using ether-hexane as eluant and recrystallized from methylene chloride-hexane to give the desired product as a light orange solid, mp 123°–126° C.

Using essentially the same conditions, and substituting the appropriate nicotinate precursor, the following are obtained:

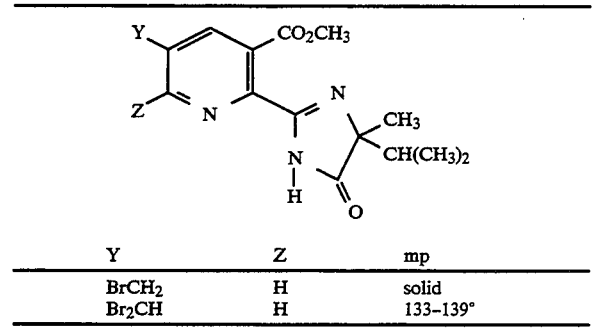

| Y | Z | mp |
|---|---|---|
| BrCH$_2$ | H | solid |
| Br$_2$CH | H | 133–139° |

| Y | Z | mp |
|---|---|---|
| CH$_3$SCH$_2$ | H | oil |
| CH$_3$OCH$_2$ | H | 88–89° |
| C$_6$H$_5$SCH$_2$ | H | 135–138° |

EXAMPLE 12

Preparation of methyl 5-(1-acetoxyethyl)-2-(4-isopropyl-4-methyl-5-oxo-2-imidazolin-2-yl)nicotinate

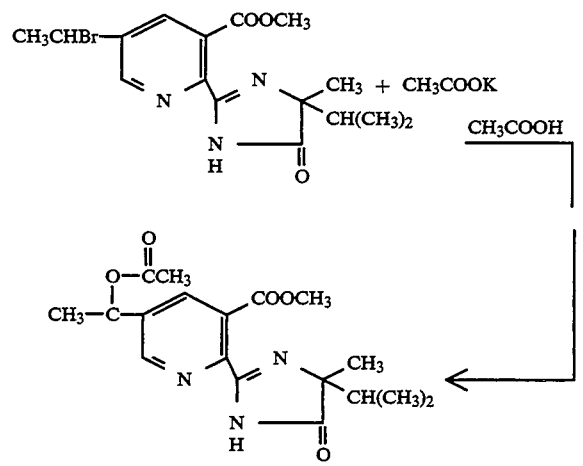

A mixture of 12 g of methyl 2-(4-isopropyl-4-methyl-5-oxo-2-imidazolin-2-yl)-5-(1-bromoethyl)nicotinate, 3.1 g potassium acetate and 30 mL acetic acid is stirred under nitrogen and heated at reflux for 8 hours. The reaction mixture is filtered, and the filtrate is concentrated in vacuo. The residue is triturated with ether, filtered, and concentrated in vacuo to give the desired product as an amber glass.

Using essentially the same conditions as described above, and using the appropriate 5-(1-bromalkyl)-2-(4-isopropyl-4-methyl-5-oxo-2-imidazolin-2-yl)nicotinate and appropriate nucleophile, the following are prepared:

EXAMPLE 13

Preparation of methyl 5-(1-hydroxyethyl)-2-(4-isopropyl-4-methyl-5-oxo-2-imidazolin-2-yl)nicotinate A solution of 16 g of methyl 5-(1-acetoxyethyl)-2-(4-isopropyl-4-methyl-5-oxo-2-imidazolin-2-yl)nicotinate and 0.5 g sodium methoxide in 150 mL methanol is stirred at room temperature under nitrogen for 5 days. The reaction is acidified to pH 5 with acetic acid and concentrated in vacuo. The residue is partitioned between methylene chloride and water, the aqueous layer is further extracted with methylene chloride, and the combined organic phases are dried over sodium sulfate and concentrated in vacuo to an orange oil. Column chromatography of this oil using ether-hexane as eluent affords the desired product as a white foam.

EXAMPLE 14

Preparation of methyl 5-acetyl-2-(4-isopropyl-4-methyl-5-oxo-2-imidazolin-2-yl)nicotinate

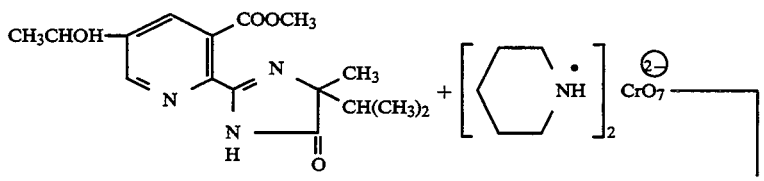

-continued

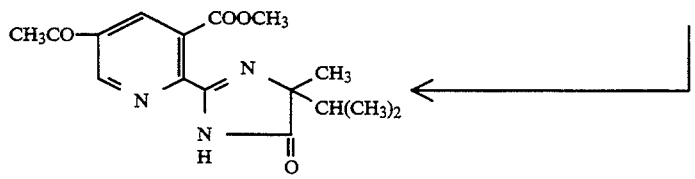

A mixture of 8.2 g of methyl 5-(1-hydroxyethyl)-2-(4-isopropyl-4-methyl-5-oxo-2-imidazolin-2-yl)nicotinate, 14.5 g of pyridinum dichromate and 1.99 g of pyridinium trifluoroacetate in 30 mL of methylene chloride is stirred at room temperature under nitrogen for 3 days. The reaction mixture is flash-chromatographed through florisil using methylene chloride as eluent, and the combined eluates are washed with water, dried, and concentrated in vacuo to a dark oil. Chromatography of this oil on silica gel using ether-hexane as eluant affords the desired product as a solid. Recrystallization of this solid from methylene chloride-hexane affords a white solid, mp 105°–108° C.

EXAMPLE 15

Preparation of 5H-Imidazo[1',2':1,2]pyrrolo[3,4-b]pyridine-3(2H),5-dione, 7-acetyl-2,8-dimethyl-2-isopropyl

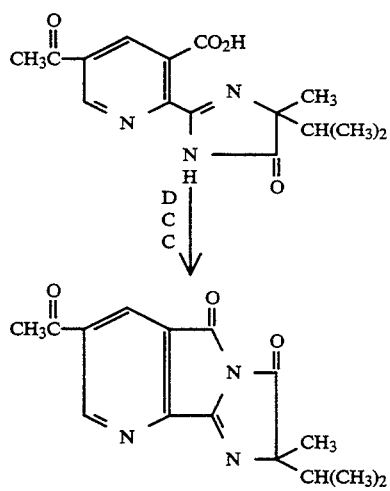

A solution of 2.6 g 5-acetyl-2-(4-isopropyl-4-methyl-5-oxo-2-imidazolin-2-yl)nicotinic acid and 1.86 g DCC in 100 mL methylene chloride is stirred at room temperature overnight. An additional 1.86 g DCC is added and stirring continued over the weekend; a further 1.86 g of DCC is added, and stirring continued for 1 more day. The reaction mixture is filtered, and the filtrate is stripped. Chromatography of the residue on silica gel using 5% ethyl acetate in methylene chloride affords 1.68 g of the desired product, mp 158°–160°.

Using essentially the same procedure and substituting the appropriate precursor, the following are obtained:

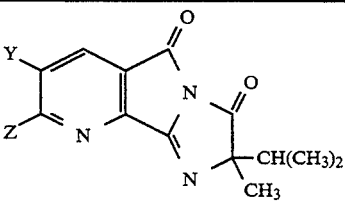

| Y | Z | mp |
|---|---|---|
| CH$_3$OCH$_2$ | H | oil |

EXAMPLE 16

Preparation of methyl 5-acetyl-2-(4-isopropyl-4-methyl-5-oxo-2-imidazolin-2-yl)-6-methylnicotinate

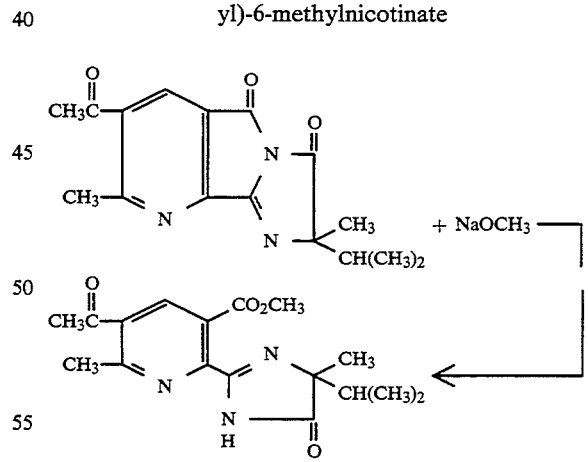

A solution of 0.68 g of 7-acetyl-2,8-dimethyl-2-isopropyl-5H-imidazo[1',2':1,2]pyrrolo[3,4-b]pyridine-3(2H),5-dione in 50 mL methanol is stirred at 5° and 0.06 g of sodium methoxide is added. The reaction is stirred and allowed to warm to room temperature over 3 hours, at which point it is acidified with acetic acid and concentrated in vacuo. The residue is dissolved in methylene chloride, washed with water, dried and concentrated in vacuo to afford the desired product. Recrystallization from methylene chloride-hexanes gives a solid, mp 118°–120°.

EXAMPLE 17

Preparation of furfuryl 5-acetyl-2-(4-isopropyl-4-methyl-5-oxo-2-imidazolin-2-yl)-6-methylnicotinate

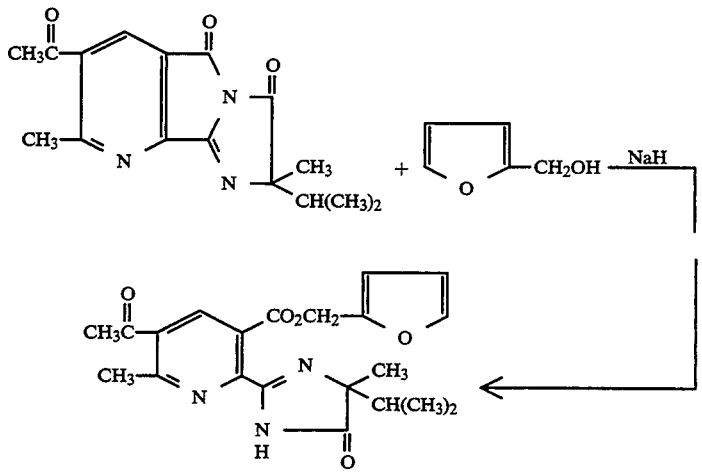

A solution of 1.0 g of 7-acetyl-2,8-dimethyl-2-isopropyl-5H-imidazo[1',2':1,2]pyrrolo[3,4-b]-pyridine-3(2H),5-dione in 50 mL tetrahydrofuran is added dropwise to a preformed mixture of 0.03 g sodium hydride and 0.35 mL furfuryl alcohol in 50 mL tetrahydrofuran. The reaction mixture is stirred at room temperature overnight, acidified with acetic acid, and concentrated in vacuo. The residue is chromatographed on silica gel using 5% ethyl acetate in methylene chloride as eluant to afford the desired product. Recrystallization from methylene chloride-hexanes gives a solid, mp 133°–136°.

Using essentially the same procedure, and substituting the appropriate pyridine precursor and nucleophile, the following are obtained:

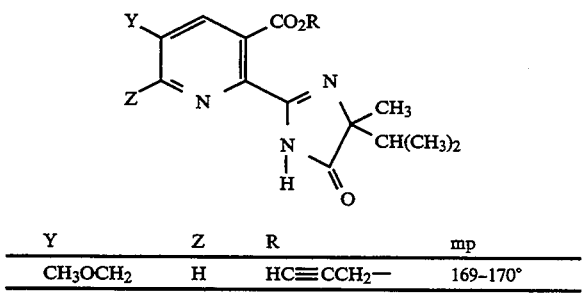

| Y | Z | R | mp |
|---|---|---|---|
| CH$_3$OCH$_2$ | H | HC≡CCH$_2$— | 169–170° |

EXAMPLE 18

Preparation of methyl 2-(1-acetyl-4-isopropyl-4-methyl-5-oxo-2-imidazolin-2-yl)-6-methylnicotinate

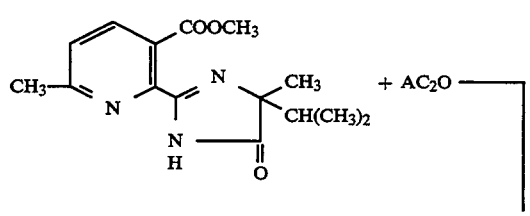

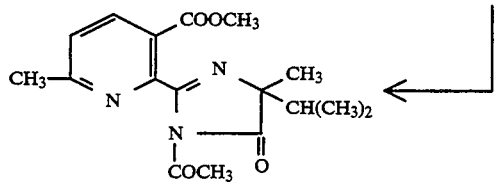

A solution of 33.2 g of methyl 2-(4-isopropyl-4-methyl-5-oxo-2-imidazolin-2-yl)-6-methylnicotinate in 350 mL of acetic anhydride is stirred and heated at reflux for 4 hours. The solution is concentrated in vacuo, and the residue is triturated with 2:1 hexane-ether to give the desired product as a white solid.

EXAMPLE 19

Preparation of methyl 2-(1-acetyl-4-isopropyl-4-methyl-5-oxo-2-imidazolin-2-yl)-6-methylnicotinate-1-oxide

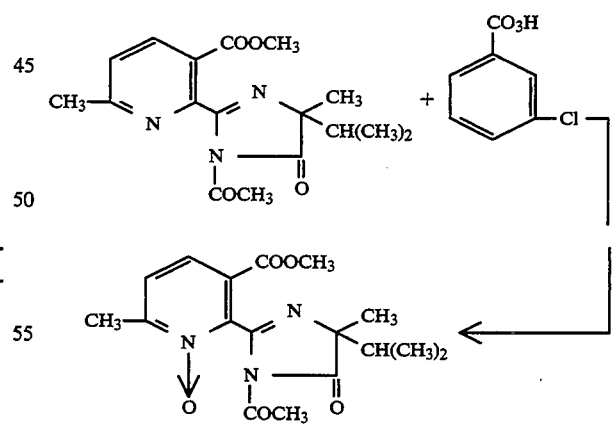

A solution of 29 g of methyl 2-(1-acetyl-4-isopropyl-4-methyl-5-oxo-2-imidazolin-2-yl)-6-methylnicotinate and 28.7 g of 80% M-chloroperbenzoic acid in 250 mL of methylene chloride is stirred and heated at reflux for 3½ hours. The reaction mixture is filtered, and the solid is thoroughly washed with methylene chloride. The combined filtrates are cooled and treated cautiously with saturated aqueous sodium bisulfite until a negative starch-iodide test is obtained. The mixture is again filtered, and the organic layer is washed with saturated sodium bicarbonate solution, dried, and concentrated in vacuo to give an oil. Trituration of this oil with ether affords the desired product as a pale yellow solid, mp 135°–138.5° C.

EXAMPLE 20

Preparation of methyl 6-acetoxymethyl-2-(1-acetyl-4-isopropyl-4-methyl-5-oxo-2-imidazolin-2-yl)nicotinate

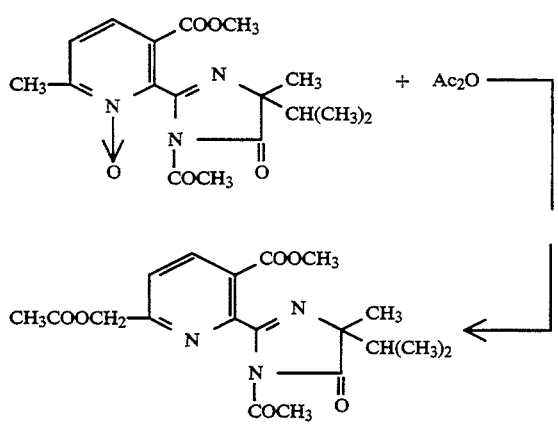

A solution of 37.6 g of methyl 2-(1-acetyl-4-isopropyl-4-methyl-5-oxo-2-imidazolin-2-yl)-6-methylnicotinate-1-oxide in 350 mL of acetic anhydride is stirred and heated at reflux for 3½ hours. The reaction is concentrated in vacuo, and the residue is chromatographed on silica gel using hexane-ethyl acetate as eluant to give the desired product as a solid. Recrystallization of the solid from methylene chloride-hexanes affords analytically pure material, mp 111°–112° C.

Using essentially the same procedure, and substituting the appropriate pyridine precursor, the following are obtained:

| Y | Z | mp |
|---|---|---|
| H | CH₃CH—<br>\|<br>OCOCH₃ | oil |
| CH₃ | CH₃COOCH₂ | oil |
| H | CH₃COOCH₂ | oil |

EXAMPLE 21

Preparation of methyl 6-hydroxymethyl-2-(4-isopropyl-4-methyl-5-oxo-2-imidazolin-2-yl)nicotinate

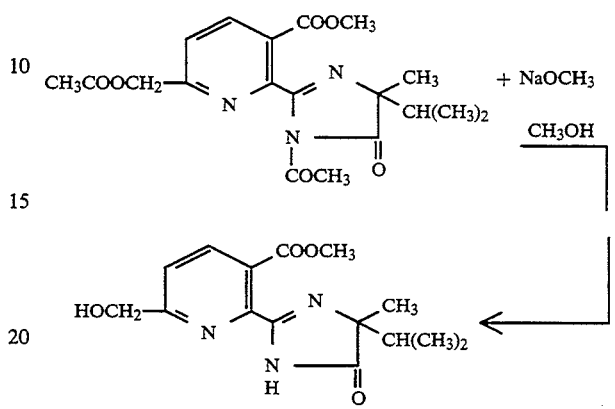

A solution of 16.7 g of methyl 6-acetoxymethyl-2-(1-acetyl-4-isopropyl-4-methyl-5-oxo-2-imidazolin-2-yl)nicotinate in 125 mL methanol containing 0.7 g of sodium methoxide is stirred at room temperature for 16 hours. The solution is adjusted to pH 5 with acetic acid and concentrated in vacuo. The residue is chromatographed on silica gel using ether-methanol as eluant to give the desired product as a solid. Recrystallization from methylene chloride-hexane gives analytically pure material, mp 115°–118° C.

Using essentially the same procedure, and substituting the appropriate pyridine precursor, and alkoxide nucleophile the following are obtained:

| Y | Z | mp |
|---|---|---|
| H | CH₃CH—<br>\|<br>OH | oil |
| CH₃ | HOCH₂— | oil |
| H | HOCH₂— | oil |

EXAMPLE 22

Preparation of methyl 6-chloromethyl-2-(4-isopropyl-4-methyl-5-oxo-2-imidazolin-2-yl)nicotinate

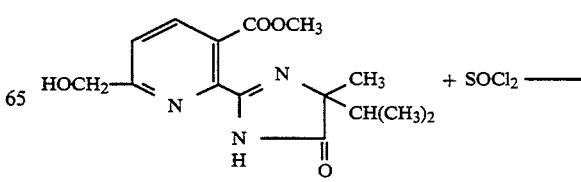

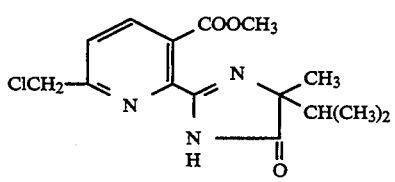

To a solution of 8.7 g of methyl 6-hydroxymethyl-2-(4-isopropyl-4-methyl-5-oxo-2-imidazolin-2-yl)nicotinate in 90 mL chloroform, stirred at room temperature, is added dropwise 4.2 mL of thionyl chloride. When the addition is complete, the solution is heated at reflux for 1 hour. The reaction is concentrated in vacuo, and the residue is dissolved in methylene chloride and washed with saturated sodium bicarbonate solution. The organic phase is dried and concentrated in vacuo to an oil. Trituration of this oil affords the desired product as a solid. Recrystallization from methylene chloride-hexane gives analytically pure material, mp 127°–129° C.

EXAMPLE 23

Preparation of methyl 2-(4-isopropyl-4-methyl-5-oxo-2-imidazolin-2-yl)-6-methylthiomethylnicotinate

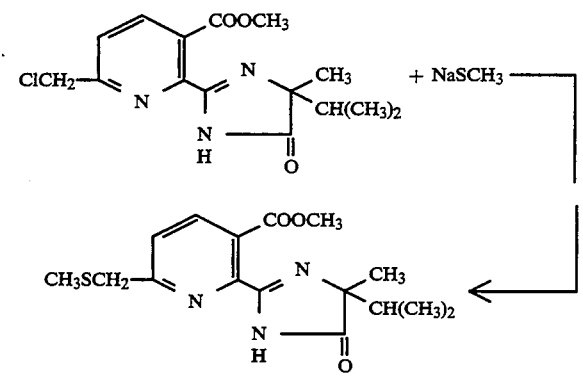

To 30 mL of absolute methanol, stirred at −10° under nitrogen, is added in portions 0.9 g of 50% sodium hydride (oil dispersion). A stream of methyl mercaptan is then added to the solution until a pH of 10 is achieved. To this solution is added 3 g of methyl 6-chloromethyl-2-(4-isopropyl-4-methyl-5-oxo-2-imidazolin-2-yl)nicotinate, and stirring is continued at −10° for 1 hour. The reaction is then allowed to warm to room temperature over 1 hour, and is then acidified with glacial acetic acid to pH 4. The mixture is concentrated in vacuo, and the residue is dissolved in methylene chloride, washed with saturated aqueous sodium bicarbonate, dried, and concentrated in vacuo. The residue is dissolved in absolute methanol, washed with hexanes, and concentrated in vacuo to afford the desired product. Recrystallization from methylene chloride-hexane affords a solid, mp 113.5°–115° C.

EXAMPLE 24

Preparation of 1-dimethylamino-1-(2-furyl)ethylene

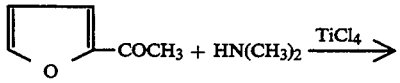

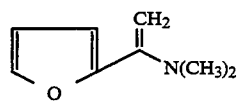

To a solution of 55 g of 2-acetylfuran and 193 g of dimethylamine in 1 liter of dry benzene, stirred at 3° under nitrogen, is added dropwise a solution of 31 mL of titanium tetrachloride in 100 mL benzene over 45 minutes. The mixture is stirred for a further 3 hours at 3°, then at ambient temperature overnight. The brown reaction mixture is filtered through a medium frit glass funnel under nitrogen, and the filtered solids are washed with dry benzene. The combined filtrates are concentrated in vacuo to give the desired enamine as an oil.

EXAMPLE 25

Preparation of 1-morpholino-2-(2-thienyl)ethylene

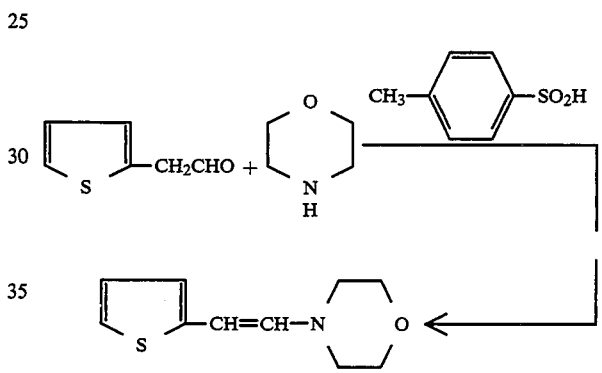

A mixture of 1.5 g of 2-thienylacetaldehyde, 1.4 mL of morpholine, and 0.012 g of p-toluenesulfonic acid hydrate in 7.5 mL of toluene is heated at reflux under a Dean-Stark Trap with azeotropic removal of water for 3 hours. The solution is cooled, neutralized by the addition of solid sodium methoxide, and concentrated in vacuo. The residue is taken up in toluene, filtered, and concentrated in vacuo to afford the desired enamine as an oil.

Using the same procedure, 1-morpholino-2-(3-thienyl)ethylene and 1-morpholino-2-cyclohexylethylene are prepared.

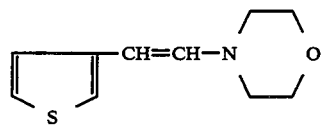

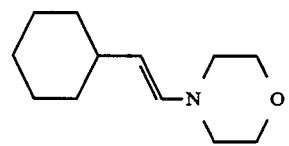

EXAMPLE 26

Preparation of diethyl 6-(2-furyl)pyridine-2,3-dicarboxylate

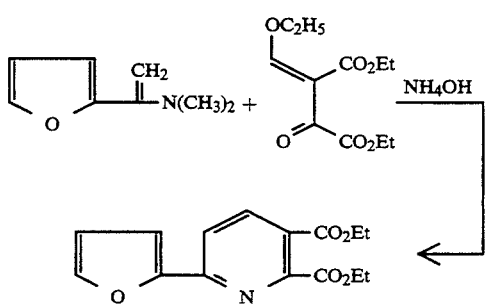

A solution of 147 g of diethyl ethoxymethyleneoxalacetate in 600 mL of absolute ethanol is stirred at 5° C. while a solution of 68.8 g of 1-dimethylamino-1-(2-furyl)ethylene in 400 mL of absolute ethanol is added dropwise over 1 hour. After stirring for an additional 2 hours, the reaction mixture is treated with 250 mL of concentrated aqueous ammonium hydroxide. The resulting mixture is stirred at ambient temperature overnight and then concentrated in vacuo. Chromatography of the residue on silica gel using chloroform as eluant affords the desired product.

Using essentially the same procedure, and substituting the appropriate enamine, the following are prepared:

![structure]

| Y | Z | mp |
|---|---|---|
| ⟨S⟩ (2-thienyl) | H | Solid |
| H | ⟨S⟩ (2-thienyl) | 97–99° |
| ⟨S⟩ (2-thienyl) | H | 64–66° |
| CH₃CO | H | oil |
| (CH₃)₃C—OCO | CH₃ | oil |
| CH₃CO | CH₃ | oil |
| cyclohexyl | H | oil |
| CH₃ | CH₃ | oil |
| H | CH₃ | oil |

EXAMPLE 27

Preparation of 6-hydroxy-2-(4-isopropyl-4-methyl-5-oxo-2-imidazolin-2-yl)nicotinic acid

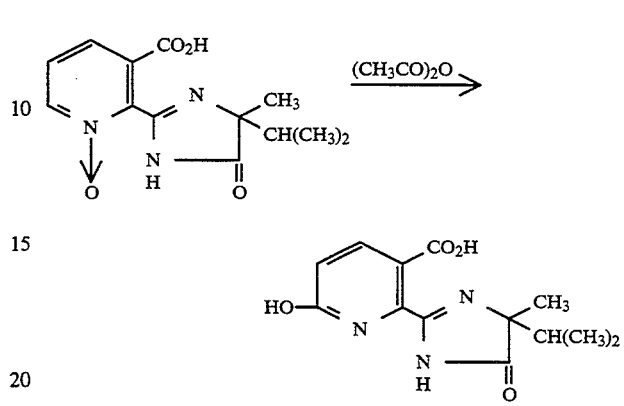

A mixture of 3 g of 2-(4-isopropyl-4-methyl-5-oxo-2-imidazolin-2-yl)nicotinic acid -1-oxide, 2.24 g of acetic anhydride, and 0.4 g of pyridine in 80 mL of toluene is stirred and heated at reflux for 3 hours. The reaction mixture is cooled to 10° C. and 75 mL of cold water is added with vigorous stirring. The resulting yellow solid is filtered, washed with toluene, and air dried. Recrystallization of this solid from methanol affords the desired product as a white solid, mp 201°–203° C.

EXAMPLE 28

Preparation of diethyl pyridine-2,3-dicarboxylate-N-oxide

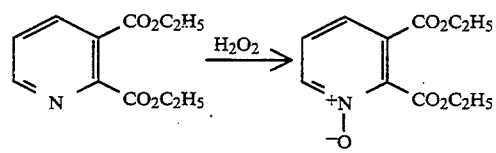

A mixture of 99 g of diethyl pyridine-2,3-dicarboxylate, 7.2 mL of concentrated sulfuric acid, 85 mL of 30% hydrogen peroxide and 256 mL acetic acid is stirred and heated at 85° for 4 hours. The reaction is concentrated in vacuo, and the residue is dissolved in methylene chloride, and washed with water, then saturated sodium bicarbonate. After drying, the organic phase is concentrated in vacuo to afford 79 g of the desired product, mp 80°–85°. A portion recrystallized from carbon tetrachloride-pentane has mp 87°–88°.

Using essentially the same procedure, and substituting the appropriate pyridine precursor, and optionally using meta-chloroperoxybenzoic acid in place of hydrogen peroxide, one obtains the following:

![structure]

| Y | Z | mp |
|---|---|---|

| -continued | | |
|---|---|---|
| CH₃ | CH₃ | solid |
| H | CH₃ | solid |

EXAMPLE 29

Preparation of diethyl 6-chloropyridine-2,3-dicarboxylate

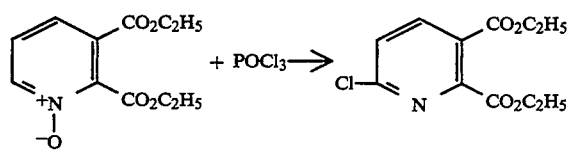

A mixture of 75.6 g of diethyl pyridine-2,3-dicarboxylate-N-oxide and 150 mL of phosphorous oxychloride is warmed slowly in a large reaction vessel equipped with a reflux condenser and gas scrubber. Caution: exothermic reaction! At about 70°, an exothermic reaction ensues with vigorous liberation of hydrogen chloride gas. The reaction is heated at reflux after the exotherm subsides for an additional hour. The reaction is cooled and concentrated in vacuo to a syrup. This material is dissolved in methylene chloride, washed cautiously with saturated sodium bicarbonate, dried and concentrated in vacuo to give the desired product as an oil. An analytical sample is obtained by chromatography on silica gel using 2:1 petroleum ether-ether as eluant to give the product as a colorless oil.

EXAMPLE 30

Preparation of 6-hydroxypyridine-2,3-dicarboxylic acid

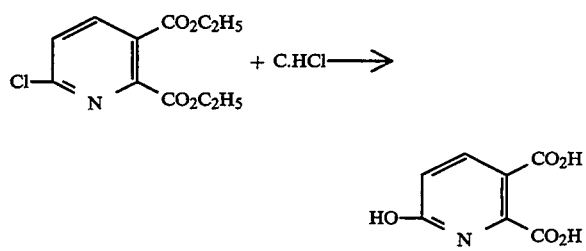

A mixture of 72 g of diethyl 6-chloropyridine-2,3-dicarboxylate and 420 mL of concentrated hydrochloric acid is stirred and heated at reflux overnight. The reaction mixture is cooled, and the solid is filtered and washed with hot water to give the desired product as a solid.

EXAMPLE 31

Preparation of 6-H-pyrrolo[3,4-b]pyridine-6-acetonitrile, 5,7-dihydro-2-hydroxy-α-isopropyl-α-methyl-5,7-dioxo-, acetate (ester)

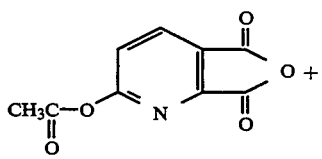

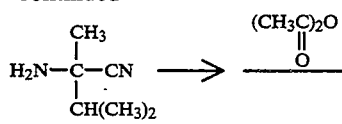

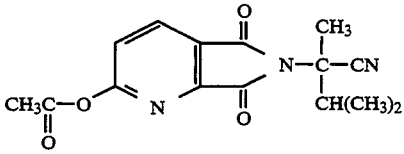

A mixture of 30 g of crude 6-acetoxypyridine-2,3-dicarboxylic anhydride and 21 g of 2-amino-2,3-dimethylbutyronitrile in 100 mL of methylene chloride is stirred at room temperature (exotherm) for 15 minutes, then at reflux for an additional 5 minutes. The solvent is removed in vacuo, and the residue is mixed with 15 g sodium acetate and 300 mL of acetic anhydride and heated at reflux for 35 minutes. The reaction mixture is cooled and filter chromatographed through 200 g of silica gel, using additional amounts of dilute methanol in ethyl acetate as eluant. The combined filtrates are concentrated in vacuo to give the desired product as an oil. A portion can be crystallized from carbon tetrachloride-pentane to give an analytically pure solid, mp 104.5°-108°.

EXAMPLE 32

Preparation of 6H-pyrrolo[3,4-b]pyridine-6-acetamide, 5,7-dihydro-2-hydroxy-α-isopropyl-α-methyl-5,7-dioxo

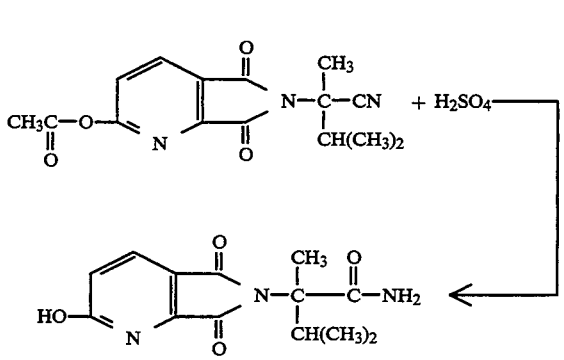

To a suspension of 34.5 g of 5,7-dihydro-2-hydroxy-α-isopropyl-α-methyl-5,7-dioxo-6e,uns/H/ -pyrrolo[3,4-e,uns/b/ ]pyridine-6-acetonitrile, acetate(ester) in 150 mL ethylene dichloride, stirred in an ice bath, is added slowly 110 g of concentrated sulfuric acid. The resulting mixture is heated at 60° for 3 hours, cooled to room temperature, mixed with 100 g of sodium acetate, and poured onto ice-water with efficient stirring. Filtration and washing the filtered solid with water affords the desired product. A portion can be recrystallized from dimethylsulfoxide-water to give an analytically pure sample, mp 211°-212°.

EXAMPLE 33

Preparation of methyl 6-hydroxy-2-(4-isopropyl-4-methyl-5-oxo-2-imidazolin-2-yl)nicotinate

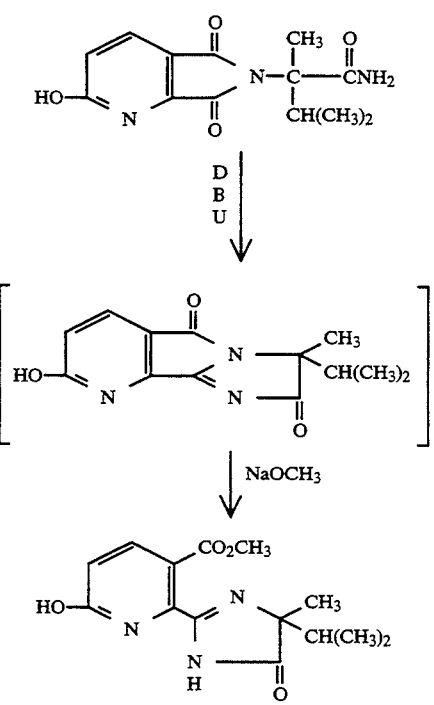

A mixture of 15 g of 5,7-dihydro-2-hydroxy-α-isopropyl-α-methyl-5,7-dioxo-6H-pyrrolo[3,4-b]pyridine-6-acetamide and 600 mL xylene is heated at reflux under a water separator, and 2.46 g of DBU is added in three portions over 20 minutes. After heating at reflux for an additional 45 minutes, the reaction is cooled to 100° and filtered through a sintered-glass funnel. The filtrate is treated with a solution of 6 g sodium methoxide in 25 mL methanol and allowed to stand at room temperature overnight. The xylene layer is decanted off, and the residual yellow oil is dissolved in acetic acid and filtered through 50 g of silica gel using additional 4:1 ethyl acetate-methanol as eluant. The combined filtrates are concentrated in vacuo and reevaporated from xylenes to give the desired product as a solid. A portion can be triturated with 50% aqueous methanol, filtered, washed with ether, and dried to give a solid, mp 186°–191°.

EXAMPLE 34

Preparation of 2-(4-isopropyl-4-methyl-5-oxo-2-imidazolin-2-yl)-6-(2-thienyl)nicotinic acid, isopropylamine salt

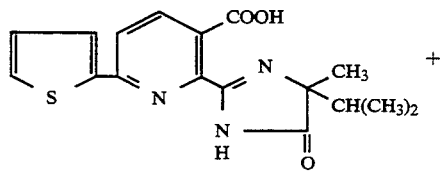

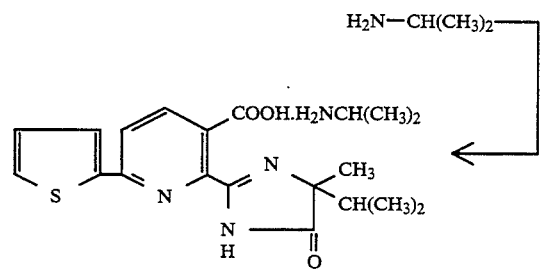

A solution of 2 g of 2-(4-isopropyl-4-methyl-5-oxo-2-imidazolin-2-yl)-6-(2-thienyl)nicotinic acid and 0.34 g isopropyl amine in 20 mL tetrahydrofuran is stirred at room temperature for 10 minutes. The reaction is diluted with 4 mL of hexane, filtered, and the filtrate is stirred overnight. The solid is filtered, washed with tetrahydrofuran, and dried in vacuo to give the desired product as a solid, mp 247°–257°(dec).

Also prepared by this method is the isopropylamine salt of the 6-(furyl)nicotinic acid.

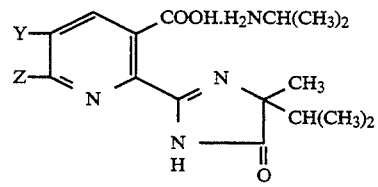

| Y | Z | mp |
|---|---|---|
| H | 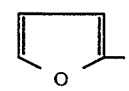 | 241–256° (dec) |

EXAMPLE 35

Preparation of methyl 2-(4-isopropyl-4-methyl-5-oxo-2-imidazolidinyl)-5-propenylnicotinate, cis and trans

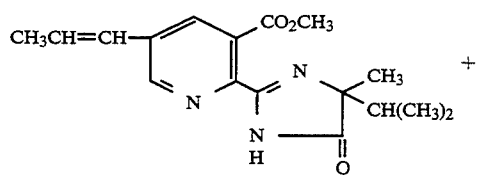

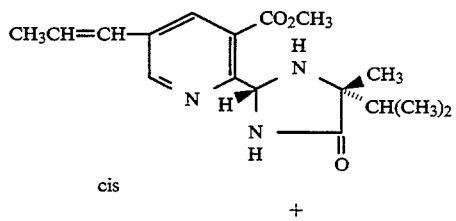

cis

+

-continued

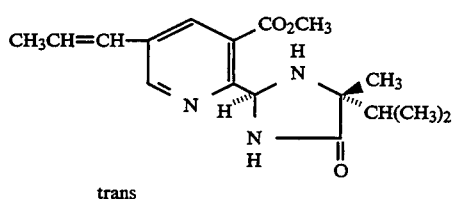

trans

A solution of 2.0 g of methyl 2-(4-isopropyl-4-methyl-5-oxo-2-imidazolin-2-yl)-5-propenylnicotinate in 50 mL of absolute methanol is cooled in an ice bath to 2° and the pH is adjusted to 3 with dilute methanolic hydrogen chloride. Sodium cyanoborohydride is added in small portions, with maintenance of the pH at 3 by concurrent addition of dilute methanolic hydrogen chloride, until the disappearance of the starting material is indicated by TLC. The reaction mixture is concentrated in vacuo, and the residue is chromatographed on silica gel using hexane-ethyl acetate mixtures as eluant to give the cis and trans products as solids.

EXAMPLE 36

Preparation of 5-(3-hydroxy-3-methyl-1-butynyl)-2-(4-isopropyl-4-methyl-5-oxo-2-imidazolin-2-yl)nicotinic acid, methyl ester

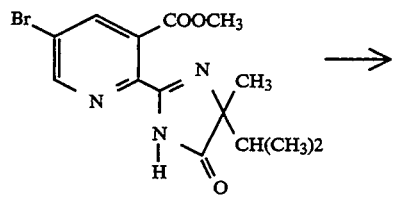

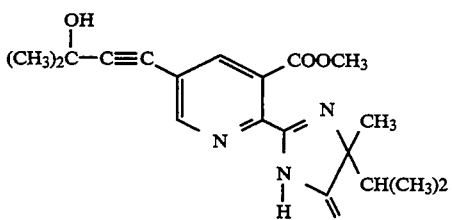

A stirred mixture of 12.6 g of 5-bromo-2-(4-isopropyl-4-methyl-5-oxo-2-imidazolin-2-yl)nicotinic acid, methyl ester, 3.4 g of 3-hydroxy-3-methyl-1-butyne, 0.02 g of bis(triphenylphosphine)palladium(II)-chloride, 0.04 g of triphenylphosphine, and 0.02 g of cuprous iodide in 300 mL of dry triethylamine is heated at reflux for 72 hours. The reaction is then filtered hot through celite, and the filtering agent is washed with methylene chloride. The combined filtrates were concentrated in vacuo, and the residue is partitioned between dilute aqueous hydrochloric acid and methylene chloride. The organic phase is washed with brine, dried, concentrated in vacuo, and the residue is chromatographed on silica gel using ether-methylene chloride mixtures to afford the desired product, mp 142°-145°.

EXAMPLE 37

Preparation of 5-ethynyl-2-(4-isopropyl-4-methyl-5-oxo-2-imidazolin-2-yl)nicotinic acid

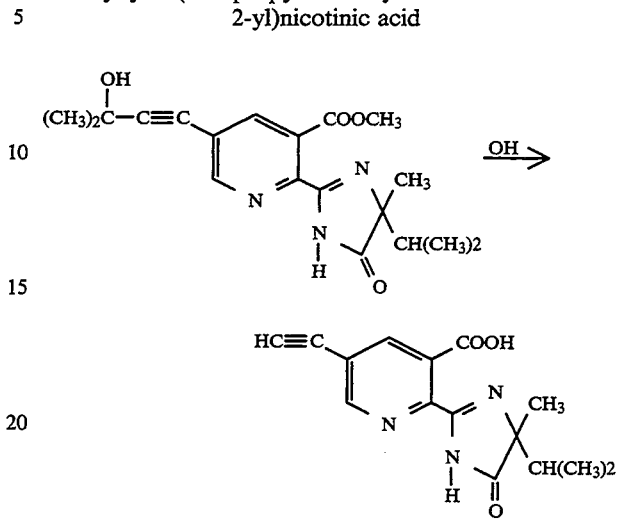

A solution of 1.5 g of 5-(3-hydroxy-3-methyl-1-butynyl)-2-(4-isopropyl-4-methyl-5-oxo-2-imidazolin-2-yl)nicotinic acid, methyl ester, and 0.185 g of sodium hydroxide in 12 mL water is heated at reflux for 2½ hours, then stirred at room temperature overnight. The reaction is then cooled to 10°, acidified to pH 3 with concentrated hydrochloric acid and extracted with methylene chloride. The organic phase is dried and concentrated in vacuo to afford the crude, desired product. An analytical sample, purified via its methyl ester, had mp 190°-195°.

EXAMPLE 38

Preparation of 5-(1-propynyl)-pyridine-2,3-dicarboxylic acid, diethyl ester

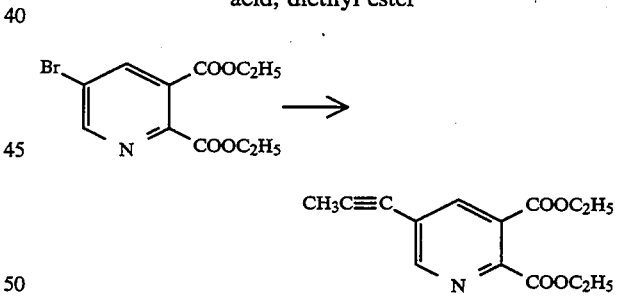

A stirred mixture of 3 g of 5-bromo-pyridine-2,3-dicarboxylic acid, diethyl ester, 0.1 g cuprous iodide and 0.7 g bis(triphenylphosphine)palladium(II)chloride in 40 mL dimethyl sulfoxide and 12 mL triethylamine is cooled to 10°, and 10 mL of liquid propyne is added. The reaction is stirred at room temperature thereafter for 16 hours, then is poured onto water and extracted with methylene chloride. The organic phase is washed with dilute hydrochloric acid, then water, then brine, and dried. Concentration in vacuo, and chromatography of the residue on silica gel using ether-hexane mixture affords the desired product as an oil.

EXAMPLE 39

Preparation of 2-(4-isopropyl-4-methyl-5-oxo-2-imidazolin-2-yl)-5-[(phenylsulfinyl)methyl]nicotinic acid, methyl ester

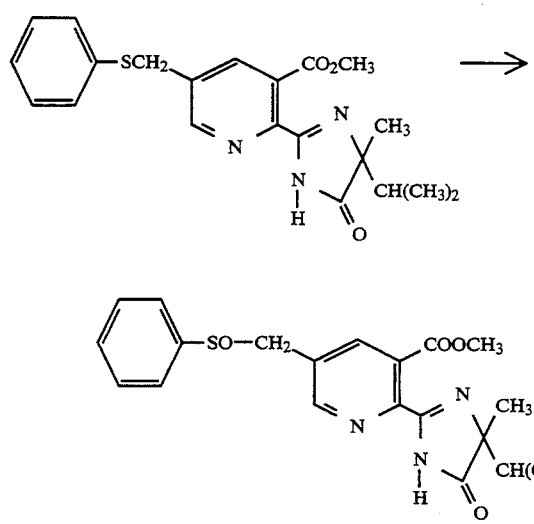

To a solution of 1.0 g of 2-(4-isopropyl-4-methyl-5-oxo-2-imidazolin-2 -yl)-5-[(phenylthio)methyl]nicotinic acid, methyl ester, in 20 mL methylene chloride is added 0.2 g sodium bicarbonate. The stirred mixture is cooled to −78° C. under nitrogen, and a solution of 0.51 g meta-chloroperoxybenzoic acid in 20 mL methylene chloride is added in one portion. The reaction mixture is stirred at −78° C. for 30 minutes, allowed to warm to room temperature over 1 hour, then stirred overnight. The reaction is poured onto 5% aqueous sodium bisulfite, and the organic phase is separated, washed with aqueous sodium bicarbonate, dried over magnesium sulfate and concentrated in vacuo. The residue is chromatographed on silica gel using hexane-ethylacetate mixtures to afford the desired product, mp 132°–136°.

By optionally using an excess of meta-chloroperbenzoic acid in the above procedure, optionally hydrolyzing the ester subsequent to the oxidation, and using the appropriate nicotinate precursor, one obtains the following:

| Y | R | mp °C. |
|---|---|---|
| C6H5SO2CH2— | CH3 | 68–77 |
| CH3SOCH2— | H | 190–192 |
| CH3SO2CH2— | H | oil |
| (CH3)2CHSOCH2— | H | solid |
| C6H5CH2SO2CH2— | H | 140–143 |

EXAMPLE 40

Preparation of 2-(1-benzoyl-4-isopropyl-4-methyl-5-oxo-2-imidazolin-2 yl)-5-[(phenylsulfonyl)methyl]nicotinic acid, methyl ester

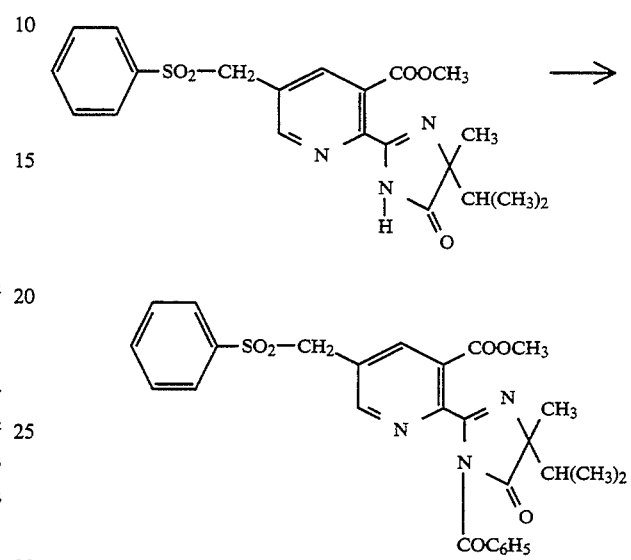

A solution of 5.9 g of 2-(4-isopropyl-4-methyl-5-oxo-2-imidazolin-2-yl)-5 -[(phenylsulfonyl)methyl]nicotinic acid, methyl ester, and 0.3 g p-dimethylaminopyridine in 50 mL pyridine is stirred at room temperature and 1.75 mL benzoyl chloride is added in one portion. After stirring overnight, the reaction is concentrated in vacuo and the residue is partitioned between methylene chloride and aqueous sodium bicarbonate. The aqueous phase is further extracted with methylene chloride, and the combined organic phases are dried and concentrated in vacuo. Chromatography of the residue on silica gel using hexane-ethyl acetate mixtures affords the desired product, mp 162°–166°.

Using essentially the same procedure, and substituting the appropriate pyridine precursor, one obtains the following:

| Y | Z | mp |
|---|---|---|
| CH3OCH2 | H | gum |
| CH3 | H | gum |
| C2H5 | H | gum |

EXAMPLE 41

Preparation of
5-(cyanomethyl)-2-(4-isopropyl-4-methyl-5-oxo-2-imidazolin-2-yl)nicotinic acid

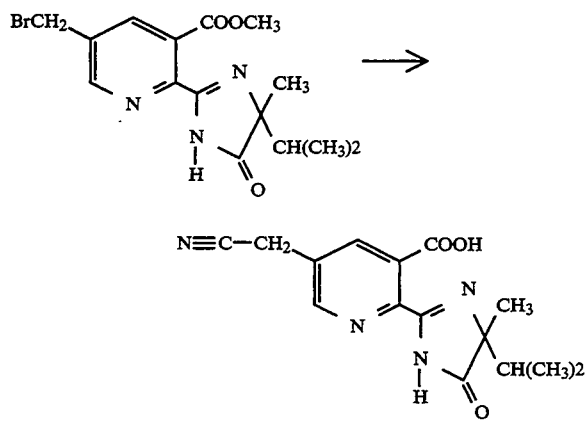

To a solution of 1.0 g of 2-(1-benzoyl-4-isopropyl-4-methyl-5-oxo-2-imidazolin-2-yl)-5-bromomethyl-nicotinic acid, methyl ester, in 60 mL ethanol is added 0.24 g sodium cyanide, followed by 10 cc water. The resulting solution is stirred at room temperature for 24 hours and concentrated in vacuo. The residue is partitioned between methylene chloride and water. The aqueous phase is acidified to pH 3 and extracted with methylene chloride, and the combined organic phases are dried and concentrated in vacuo. Chromatography of the residue on silica gel using methylene chloride-methanol mixtures affords the desired product, mp 196°–200° (dec).

EXAMPLE 42

Preparation of
5-cyclopropyl-2-(4-isopropyl-4-methyl-5-oxo-2-imidazolin-2yl)nicotinic acid

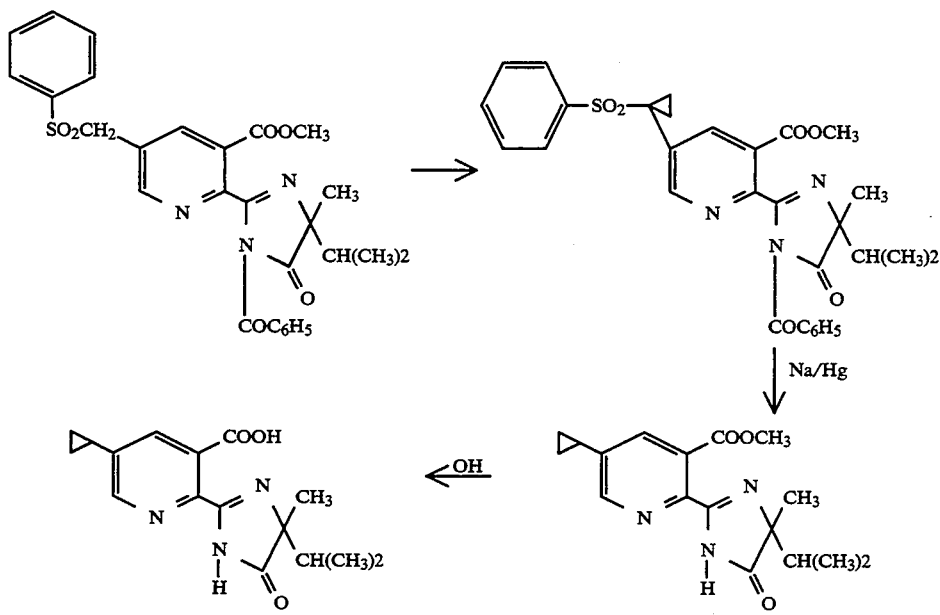

To a solution of 2.0 g potassium tert-butoxide in 10 mL dimethylformamide, stirred at −10° C., is added a solution of 2.38 g of 2-(1-benzoyl-4-isopropyl-4-methyl-5-oxo-2-imidazolin-2-yl)-5-[(phenylsulfonyl)methyl]-nicotinic acid, methyl ester, in 15 mL dimethylformamide. After stirring at −10° for an additional 20 minutes, 2.25 g of (2-chloroethyl)dimethylsulfonium iodide is added, and the reaction is stirred at −10° for 1.5 hours, then at 0° for 1 hour. The reaction mixture is quenched with 2 g of ammonium chloride and concentrated in vacuo. The residue is partitioned between methylene chloride and aqueous ammonium chloride, and the organic phase is dried and concentrated in vacuo. The residue is chromatographed on silica gel using hexane-ethyl acetate mixtures to afford a mixture of benzoylated and non-benzoylated 2-(4-isopropyl-4-methyl-5-oxo-2-imidazolin-2-yl)-5-[(1-phenylsulfonyl)-1-cyclopropyl]nicotinic acid, methyl esters.

This mixture is re-benzoylated according to Example 40 to afford 2-(1-benzoyl-4-isopropyl-4-methyl-5-oxo-2-imidazolin-2-yl)-5-[(1-phenylsulfonyl)-1-cyclopropyl]-nicotinic acid, methyl ester as a gum.

To a solution of 0.3 g of this material in 3 mL methanol containing 0.69 g disodiumhydrogen phosphate is added at 0°. 1.84 g of solid 6% sodium-mercury amalgam. The reaction mixture is stirred at 0° for 6.5 hours, then diluted with 100 mL aqueous ammonium chloride and extracted with methylene chloride. The combined extracts were dried and concentrated in vacuo to afford crude 5-cyclopropyl-2-(4-isopropyl-4-methyl-5-oxo-2-imidazolin-2yl)nicotinic acid, methyl ester. Hydrolysis of this material according to Example 9 and chromatography of the residue on silica gel using methylene chloride-methanol mixtures affords the desired product, mp 157°–163°.

EXAMPLE 43

Preparation of
5-(dimethoxymethyl)-2-(4-isopropyl-4-methyl-5-oxo-2-imidazolin-2-yl)nicotinic acid, methyl ester, and
2-(4-isopropyl-4-methyl-5-oxo-2-imidazolin-2-yl)-6-methoxy-5-(methoxymethyl)nicotinic acid, methyl ester

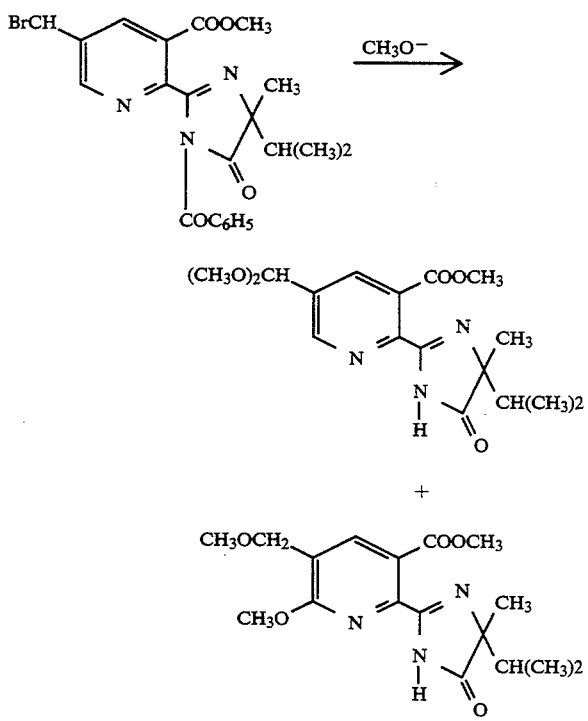

To a solution of 0.50 g of 5-(dibromomethyl)-2-(1-benzoyl-4-isopropyl-4-methyl-5-oxo-2-imidazolin-2-yl)nicotinic acid, methyl ester, in 10 mL methanol is added 0.20 g sodium methoxide, and the reaction is heated at reflux for 5 hours. The reaction is then cooled, concentrated in vacuo, and the residue is digested in aqueous ammonium chloride and extracted with methylene chloride. The combined extracts are dried, concentrated in vacuo, and the residue is chromatographed on silica gel using hexane-ethyl acetate mixtures to afford 0.15 g of 5-(dimethoxymethyl)-2-(4-isopropyl-4-methyl-5-oxo-2-imidazolin-2-yl)nicotinic acid, methyl ester, as a colorless oil, and 0.07 g of 2-(4-isopropyl-4-methyl-5-oxo-2-imidazolin-2 -yl)-6-methoxy-5-(methoxymethyl)-nicotinic acid, methyl ester as a white solid.

EXAMPLE 44

Preparation of
5-chloromethyl-2,3-pyridinedicarboxylic acid anhydride

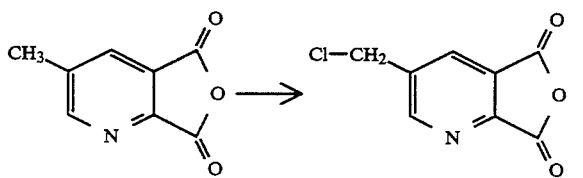

A solution of 75.0 g (0.41 m) of 5-methyl-2,3-pyridinedicarboxylic acid in 500 mL of 1,2-dimethoxyethane is treated with 125 g acetic anhydride (1.2 m) and 81 g pyridine (1.02 m). The resulting solution is stirred for 18 hours at room temperature. The solution is stripped in vacuo to leave 70.3 g (100%) of 5-methyl-2,3-pyridinedicarboxylic acid anhydride. The anhydride is dissolved in 500 mL $CCl_4$ and is treated with 1 g AIBN and 240 g (150 mL, 1.8 m) $SO_2Cl_2$ at room temperature. The solution is heated to reflux for 2 hours. An additional 1.0 g AIBN and 80 g (50 mL 0.6 m) $SO_2Cl_2$ are added and refluxing continued for an additional 2 hours. The solution, with some suspended solids, is cooled to 15° in an icebath and filtered to leave 56.0 g (69%) of a yellow solid: 5-chloromethyl-2,3-pyridinedicarboxylic anhydride (78% by nmr) mp (softens at 90° C.) 141°–145° C. Alternatively, the product can be hydrolyzed to give 5-chloromethyl-2,3-pyridinedicarboxylic acid, mp 170°–172°, from which the anhydride can be reformed by standard methods (see Example 6).

EXAMPLE 45

Preparation of
2-[(1-carbamoyl-1,2-dimethylpropyl)carbamoyl]-5-(chloromethyl)nicotinic acid, triethylamine salt

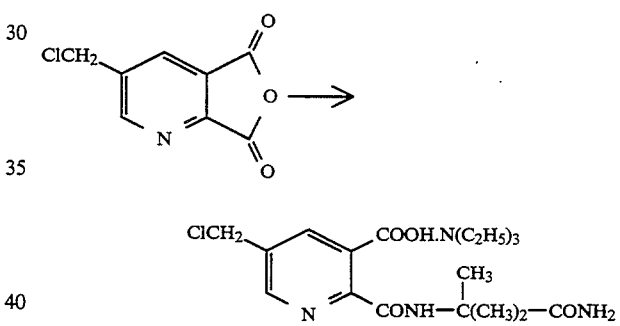

A solution of 5-(chloromethyl)-2,3-pyridinedicarboxylic acid anhydride [72.0 g (78% real) 0.3 m] in 300 mL $CH_3CN$ is cooled in an ice-salt bath to 0°. A solution of 39.0 g (0.3 m) α-methylvaleramide and 33.4 g (0.33 m) triethylamine in 100 mL $CH_3CN$ is added with stirring over 30 minutes with temperature ≦10°. The resulting suspension is stirred for an additional hour and filtered. The white solid is washed with 100 mL $Et_2O$ and is dried. There is obtained 83.2 g (66%) of 2-[(1-carbamoyl-1,2-dimethylpropyl)carbamoyl]-5-chloromethylnicotinic acid, triethylamine salt, mp (shrinks at 148°) 159°–160°.

EXAMPLE 46

Preparation of
5-methoxymethyl-2-(4-isopropyl-4-methyl-5-oxo-2-imidazolin-2 yl)nicotinic acid, triethylamine salt

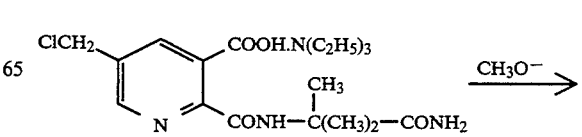

-continued

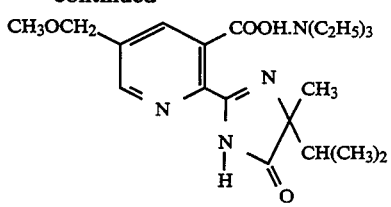

A solution of 41.0 g (0.096 m) of 2-[(1-carbamoyl-1,2-dimethylpropyl)carbamoyl]-5-chloromethylnicotinic acid, triethylamine salt in 250 mL absolute methanol is treated with 26.0 g (0.48 m) solid sodium methoxide. The resulting suspension is heated to reflux and held there for 2 hours. The reaction mixture is cooled to room temperature, and the pH is adjusted to 4 with concentrated hydrochloric acid and is filtered. The filtrate is evaporated in vacuo to leave 37.7 g (96%) of 2-(4-isopropyl-4-methyl-5-oxo-2-imidazolin-2-yl)-5-methoxymethylnicotinic acid, triethylamine salt as a yellow solid, mp 78°–80° C.

Using essentially the same procedure and substituting the appropriate nucleophile, and acidifying to pH 2 in the final workup so as to obtain the free acid directly, the following are obtained:

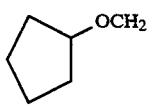

| Y | mp |
|---|---|
| $CH_2=CHCH_2OCH_2$ | 147.0–149.0° |
| $CH_3-CH(C_2H_5)OCH_2$ | 142.0–144.0° |
| $CH\equiv C-CH_2OCH_2$ | 125.0–128.0° |
| $CH_3(CH_2)_3OCH_2$ | 139.0–141.0° |
| $CH_3CH_2OCH_2$ | 160.0–162.0° |
| $CH_3OCH_2CH_2OCH_2$ | 115.0–116.0° |
| $CF_3CH_2OCH_2$ | 201.0–203.0° |
| $CH_3(CH_2)_2OCH_2$ | 159.0–160.5° |
| 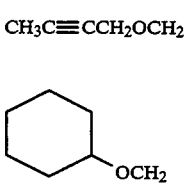 —$CH_2OCH_2$ (cyclopropyl) | 141.5–143.0° |
| $(CH_3)_2CHOCH_2$ | 167.0–169.0° |
| $CH_2=CH(CH_2)_2OCH_2$ | 146.0–148.0° |
| $FCH_2CH_2OCH_2$ | 146.0–148.0° |
| 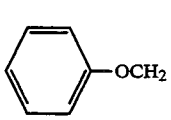 (tetrahydrofuran-3-yl-OCH_2) | 129.0–132.0° |
| (thiophen-2-yl)-$CH_2OCH_2$ | — |
| $Cl_3CCH_2OCH_2$ | 186.0–188.0° |
| (phenyl)-$CH_2OCH_2$ | 168.0–169.0° |
| $(CH_3)_2CHCH_2OCH_2$ | 172.0–174.0° |

-continued

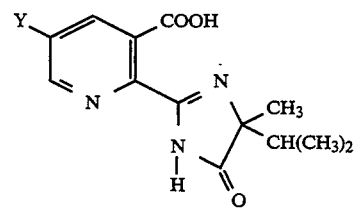

| Y | mp |
|---|---|
| (cyclopentyl)-$OCH_2$ | 142.0–143.0° |
| $CH_3C\equiv CCH_2OCH_2$ | 144.5–146.0° |
| (cyclohexyl)-$OCH_2$ | 153.5–154.5° |
| (phenyl)-$OCH_2$ | 208.5–209.5° |

EXAMPLE 47

Preparation of 2-(4-isopropyl-4-methyl-5-oxo-2-imidazolin-2yl)-5-(methoxylmethyl)nicotinic acid

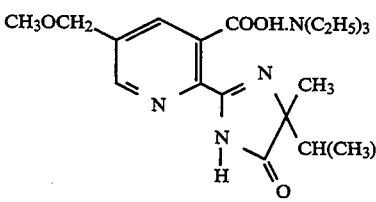

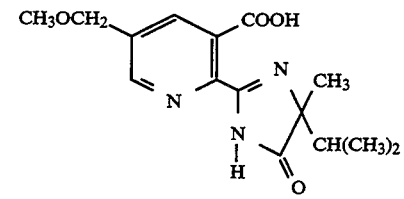

A solution of 2-(4-isopropyl-4-methyl-5-oxo-2-imidazolin-2yl)-5-(methoxylmethyl)nicotinic acid, triethylamine salt (37.7 g, 0.09 m) in 100 mL $H_2O$ is cooled in an ice bath and the pH adjusted to pH 1 to 2 with concentrated hydrochloric acid. The resultant white solid is filtered to give 22.5 g (82%) of 2-(4-isopropyl-4-methyl-5-oxo-2-imidazolin-2yl)-5-(methoxymethyl)-nicotinic acid, mp 158°–160° C.

EXAMPLE 48

Preparation of 5-(dimethylaminomethyl)-2-(4-isopropyl-4-methyl-5-oxo-2-imidazolin-2-yl)nicotinic acid

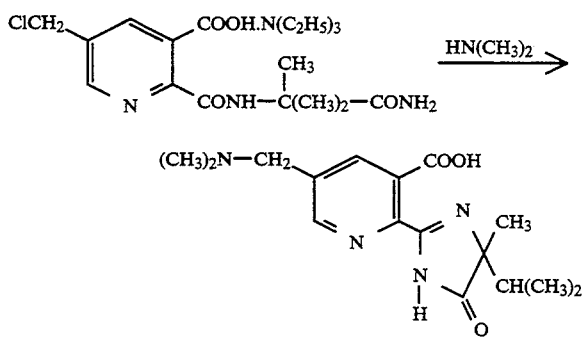

The triethylamine salt of 2-[(1-carbamoyl-1,2-dimethylpropyl)carbamoyl]-5-(chloromethyl)nicotinic acid (5.0 g, 0.012 mole) is dissolved in 40% aqueous dimethylamine (13.5 mL, 0.120 mole) stirred at 30° for 2 hours, and concentrated in vacuo to give 5.1 g of a yellow oil. A portion of this oil (3.94 g, 0.010 mole) is dissolved in 10 mL 5N NaOH, stirred at 60° for 4 hours, cooled to room temperature, treated with 75 mL water, and acidified to pH 4 with concentrated hydrochloric acid. The water is removed in vacuo; the residue is taken up in ethanol, filtered, and concentrated in vacuo. The procedure is repeated; the final residue is dissolved in 50 mL water, and the solution is washed with methylene chloride and evaporated to dryness to give the product as a white solid, 0.34 g, mp 186°–190°.

Using essentially the same procedure, and substituting the appropriate nucleophile, the following are obtained:

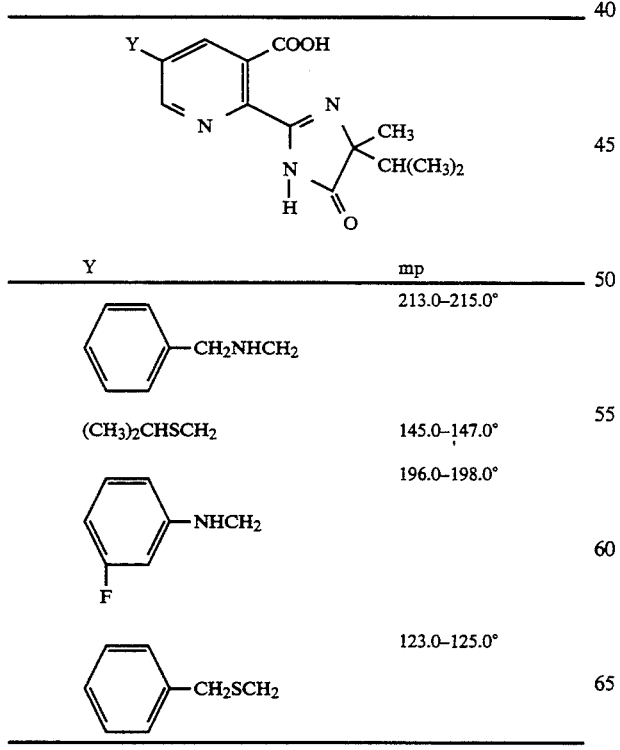

| Y | mp |
|---|---|
| ⟨phenyl⟩—CH₂NHCH₂ | 213.0–215.0° |
| (CH₃)₂CHSCH₂ | 145.0–147.0° |
| ⟨phenyl⟩—NHCH₂ | 196.0–198.0° |
| ⟨F-phenyl⟩—NHCH₂ | |
| ⟨phenyl⟩—CH₂SCH₂ | 123.0–125.0° |

EXAMPLE 49

Preparation of 5-(1-methoxyethyl)-2-(4-isopropyl-4-methyl-5-oxo-2-imidazolin-2yl)nicotinic acid, methyl ester

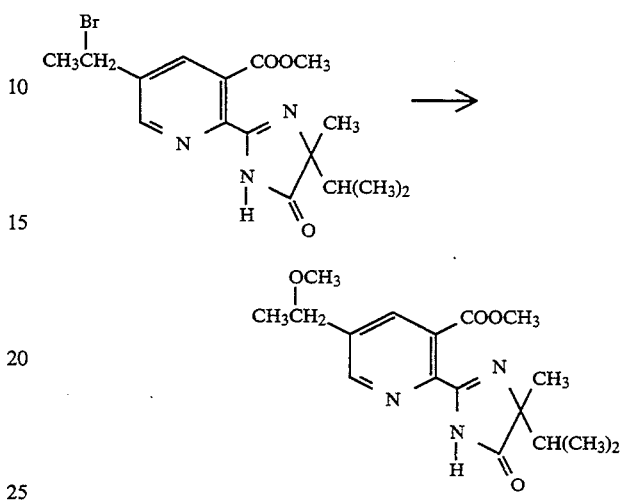

A solution of 5-(1-bromoethyl)-2-(4-isopropyl-4-methyl-5-oxo-2-imidazolin-2yl)nicotinic acid, methyl ester (9.2 g, 0.024 mole) in absolute methanol (400 mL) is heated in a sealed pressure vessel at 120°–140° for 18 hours. The solution is cooled and then stirred with NaHCO₃ (2.0 g, 0.024 mole) for 1 hour. The mixture is filtered, and the filtrate is concentrated to leave a gum which is chromatographed twice on silica with ether as eluant to afford 1.52 g of the product, a glass, which is dissolved in CCl₄. The solution is filtered to remove impurities and concentrated to leave the desired product, a glass, which still contained some CCl₄.

EXAMPLE 50

Preparation of diethyl 5-(1-hydroxyethyl)-6-methylpyridine-2,3-dicarboxylate

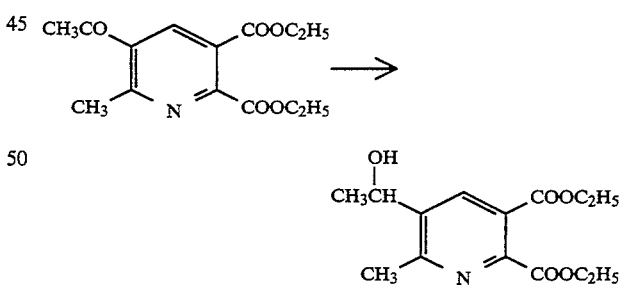

A solution of the starting material (55.8 g, 0.020 mole) in absolute ethanol (140 mL) is added slowly to a cold (8°) solution of NaBH₄ (2.91 g, 0.0767 mole) in absolute ethanol (200 mL). The cooling bath is then removed, and the solution is kept at 22° for 16 hours. The solution is then cooled to 8° and acidified to pH 2 with concentrated hydrochloric acid (ca. 8 mL). After a short time, the solution is treated with water (30 mL) and Na₂CO₃ (20 g, 0.2 mole) and then filtered. The filtrate is concentrated to an oil which is dissolved in ether. The dried (MgSO₄) solution is in turn concentrated to leave the product, 57.2 g of an amber oil, (98.5% purity).

EXAMPLE 51

Preparation of diethyl 5-(1-bromoethyl)-6-methyl-2,3-pyridinedicarboxylate

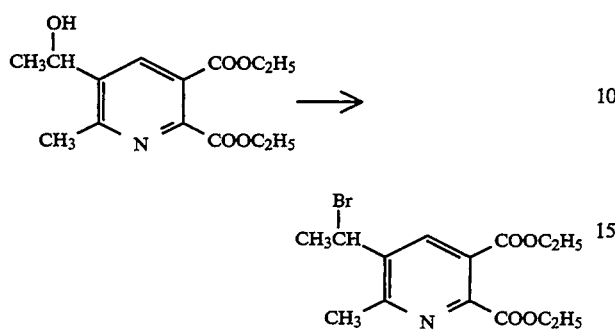

Phosphorous tribromide (7.0 mL, 0.074 mole) is added dropwise over 3 minutes to a solution of the 5-(1-hydroxyethyl)-6-ethyl diester (52.0 g, 0.185 mole) in dry dimethoxyethane (500 mL). The temperature rises from 22° to 33°. The mixture is stirred for 21 hours at 22° and then is basified to pH 6 by the addition of water (50 mL) and NaHCO₃ (50 g). The organic layer is separated, washed with two 30 mL portions of aqueous NaHCO₃ solution, dried (MgSO₄), and concentrated to leave the 5-(1-bromoethyl-6-methyl diester, a yellow oil, wt. 54.3 g, (91.4% purity).

EXAMPLE 52

Preparation of diethyl 5-(1-methoxymethyl)-6-methyl-2,3-pyridinedicarboxylate

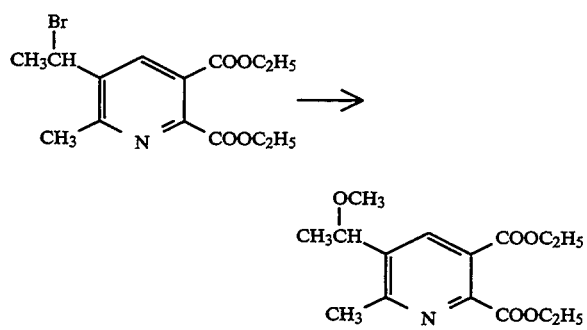

A solution of the 5-(1-bromoethyl)diester (51 g, 0.148 mole) in methanol (500 mL) is heated at 120° in a sealed vessel for 28 hours. After cooling to room temperature, NaHCO₃ (12.5 g, 0.15 mole) is added; the mixture is stirred, filtered, and the filtrate is concentrated in vacuo. The residue is dissolved in ether, treated with water and solid NaHCO₃ (12.5 g). The mixture is stirred, and the phases are separated. The aqueous layer is extracted with four portions of ether; the organic phases are combined and washed with aqueous NaHCO₃ solution, dried (MgSO₄) and concentrated to leave 11.1 g of the product as a dark oil.

EXAMPLE 53

Preparation of 5-acetyl-6-methylpyridinedicarboxylic acid diethyl ester, oxime

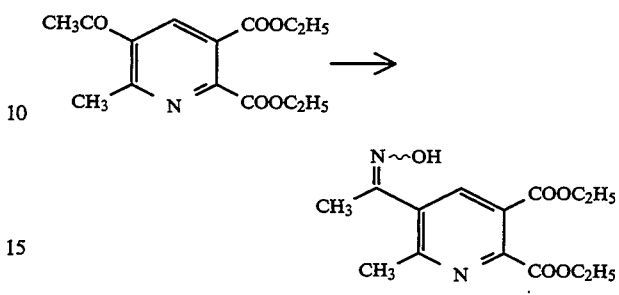

The starting material, 5-acetyl-6-methylpyridinediethyl ester, (59.5 g, 0.213 mol) is dissolved in 590 mL of absolute ethanol. Hydroxylamine hydrochloride (16.3 g, 1.1 equivalents) and sodium acetate (19.2 g, 1.1 equivalents) are added, and the mixture is mechanically stirred for 24 hours. The precipitate is filtered, and the filter cake is washed with 100 mL of absolute ethanol. The filtrates are combined and concentrated in vacuo to yield 62.0 g of a yellow oil.

Using essentially the same procedure and the appropriate pyridine precursor, one obtains the following:

$$\text{structure with Y, Z substituents on pyridine with two } CO_2C_2H_5 \text{ groups}$$

| Y | Z | mp |
|---|---|---|
| $\begin{matrix} N-OH \\ \parallel \\ CH_3-C- \end{matrix}$ | H | oil |

EXAMPLE 54

Preparation of 5-acetamido-pyridine-2,3-dicarboxylic acid, diethyl ester

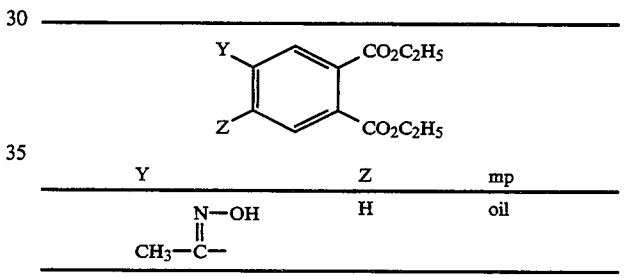

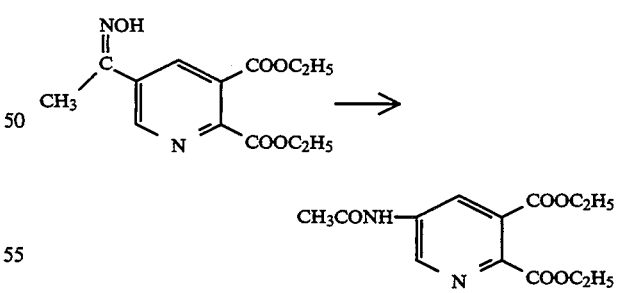

A stirred solution of 14 g of 5-acetylpyridine-2,3-dicarboxylic acid, diethyl ester, oxime, in 350 mL of dry tetrahydrofuran is treated with 15.6 g of phosphorous pentachloride in portions over a 20-minute period. The resulting dark reaction mixture is stirred at room temperature for 4 days, cooled in an ice bath, and quenched by the dropwise addition of 125 mL of saturated aqueous sodium bicarbonate. The aqueous phase is extracted with ethyl acetate, and the combined organic phases are washed with brine, dried, and concentrated in vacuo. The residue is dissolved in methylene chloride, washed with saturated bicarbonate, followed by water. Drying and concentration in vacuo affords a gum which is chromatographed on silica gel using ether-ethyl acetate mixtures to afford the desired product, mp 108°-110°.

Using essentially the same procedure and substituting the appropriate pyridine precursor, one obtains the following:

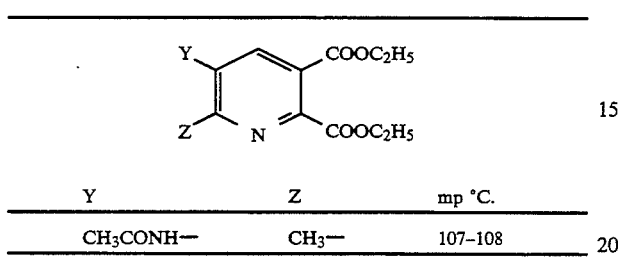

| Y | Z | mp °C. |
|---|---|---|
| CH₃CONH— | CH₃— | 107-108 |

EXAMPLE 55

Preparation of 5-formyl-2-(4-isopropyl-4-methyl-5-oxo-2-imidazolin-2-yl)nicotinic acid, methyl ester

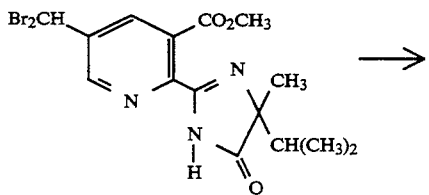

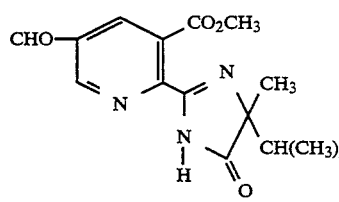

A stirred solution of 1.38 g of 2-(1-benzoyl-4-isopropyl-4-methyl-5-oxo-2-imidazolin-2-yl)-5-(dibromomethyl)nicotinic acid, methyl ester, in 35 mL tetrahydrofuran is cooled to −78° and treated with a mixture of 0.3 mL of N-ethylethylenediamine, 10 mL tetrahydrofuran, and 0.8 mL of triethylamine. After warming to room temperature, the reaction solution is treated with 0.3 mL of N-ethylethylenediamine, stirred for 2 hours, heated at reflux for 24 hours, and concentrated in vacuo. The residue is partitioned between methylene chloride and water; the aqueous phase is further extracted with methylene chloride, and the combined organic phases are dried and concentrated in vacuo. Chromatography of the residue on silica gel using hexane-ethyl acetate mixtures affords the desired product, mp 113°-117°.

EXAMPLE 56

Preparation of 5-carboxy-6-(4-isopropyl-4-methyl-5-oxo-2-imidazolin-2-yl)-2-methyl-3-pyridinecarbamic acid, dimethyl ester

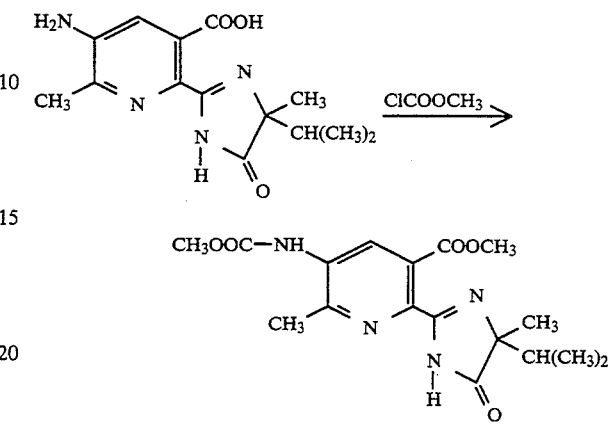

To a stirred solution of 5-amino-6-methyl-2-(4-isopropyl-4-methyl-5-oxo-2-imidazolin-2yl)nicotinic acid (5.0 g, 17.2 mmole) and pyridine (2.8 mL, 34.4 mole) in 50 mL of dry dimethoxyethane is added methylchloroformate (2.7 mL, 34.4 mmole). The reaction is heated at reflux for 3 hours, then held at 50° for 16 hours. After cooling to room temperature, the reaction mixture is treated with 15 mL of methanol, basified to pH 7-8 with sodium methoxide, stirred at room temperature for 16 hours, and concentrated in vacuo. The residue is chromatographed using heptane-ethyl acetate mixtures to provide the product in 28% yield as a white solid, 1.75 g, mp 184°-186°.

EXAMPLE 57

Preparation of 2-chloro-3-(2-chloroethyl)-5,8-dimethoxyquinoline

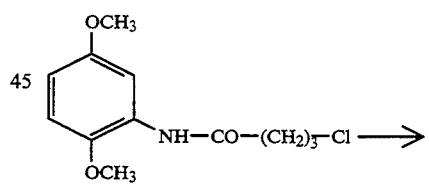

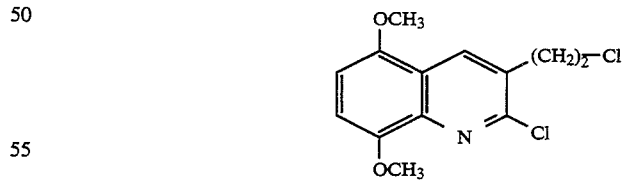

A solution of 2,5-dimethoxy-N-(4-chlorobutyroyl)aniline (164 g, 0.64 mole) in 300 mL of phosphorous oxychloride is cooled to 5° and 60 mL of dimethylformamide is added in portions over a 30-minute period. The solution is heated at 100° for 2½ hours, cooled, and concentrated in vacuo. The residue is poured into 2 L of ice water with stirring, and basified to pH 9 with ammonium hydroxide with ice cooling. Extraction of the reaction mixture with methylene chloride, drying, and concentration in vacuo affords the desired product, mp 108°-109.5°.

EXAMPLE 58

Preparation of 6-chloro-5-(2-chloroethyl)pyridine-2,3-dicarboxylic acid, dimethyl ester

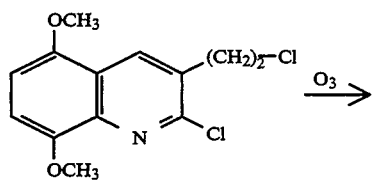

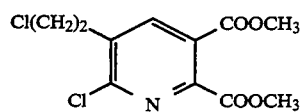

A solution of 2-chloro-3-(2-chloroethyl)-5,8-dimethoxyquinoline (22.0 g, 0.077 mole) in 1 L methanol containing 80 mL of trimethylorthoformate and 2 mL concentrated sulfuric acid is stirred at room temperature while ozone is bubbled in until TLC indicates the disappearance of starting material. The reaction is concentrated in vacuo, and the residue is partitioned between ether and saturated aqueous bicarbonate. The organic layer is washed further with bicarbonate, then with aqueous bisulfite. Drying and concentration in vacuo affords the desired product as an oil.

EXAMPLE 59

Preparation of 5-(2-chloroethyl)-pyridinedicarboxylic acid, dimethyl ester

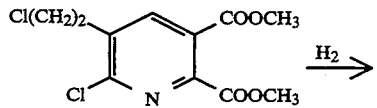

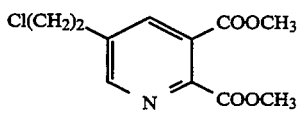

A mixture of 18 g of 6-chloro-5-(2-chloroethyl)pyridine-2,3-dicarboxylic acid, dimethyl ester, 1 g of 10% palladium on carbon, and 7 g of sodium acetate in 100 mL methanol is shaken in a hydrogenation apparatus under 15 psi for 23 hours. The reaction is then filtered through celite, and the catalyst is washed with a little methanol. The combined filtrates are concentrated in vacuo, and the residue is partitioned between methylene chloride and water. The organic phase is washed with saturated bicarbonate, dried, and concentrated in vacuo. The residue is chromatographed on silica gel using hexane-ethyl acetate mixtures to afford 8.9 g of the desired product as an oil.

EXAMPLE 60

Preparation of 5-vinyl-2,3-pyridinedicarboxylic acid, dimethyl ester

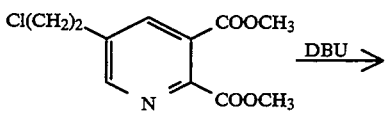

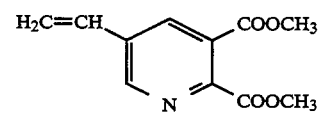

A solution of 2 g of 5-(2-chloroethyl)-pyridine-2,3-dicarboxylic acid, dimethyl ester and 0.13 mL diazobicycloundecane (DBU) in 40 mL of toluene is heated at reflux for 1½ hours, cooled, and filtered. The filtrate is concentrated in vacuo, and the residue is chromatographed on silica gel using hexane-ethyl acetate mixtures to afford the desired product as a colorless oil.

EXAMPLE 61

Preparation of 6-methyl-5-(N-methylacetamido)-pyridine-2,3-dicarboxylic acid, diethyl ester

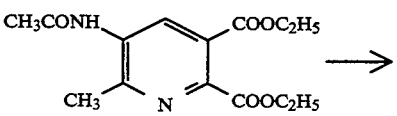

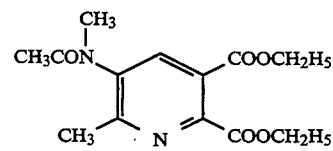

A stirred mixture of 2.94 g of 5-acetamido-6-methylpyridine-2,3-dicarboxylic acid, diethyl ester, and 0.44 g of 60% sodium hydride in 200 mL dry tetrahydrofuran is kept at room temperature for 1 hour, then 0.93 mL of methyl iodide is added, and the reaction is stirred for an additional 4 hours. The reaction is concentrated in vacuo, and the residue is slurried in water, the pH is adjusted to 3 with hydrochloric acid, and the mixture is extracted with methylenechloride. The organic phase is dried, concentrated in vacuo to afford the desired product as an oil.

Using essentially the same procedure, and substituting the appropriate acetamido- or hydroxyalkylpyridine precursor, one obtains the following:

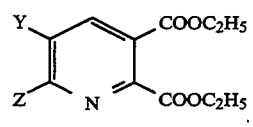

| Y | Z | mp |
|---|---|---|
| $CH_3$ | $CH_3OCH_2-$ | oil |
| H | $CH_3OCH_2-$ | oil |
| H | $CH_3CH(OCH_3)-$ | oil |

EXAMPLE 62

Preparation of 6-methyl-5-methylamino-pyridine-2,3-dicarboxylic acid, diethyl ester

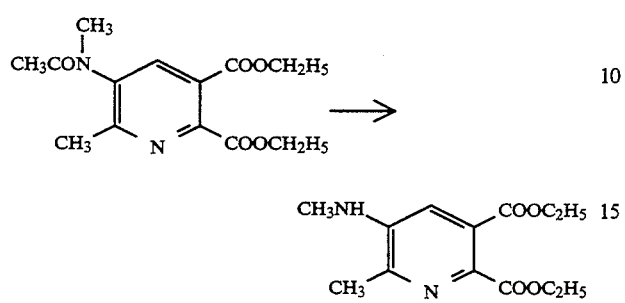

A solution of 90.6 g of 6-methyl-5-(N-methylacetamido)-pyridine-2,3-dicarboxylic acid, diethyl ester in 700 mL absolute ethanol is treated with 60 mL of concentrated hydrochloric acid, and the solution is heated at reflux for 17 hours. The reaction is cooled, 75 mL of concentrated hydrochloric acid is added, and the reaction is heated at reflux for another 8 hours. The solution is concentrated in vacuo; the residue is stirred in water and basified to pH 8 using a saturated bicarbonate solution. The mixture is then extracted with methylene chloride, and the extracts are dried and concentrated in vacuo to afford the desired product as an oil.

EXAMPLE 63

Preparation of 6-methyl-5-(N-methylmethanesulfonylamino)-pyridine-2,3-dicarboxylic acid, diethyl ester

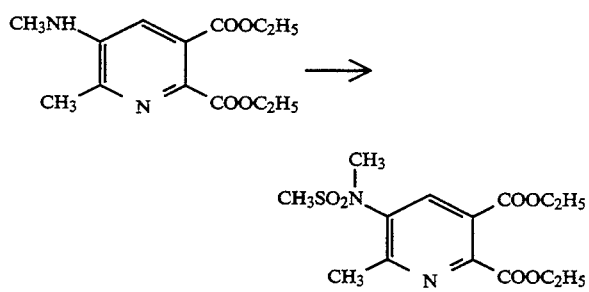

A solution of 1.33 g of 6-methyl-5-(N-methylamino)-pyridine-2,3-dicarboxylic acid, diethyl ester, in 30 mL dry tetrahydrofuran is cooled under nitrogen with stirring to −65° C., and treated dropwise with 2.6 mL of 2.3M n-butyllithium (hexane solution). When the addition is complete, 0.4 mL of methanesulfonyl chloride is added, and the reaction is allowed to warm to room temperature over a 30 minute period. The reaction is quenched with 10 mL of water and concentrated in vacuo. The residue is partitioned between methylene chloride and water, and the organic layer is dried and concentrated in vacuo. This residue is chromatographed on silica gel using ether to afford the desired product, mp 90°–93° C.

EXAMPLE 64

Preparation of 6-methyl-2,3,5-pyridinetricarboxylic acid, 2,3-diethyl ester

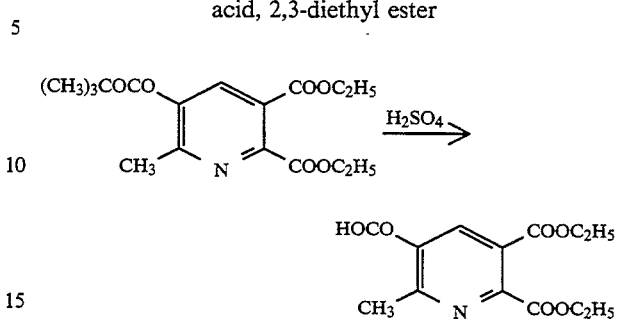

To 350 mL of concentrated sulfuric acid, cooled to 15° with mechanical stirring, is added 320 g of the starting material dropwise over a 70 minute period. The addition funnel is rinsed with ether, and the ether is added to the reaction mixture, which is allowed to stir at room temperature for three days. The reaction is poured onto an ether-ice mixture with efficient stirring, basified to pH 9 with concentrated ammonium hydroxide, and separated. The aqueous phase is acidified to pH 2 with concentrated hydrochloric acid and extracted with ethyl acetate. Drying and concentration in vacuo of the ethylacetate phase affords 231 g of the desired product as a low melting solid.

EXAMPLE 65

Preparation of 5-(hydroxymethyl)-6-methylpyridine-2,3-dicarboxylic acid, diethyl ester

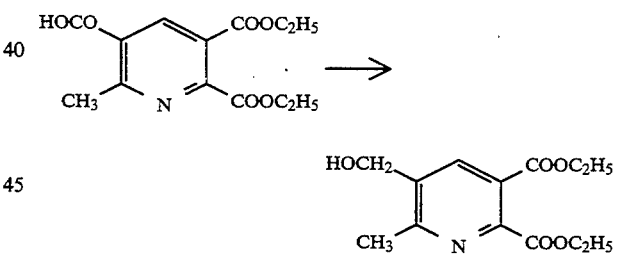

A solution of 464 g 6-methyl-2,3,5-pyridinetricarboxylic acid, 2,3-diethyl ester in 2.5 L toluene is cooled, under nitrogen, 5° with mechanical stirring while 200 mL of borane-dimethylsulfide complex is added dropwise over a one hour and 30 minute period. After stirring at room temperature for three days, the reaction is cooled to 10° and quenched with 250 mL of concentrated hydrochloric acid. A further 500 mL of 3M hydrochloric acid and 250 mL of ethyl acetate is added, and the reaction is vigorously stirred for three hours and 30 minutes. The organic layer can be filter chromatographed through silica gel and concentrated in vacuo to recover 96 g unreacted starting material. The aqueous layer is neutralized with 50% sodium hydroxide, extracted with ethyl acetate, concentrated in vacuo, and chromatographed on silica gel using hexane-ethyl acetate mixtures to afford 44 g of the desired product as an oil.

EXAMPLE 66

Preparation of
5-(methoxymethyl)-6-methylpyridine-2,3-dicarboxylic
acid, diethyl ester

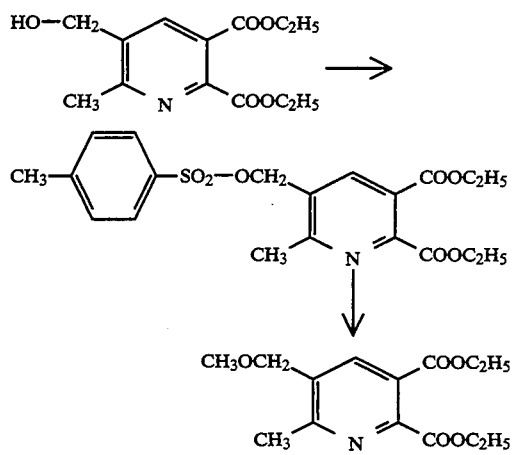

A solution of 5.0 g of 5-(hydroxymethyl)-6-methyl-pyridine-2,3-dicarboxylic acid, diethyl ester in 100 mL of methylene chloride is cooled to 0° and 20 mL of triethylamine and 4.0 g of p-toluenesulfonyl chloride is added. The reaction mixture is stirred at room temperature for 16 hours, filtered and concentrated in vacuo to afford the crude tosylate. This material is dissolved in 75 mL of methanol; 3.8 g of 60% sodium hydride is added in small portions, and the reaction is stirred at room temperature for 24 hours. Acidification and concentration in vacuo affords the crude product as a mixture of methyl and ethyl esters.

EXAMPLE 67

Preemergence Herbicidal Evaluation of Test Compounds

The preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.016 to 8.0 kg per hectare of test compound per cup. The treated cups are then placed in greenhouse benches, watered and cared for in accordance with conventional greenhouse procedures. From four to five weeks after treatment, the tests are terminated and each cup is examined and rated according to the rating system set forth below. Data obtained are reported in Table I below. Where more than one tests is involved for a given compound, the data are averaged.

Plant species employed in these evaluations are reported by header abbreviation, common name and scientific name.

Compounds employed in this preemergence herbicidal evaluation and in the post-emergence evaluation in the following example are given a compound number and identified by name. Data in Table I are reported by compound number.

*** Herbicide Rating Scale

Results of herbicide evaluation are expressed on a rating scale (0–9). The scale is based upon a visual observation of plant stand, vigor, malformation, size, chlorosis and overall plant appearance as compared with a control.

| RATING | MEANING | % Control (COMPARED TO CHECK) |
|---|---|---|
| 9 | Complete Kill | 100 |
| 8 | Approaching Complete Kill | 91–99 |
| 7 | Good Herbicidal Effect | 80–90 |
| 6 | Herbicidal Effect | 65–79 |
| 5 | Definite Injury | 45–64 |
| 4 | Injury | 30–44 |
| 3 | Moderate Effect | 16–29 |
| 2 | Slight Effect | 6–15 |
| 1 | Trace Effect | 1–5 |
| 0 | No Effect | 0 |
| P | "PGR" Effect | — |
| X | Unable to Read Sample | — |

| PLANT SPECIES EMPLOYED IN HERBICIDAL EVALUATIONS | | |
|---|---|---|
| HEADER ABB | COMMON NAME | SCIENTIFIC NAME |
| BARNYARDGR | BARNYARDGRASS | *ECHINOCHLOA CRUS-GALLI,* (L)BEAU |
| LARE CRAB | CRABGRASS, (HAIRY) LARGE | *DIGITARIA SANGUINALIS,* (L)SCOP |
| GREEN FOX | FOXTAIL, GREEN | *SETARIA VIRIDIS,* (L)BEAUV |
| P NUTSEDGE | NUTSEDGE, PURPLE | *CYPERUS ROTUNDUS,* L. |
| WILD OATS | OAT, WILD | *AVENA FATUA,* L. |
| QUACKGRASS | QUACKGRASS | *AGROPYRON REPENS,* (L)BEAUV. |
| FLD BINDWD | BINDWEED, FIELD (RHIZOME) | *CONVOLVULUS ARVENSIS,* L. |
| MATRICARIA | MATRICARIA | *MATRICARIA CHAMOMILLA,* L. |
| MRNGLRY SP | MORNINGGLORY SPP. | IPOMOEA SPP. |
| WILD MUSTD | MUSTARD, WILD | *BRASSICA KABER,* (DC)L.C. WHEELR |
| RAGWEED | RAGWEED, COMMON | *AMBROSIA ARTEMISIIFOLIA,* L. |
| PRIDY SIDA | SIDA, PRICKLY | *SIDA SPINOSA,* L. |
| VELVETLEAF | VELVETLEAF | *ABUTILON THEOPHRASTI,* MEDIC. |
| S BARLY LA | BARLEY, SPRING, LARKER | *HORDEUM VULGARE,* CV. LARKER |
| SUGARBEETS | SUGARBEETS | *BETA VULGARIS,* L. |
| CORN FIELD | CORN, FIELD | *ZEA MAYS,* L. |

| COMPOUNDS EVALUATED AS HERBICIDAL AGENTS | |
|---|---|
| Compound No. | |
| 1 | (E)-2-(4-isopropyl-4-methyl-5-oxo-2-imidazolin-2-yl)-5-styryl-nicotinic acid |
| 2 | (Z)-2-(4-isopropyl-4-methyl-5-oxo-2-imidazolin-2-yl)-5-styryl-nicotinic acid |
| 3 | methyl 5-isopropenyl-2-(4-isopropyl-4-methyl-5-oxo-2- |

COMPOUNDS EVALUATED AS HERBICIDAL AGENTS

| Compound No. | |
|---|---|
| | imidazolin-2-yl)nicotinate |
| 4 | 5-isopropenyl-2-(4-isopropyl-4-methyl-5-oxo-2-imidazolin-2-yl)nicotinic acid |
| 5 | 1,6-dihydro-2-(4-isopropyl-4-methyl-5-oxo-2-imidazolin-2-yl)-6-oxonicotinic acid |
| 6 | methyl 5-(1-hydroxyethyl)-2-(4-isopropyl-4-methyl-5-oxo-2-imidazolin-2-yl)nicotinate acetate (ester) |
| 7 | 5-acetyl-2-(4-isopropyl-4-methyl-5-oxo-2-imidazolin-2-yl)-6-methyl-nicotinic acid |
| 8 | 2-(4-isopropyl-4-methyl-5-oxo-2-imidazolin-2-yl)-6-(2-thienyl)nicotinic acid |
| 9 | methyl 5-acetyl-2-(4-isopropyl-4-methyl-5-oxo-2-imidazolin-2-yl)-6-methylnicotinate |
| 10 | isopropylammonium 2-(4-isopropyl-4-methyl-5-oxo-2-imidazolin-2-yl)-6-(2-thienyl)nicotinate |
| 11 | furfuryl 5-acetyl-2-(4-isopropyl-4-methyl-5-oxo-2-imidazolin-2-yl)-6-methylnicotinate |
| 12 | methyl 2-(4-isopropyl-4-methyl-5-oxo-2-imidazolin-2-yl)-6-(2-thienyl)nicotinate |
| 13 | 6-(2-furyl)-2-(4-isopropyl-4-methyl-5-oxo-2-imidazolin-2-yl)nicotinic acid |
| 14 | isopropylammonium 6-(2-furyl)-2-(4-isopropyl-4-methyl-5-oxo-2-imidazolin-2-yl)nicotinate |
| 15 | methyl 6-(2-furyl)-2-(4-isopropyl-4-methyl-5-oxo-2-imidazolin-2-yl)nicotinate |
| 16 | methyl 5-acetyl-2-(4-isopropyl-4-methyl-5-oxo-2-imidazolin-2-yl)nicotinate |
| 17 | 5-acetyl-2-(4-isopropyl-4-methyl-5-oxo-2-imidazolin-2-yl)nicotinic acid |
| 18 | methyl 2-(4-isopropyl-4-methyl-5-oxo-2-imidazolin-2-yl)-5-propenylnicotinate |
| 19 | (E)-2-(4-isopropyl-4-methyl-5-oxo-2-imidazolin-2-yl)-5-propenylnicotinic acid |
| 20 | 2-(4-isopropyl-4-methyl-5-oxo-2-imidazolin-2-yl)-5-(2-thienyl)nicotinic acid |
| 21 | 2-(4-isopropyl-4-methyl-5-oxo-2-imidazolin-2-yl)-5-[(methylthio)methyl]nicotinic acid |
| 22 | 2-(4-isopropyl-4-methyl-5-oxo-2-imidazolin-2-yl)-5-(3-thienyl)nicotinic acid |
| 23 | methyl 1,6-dihydro-2-(4-isopropyl-4-methyl-5-oxo-2-imidazolin-2-yl)-6-oxonicotinate |
| 24 | methyl 2-(4-isopropyl-4-methyl-5-oxo-2-imidazolin-2-yl)-6-[(methylthio)methyl]nicotinate |
| 25 | 2-(4-isopropyl-4-methyl-5-oxo-2-imidazolin-2-yl)-6-[(methylthio)methyl]nicotinic acid |

TABLE I

PRE-EMERGENCE TESTS - RATES IN KG/HA

| Compound No. | RATE | BARNY ARDGR | LARGE CRAB | GREEN FOX | P NUT SEDGE | WILD OATS | QUACK GRASS | FLD B INDWD | WRNGL RY SP | WILD MUSTD | RAGWE ED | PRIKY SIDA | VELVE TLEAF | MATRI CARIA | S BAR LY LA | SUGAR BEETS | CORN FIELD |
|---|---|---|---|---|---|---|---|---|---|---|---|---|---|---|---|---|---|
| 1 | 4.000 | 2.0 | | 0.0 | 0.0 | 0.0 | 0.0 | 9.0 | 3.0 | | 0.0 | | 3.0 | 3.0 | | 7.0 | 7.0 |
|   | 1.000 | 0.0 | | 0.0 | 0.0 | 0.0 | 0.0 | 7.0 | 0.0 | | 0.0 | | 0.0 | 3.0 | | 0.0 | 9.0 |
|   | .500 | 0.0 | | 0.0 | 0.0 | 0.0 | 0.0 | 0.0 | 0.0 | | 0.0 | | 0.0 | 0.0 | | 0.0 | 4.0 |
|   | .250 | 0.0 | | 0.0 | 0.0 | 0.0 | 0.0 | 2.0 | 0.0 | | 0.0 | | 0.0 | 0.0 | | 0.0 | 4.0 |
|   | .125 | 0.0 | | 0.0 | 0.0 | 0.0 | 0.0 | 0.0 | 0.0 | | 0.0 | | 0.0 | 0.0 | | 0.0 | |
|   | .063 | 0.0 | | 0.0 | 0.0 | 0.0 | 0.0 | 0.0 | 0.0 | | 0.0 | | 0.0 | 0.0 | | | |
| 2 | 4.000 | 2.0 | | 0.0 | 4.0 | 4.0 | 9.0 | 6.0 | 5.0 | | 2.0 | | 6.0 | 9.0 | | 0.0 | 2.0 |
|   | 1.000 | 1.0 | | 3.0 | 3.0 | 1.0 | 7.0 | 0.0 | 0.0 | | 0.0 | | 5.0 | 0.0 | | 7.0 | 1.0 |
| 3 | .500 | 0.0 | | 1.0 | 2.0 | 0.0 | 2.0 | 0.0 | 3.0 | | 0.0 | | 0.0 | 0.0 | | 6.0 | 1.0 |
|   | .500 | 0.0 | | 0.0 | 0.0 | 9.0 | 7.0 | 0.0 | 0.0 | | 3.0 | | 3.0 | 0.0 | | 0.0 | 9.0 |
|   | .250 | 5.0 | | 6.0 | 4.0 | 7.0 | 3.0 | 9.0 | 3.0 | | 2.0 | | 3.0 | 3.0 | | 8.0 | 9.0 |
|   | .125 | 1.0 | | 5.0 | 4.0 | 6.0 | 2.0 | 3.0 | 1.0 | | 1.0 | | 2.0 | 1.0 | | 7.0 | 5.0 |
|   | .063 | 0.0 | | 1.0 | 1.0 | 4.0 | 2.0 | 1.0 | 0.0 | | 0.0 | | 2.0 | 0.0 | | 4.0 | 3.0 |
|   | .032 | 0.0 | | 0.0 | 0.0 | 2.0 | 1.0 | 0.0 | 0.0 | | 0.0 | | 0.0 | 0.0 | | 3.0 | 2.0 |
|   | .016 | 0.0 | | 0.0 | 0.0 | 1.0 | 0.0 | 0.0 | 0.0 | | 0.0 | | 0.0 | 0.0 | | 2.0 | 1.0 |
| 4 | 8.000 | 9.0 | 9.0 | 9.0 | 9.0 | 9.0 | 9.0 | 9.0 | 8.0 | 9.0 | 9.0 | 9.0 | 9.0 | 9.0 | | 9.0 | 9.0 |
|   | .500 | 9.0 | | | 9.0 | 9.0 | 9.0 | 9.0 | 9.0 | | 9.0 | | 7.0 | 9.0 | | 8.0 | 9.0 |
|   | .250 | 8.0 | | | 8.0 | 8.0 | 6.0 | 9.0 | 7.0 | | 9.0 | | 7.0 | 7.0 | | 8.0 | 8.0 |
|   | .125 | 6.0 | | | 2.0 | 8.0 | 6.0 | 6.0 | 6.0 | | 9.0 | | 6.0 | 7.0 | | 8.0 | 7.0 |
|   | .063 | 6.0 | | | 2.0 | 6.0 | 4.0 | 7.0 | 4.0 | | 9.0 | | 4.0 | 7.0 | | 8.0 | 5.0 |
|   | .032 | 4.0 | | | 7.0 | 7.0 | 4.0 | 6.0 | 3.0 | | 9.0 | | 3.0 | 4.0 | | 8.0 | 5.0 |
|   | .016 | 3.0 | | | 2.0 | 5.0 | 4.0 | 6.0 | 1.0 | | 0.0 | | 2.0 | 0.0 | | 7.0 | 7.0 |
| 5 | .750 | 6.0 | | 7.0 | 9.0 | 9.0 | 9.0 | 9.0 | 7.0 | | 0.0 | 7.0 | 7.0 | 0.0 | | | 5.0 |
|   | .500 | 3.0 | | 5.0 | 8.5 | 2.0 | 8.5 | 9.0 | 5.5 | | 0.0 | 6.0 | 7.5 | 0.0 | | | 3.5 |
|   | .375 | 3.0 | | 4.0 | 8.0 | 0.0 | 7.0 | 8.0 | 4.0 | | 0.0 | 6.0 | 3.5 | 0.0 | | | 4.0 |
|   | .250 | 0.0 | | 0.0 | 4.5 | 1.0 | 4.0 | 4.0 | 0.0 | | 0.0 | 4.0 | 0.0 | 0.0 | | 9.0 | 0.5 |
|   | .188 | 0.0 | | 0.0 | 6.0 | 0.0 | 3.0 | 8.0 | 0.0 | | 0.0 | 0.0 | 0.0 | 0.0 | | | 0.0 |
|   | .125 | 0.0 | | 0.0 | 3.0 | 0.0 | 1.5 | 4.0 | 0.0 | | 0.0 | 0.0 | 0.5 | 0.0 | | | 0.5 |
|   | .063 | 0.0 | | 0.0 | 0.0 | 0.0 | 0.0 | 0.0 | 0.0 | | 0.0 | | 0.0 | 0.0 | | 1.0 | 0.0 |
|   | .032 | 0.0 | | 0.0 | 0.0 | 0.0 | 0.0 | 0.0 | 0.0 | | 0.0 | | 0.0 | 0.0 | | 0.0 | 0.0 |
|   | .016 | 0.0 | | 0.0 | 0.0 | 0.0 | 0.0 | 0.0 | 0.0 | | 0.0 | | 0.0 | 0.0 | | 0.0 | 0.0 |
| 6 | .500 | 9.0 | | | 8.0 | 9.0 | 9.0 | 8.0 | 8.0 | | 9.0 | | 3.0 | 0.0 | | 8.0 | 4.0 |
|   | .250 | 0.0 | | | 3.0 | 9.0 | 4.0 | 8.0 | 9.0 | | 0.0 | | 3.0 | 0.0 | | 0.0 | 0.0 |
|   | .125 | 0.0 | | | 0.0 | 9.0 | 2.0 | 4.0 | 9.0 | | 0.0 | | 0.0 | 0.0 | | 0.0 | 0.0 |
|   | .063 | 0.0 | | | 0.0 | 9.0 | 0.0 | 8.0 | 0.0 | | 0.0 | | 0.0 | 0.0 | | 0.0 | 0.0 |
|   | .032 | 0.0 | | | 0.0 | 9.0 | 0.0 | 7.0 | 1.0 | | 0.0 | | 0.0 | 0.0 | | 0.0 | 0.0 |
|   | .016 | 0.0 | | | 0.0 | 0.0 | 0.0 | 7.0 | 0.0 | | 0.0 | | 0.0 | 0.0 | | 0.0 | 0.0 |
| 7 | 8.000 | 9.0 | 9.0 | 9.0 | 9.0 | 9.0 | 9.0 | 9.0 | 8.0 | 9.0 | 9.0 | 9.0 | 9.0 | 0.0 | | 0.0 | 0.0 |
|   | .500 | 9.0 | | | 9.0 | 9.0 | 9.0 | 9.0 | 9.0 | | 9.0 | | 9.0 | 0.0 | | 8.0 | 0.0 |
|   | .250 | 8.0 | | | 9.0 | 9.0 | 9.0 | 9.0 | 9.0 | | 8.0 | | 8.0 | 0.0 | | 7.0 | 0.0 |
|   | .125 | 7.0 | | | 3.0 | 9.0 | 9.0 | 7.0 | 9.0 | | 8.0 | | 7.0 | 0.0 | | 7.0 | 0.0 |
|   | .063 | 2.0 | | | 0.0 | 9.0 | 0.0 | 7.0 | 8.0 | | 6.0 | | 8.0 | 0.0 | | 7.0 | 0.0 |
|   | .032 | 0.0 | | | 0.0 | 9.0 | 0.0 | | 6.0 | | 2.0 | | 5.0 | 0.0 | | 2.0 | 0.0 |
|   | .016 | 0.0 | | | 0.0 | 0.0 | 9.0 | 4.0 | 4.0 | | 0.0 | | 2.0 | 0.0 | | 0.0 | 0.0 |
| 8 | .500 | 3.0 | | | 7.0 | 5.0 | 4.0 | 3.0 | 5.5 | | 4.0 | | 2.0 | 0.0 | | 9.0 | 3.0 |
|   | .250 | 2.5 | | | 4.0 | 9.0 | 4.5 | 5.0 | 3.0 | | 0.0 | | 6.0 | 0.0 | | 9.0 | 0.0 |
|   | .125 | 0.0 | | | 3.0 | 0.0 | 2.0 | 1.0 | 3.0 | | 2.0 | | 6.0 | 4.5* | | 9.0 | 0.0 |
|   | .063 | 0.0 | | | 0.5 | 0.0 | 0.0 | 0.0 | 1.0 | | 0.0 | | 2.0 | 0.0 | | 5.5* | 0.0 |
|   | .032 | 0.0 | | | 0.0 | 0.0 | 0.0 | 0.0 | 0.0 | | 0.0 | | 0.5 | 0.0 | | 4.5* | 0.0 |
|   | .016 | 0.0 | | | 0.0 | 0.0 | 0.0 | 0.0 | 0.0 | | 0.0 | | 0.0 | 0.0 | | 2.0 | 0.0 |
|   |     |     |   |   |     |     |     |     |     |   | 0.0 |   | 0.0 | 0.0 |   | 1.0 | 0.0 |

TABLE I-continued

PRE-EMERGENCE TESTS - RATES IN KG/HA

| Compound No. | RATE | BARNY ARDGR | LARGE CRAB | GREEN FOX | P NUT SEDGE | WILD OATS | QUACK GRASS | FLD B INDWD | WRNGL RY SP | WILD MUSTD | RAGWEED | PRIKY SIDA | VELVE TLEAF | MATRI CARIA | S BAR LY LA | SUGAR BEETS | CORN FIELD |
|---|---|---|---|---|---|---|---|---|---|---|---|---|---|---|---|---|---|
| 9 | .500 | 7.0 | | | 0.0 | 9.0 | 9.0 | 9.0 | 6.0 | | 0.0 | | 7.0 | 0.0 | | 9.0 | 8.0 |
|  | .250 | 2.0 | | | 7.0 | 9.0 | 3.0 | 4.0 | 0.0 | | 0.0 | | 4.0 | 0.0 | | 7.0 | 6.0 |
|  | .125 | 0.0 | | | 6.0 | 7.0 | 1.0 | 2.0 | 0.0 | | 0.0 | | 1.0 | 0.0 | | | 3.0 |
|  | .063 | 0.0 | | | 2.0 | 2.0 | 0.0 | 0.0 | 0.0 | | 0.0 | | 0.0 | 0.0 | | 5.0 | 1.0 |
|  | .032 | 0.0 | | | 0.0 | 0.0 | 0.0 | 0.0 | 0.0 | | 0.0 | | 0.0 | 0.0 | | 0.0 | 0.0 |
| 10 | .500 | 9.0 | | | 6.0 | 0.0 | 5.0 | 9.0 | 6.0 | | 4.0 | | 7.0 | 4.0 | | 9.0 | 4.0 |
|  | .250 | 2.0 | | | 4.0 | 0.0 | 5.0 | 4.0 | 4.0 | | 2.0 | | 6.0 | 2.0 | | 6.0 | 2.0 |
|  | .125 | 0.0 | | | 4.0 | 0.0 | 3.0 | 1.0 | 2.0 | | 0.0 | | 5.0 | 1.0 | | 6.0 | 2.0 |
|  | .063 | 0.0 | | | 1.0 | 0.0 | 1.0 | 0.0 | 0.0 | | 0.0 | | 3.0 | 0.0 | | 2.0 | 0.0 |
|  | .032 | 0.0 | | | 0.0 | 0.0 | 0.0 | 0.0 | 0.0 | | 0.0 | | 1.0 | 0.0 | | | 0.0 |
| 11 | .500 | 9.0 | | | 9.0 | 9.0 | 9.0 | 9.0 | 9.0 | | 8.0 | | 8.0 | 9.0 | | 2.0 | 9.0 |
|  | .250 | 9.0 | | | 9.0 | 9.0 | 9.0 | 9.0 | 9.0 | | 7.0 | | 8.0 | 9.0 | | 9.0 | 9.0 |
|  | .125 | 2.0 | | | 9.0 | 9.0 | 9.0 | 9.0 | 8.0 | | 3.0 | | 7.0 | 4.0 | | 9.0 | 9.0 |
|  | .063 | 1.0 | | | 9.0 | 9.0 | 9.0 | 9.0 | 7.0 | | 1.0 | | 3.0 | 1.0 | | 9.0 | 9.0 |
|  | .032 | 0.0 | | | 7.0 | 7.0 | 8.0 | 3.0 | 3.0 | | 0.0 | | 3.0 | 0.0 | | 9.0 | 8.0 |
|  | .016 | 0.0 | | | 4.0 | 2.0 | 2.0 | 0.0 | 0.0 | | 0.0 | | 0.0 | 0.0 | | 7.0 | 7.0 |
| 12 | .500 | 0.0 | | | 0.0 | 0.0 | 0.0 | 0.0 | 0.0 | | 0.0 | | 0.0 | 0.0 | | 7.0 | 3.0 |
|  | .250 | 0.0 | | | 0.0 | 0.0 | 0.0 | 0.0 | 0.0 | | 0.0 | | 0.0 | 0.0 | | 7.0 | 0.0 |
|  | .125 | 0.0 | | | 0.0 | 0.0 | 0.0 | 0.0 | 0.0 | | 0.0 | | 0.0 | 0.0 | | 7.0 | 0.0 |
|  | .063 | 0.0 | | | 0.0 | 0.0 | 0.0 | 0.0 | 0.0 | | 0.0 | | 0.0 | 0.0 | | 7.0 | 0.0 |
|  | .032 | 0.0 | | | 0.0 | 0.0 | 0.0 | 0.0 | 0.0 | | 0.0 | | 0.0 | 0.0 | | 7.0 | 0.0 |
|  | .016 | 0.0 | | | 0.0 | 0.0 | 0.0 | 0.0 | 0.0 | | 0.0 | | 0.0 | 0.0 | | 0.0 | 0.0 |
| 13 | .500 | 0.0 | | | 0.0 | 0.0 | 6.0 | 6.0 | 7.0 | | 0.0 | | 8.0 | 0.0 | | 9.0 | 0.0 |
|  | .250 | 0.0 | | | 7.0 | 0.0 | 4.0 | 2.0 | 2.0 | | 0.0 | | 7.0 | 0.0 | | 8.0 | 0.0 |
|  | .125 | 0.0 | | | 6.0 | 0.0 | 4.0 | 4.0 | 0.0 | | 0.0 | | 7.0 | 0.0 | | 6.0 | 0.0 |
|  | .063 | 0.0 | | | 2.0 | 0.0 | 2.0 | 2.0 | 0.0 | | 0.0 | | 5.0 | 0.0 | | 4.0 | 0.0 |
|  | .032 | 0.0 | | | 2.0 | 0.0 | 0.0 | 0.0 | 0.0 | | 0.0 | | 4.0 | 0.0 | | 4.0 | 0.0 |
|  | .016 | 0.0 | | | 0.0 | 0.0 | 0.0 | 0.0 | 0.0 | | 0.0 | | 2.0 | 0.0 | | 2.0 | 0.0 |
| 14 | .500 | 3.0 | | | 7.0 | 0.0 | 9.0 | 4.0 | 8.0 | | 6.0 | | 7.0 | 8.0 | | 9.0 | 0.0 |
|  | .250 | 2.0 | | | 7.0 | 0.0 | 9.0 | 2.0 | 7.0 | | 4.0 | | 6.0 | 6.0 | | 9.0 | 0.0 |
|  | .125 | 0.0 | | | 6.0 | 0.0 | 1.0 | 0.0 | 1.0 | | 0.0 | | 4.0 | 0.0 | | 7.0 | 0.0 |
|  | .063 | 0.0 | | | 1.0 | 0.0 | 0.0 | 0.0 | 0.0 | | 0.0 | | 1.0 | 0.0 | | 5.0 | 4.0 |
|  | .032 | 0.0 | | | 0.0 | 0.0 | 0.0 | 0.0 | 0.0 | | 0.0 | | 0.0 | 0.0 | | 5.0 | 1.0 |
|  | .016 | 0.0 | | | 0.0 | 0.0 | 0.0 | 0.0 | 0.0 | | 0.0 | | 0.0 | 0.0 | | | 1.0 |
| 15 | .500 | 0.0 | | | 0.0 | 2.0 | 4.0 | 0.0 | 0.0 | | 0.0 | | 2.0 | 0.0 | | 9.0 | 0.0 |
|  | .250 | 0.0 | | | 2.0 | 1.0 | 1.0 | 0.0 | 0.0 | | 0.0 | | 1.0 | 0.0 | | 2.0 | 0.0 |
|  | .125 | 0.0 | | | 1.0 | 0.0 | 0.0 | 0.0 | 0.0 | | 0.0 | | 0.0 | 0.0 | | 2.0 | 0.0 |
|  | .063 | 0.0 | | | 0.0 | 0.0 | 0.0 | 0.0 | 0.0 | | 0.0 | | 0.0 | 0.0 | | 0.0 | 0.0 |
|  | .032 | 0.0 | | | 0.0 | 0.0 | 0.0 | 0.0 | 0.0 | | 0.0 | | 0.0 | 0.0 | | 0.0 | 7.0 |
|  | .016 | 0.0 | | | 0.0 | 0.0 | 0.0 | 0.0 | 0.0 | | 0.0 | | 0.0 | 0.0 | | 0.0 | 2.0 |
| 16 | .500 | 6.0 | | | 9.0 | 0.0 | 9.0 | 4.0 | 2.0 | | 0.0 | | 6.0 | 0.0 | | 9.0 | 0.0 |
|  | .250 | 4.0 | | | 6.0 | 0.0 | 1.0 | 4.0 | 1.0 | | 0.0 | | 4.0 | 0.0 | | 7.0 | 0.0 |
|  | .125 | 4.0 | | | 2.0 | 0.0 | 1.0 | 0.0 | 1.0 | | 0.0 | | 1.0 | 0.0 | | 4.0 | 0.0 |
|  | .063 | 1.0 | | | 0.0 | 0.0 | 0.0 | 0.0 | 0.0 | | 0.0 | | 0.0 | 0.0 | | 0.0 | 2.0 |
|  | .032 | 0.0 | | | 0.0 | 0.0 | 0.0 | 0.0 | 0.0 | | 0.0 | | 0.0 | 0.0 | | 0.0 | 1.0 |
|  | .016 | 0.0 | | | 0.0 | 0.0 | 0.0 | 0.0 | 0.0 | | 0.0 | | 0.0 | 0.0 | | 0.0 | 0.0 |
| 17 | .500 | 0.0 | | | 9.0 | 4.0 | 9.0 | 9.0 | 9.0 | | 4.0 | | 0.0 | | | 9.0 | 7.0 |
|  | .250 | 0.0 | | | 9.0 | 3.0 | 9.0 | 9.0 | 9.0 | | 4.0 | | 8.0 | | | 9.0 | 7.0 |
|  | .125 | 0.0 | | | 9.0 | 0.0 | 9.0 | 9.0 | 0.0 | | 1.0 | | 7.0 | | | 9.0 | 3.0 |

TABLE I-continued

PRE-EMERGENCE TESTS - RATES IN KG/HA

| Compound No. | RATE | BARNY ARDGR | LARGE CRAB | GREEN FOX | P NUT SEDGE | WILD OATS | QUACK GRASS | FLD B INDWD | WRNGL RY SP | WILD MUSTD | RAGWE ED | PRIKY SIDA | VELVE TLEAF | MATRI CARIA | S BAR LY LA | SUGAR BEETS | CORN FIELD |
|---|---|---|---|---|---|---|---|---|---|---|---|---|---|---|---|---|---|
| | .063 | 0.0 | | | 7.0 | 0.0 | 1.0 | 0.0 | 2.0 | | 1.0 | | 4.0 | 0.0 | | 8.0 | 1.0 |
| | .032 | 0.0 | | | 5.0 | 0.0 | 1.0 | 0.0 | 2.0 | | 0.0 | | 0.0 | 0.0 | | | 0.0 |
| | .016 | 0.0 | | | 2.0 | 0.0 | 0.0 | 0.0 | 0.0 | | 0.0 | | 0.0 | 0.0 | | | 0.0 |
| 18 | .500 | 9.0 | | | 9.0 | 9.0 | 9.0 | 9.0 | 5.0 | | 8.0 | | 9.0 | 8.0 | | 4.0 | 9.0 |
| | .250 | 4.0 | | | 4.0 | 9.0 | 9.0 | 7.0 | 2.0 | | 7.0 | | 9.0 | 4.0 | | 9.0 | 8.0 |
| | .125 | 1.0 | | | 3.0 | 8.0 | 9.0 | 2.0 | 2.0 | | 0.0 | | 8.0 | 4.0 | | 9.0 | 6.0 |
| | .063 | 0.0 | | | 2.0 | 5.0 | 7.0 | 0.0 | 0.0 | | 0.0 | | 6.0 | 0.0 | | 8.0 | 3.0 |
| | .032 | 0.0 | | | 0.0 | 0.0 | 6.0 | 0.0 | 0.0 | | 0.0 | | 0.0 | 0.0 | | 6.0 | 3.0 |
| | .016 | 0.0 | | | 0.0 | 0.0 | 4.0 | 0.0 | 0.0 | 0.0 | 0.0 | | 0.0 | 0.0 | | 6.0 | 2.0 |
| 19 | .500 | 0.0 | | | 9.0 | 9.0 | 9.0 | 9.0 | 8.0 | | 7.0 | | 9.0 | 0.0 | | 9.0 | 9.0 |
| | .250 | 0.0 | | | 8.0 | 9.0 | 9.0 | 9.0 | 8.0 | | 7.0 | | 9.0 | 5.0 | | 9.0 | 9.0 |
| | .125 | 0.0 | | | 0.0 | 9.0 | 9.0 | 0.0 | 6.0 | | 7.0 | | 9.0 | 5.0 | | 9.0 | 9.0 |
| | .063 | 6.0 | | | 6.0 | 9.0 | 9.0 | 5.0 | 6.0 | | 6.0 | | 8.0 | 3.0 | | 9.0 | 7.0 |
| | .032 | 4.0 | | | 2.0 | 9.0 | 5.0 | 0.0 | 2.0 | | 5.0 | | 0.0 | 3.0 | | 9.0 | 8.0 |
| | .016 | 2.0 | | | 0.0 | 6.0 | 3.0 | 0.0 | 0.0 | | 3.0 | | 4.0 | 1.0 | | 7.0 | 6.0 |
| 20 | .500 | 9.0 | | | 2.0 | 9.0 | 9.0 | 0.0 | 0.0 | | 1.0 | | 3.0 | 0.0 | | 9.0 | 9.0 |
| | .250 | 9.0 | | | 2.0 | 9.0 | 9.0 | 9.0 | 8.0 | | 8.0 | | 8.0 | 8.0 | | 9.0 | 0.0 |
| | .125 | 3.0 | | | 2.0 | 8.0 | 9.0 | 3.0 | 7.0 | | 7.0 | | 9.0 | 0.0 | | 9.0 | 0.0 |
| | .063 | 1.0 | | | 1.0 | 7.0 | 9.0 | 7.0 | 3.0 | | 7.0 | | 6.0 | 7.0 | | 9.0 | 7.0 |
| | .032 | 0.0 | | | 0.0 | 5.0 | 6.0 | 1.0 | 1.0 | | 4.0 | | 5.0 | 4.0 | | 8.0 | 7.0 |
| | .016 | 0.0 | | | 0.0 | 0.0 | 2.0 | 0.0 | 0.0 | | 2.0 | | 0.0 | 2.0 | | 0.0 | 7.0 |
| 21 | .500 | 0.0 | | | 0.0 | 0.0 | 0.0 | 9.0 | 7.0 | | 0.0 | | 0.0 | 1.0 | | 0.0 | 3.0 |
| | .250 | 0.0 | | | 0.0 | 0.0 | 4.0 | 6.0 | 4.0 | | 0.0 | | 6.0 | 0.0 | | 9.0 | 0.0 |
| | .125 | 0.0 | | | 4.0 | 0.0 | 3.0 | 0.0 | 2.0 | | 0.0 | | 4.0 | 2.0 | | 8.0 | 0.0 |
| | .063 | 0.0 | | | 2.0 | 0.0 | 1.0 | 4.0 | 0.0 | | 0.0 | | 4.0 | 0.0 | | 8.0 | 0.0 |
| | .032 | 0.0 | | | 0.0 | 0.0 | 0.0 | 2.0 | 0.0 | | 0.0 | | 0.0 | 0.0 | | 4.0 | 0.0 |
| | .016 | 0.0 | | | 0.0 | 0.0 | 0.0 | 0.0 | 0.0 | | 0.0 | | 0.0 | 0.0 | | 2.0 | 0.0 |
| 22 | .500 | 9.0 | | | 4.0 | 9.0 | 9.0 | 9.0 | 8.0 | | 7.0 | | 8.0 | 0.0 | | 2.0 | 0.0 |
| | .250 | 9.0 | | | 1.0 | 9.0 | 9.0 | 9.0 | 7.0 | | 6.0 | | 8.0 | 9.0 | | 9.0 | 0.0 |
| | .125 | 6.0 | | | 1.0 | 7.0 | 8.0 | 4.0 | 7.0 | | 4.0 | | 6.0 | 7.0 | | 9.0 | 7.0 |
| | .063 | 2.0 | | | 1.0 | 4.0 | 0.0 | 4.0 | 2.0 | | 0.0 | | 4.0 | 2.0 | | 0.0 | 6.0 |
| | .032 | 0.0 | | | 0.0 | 2.0 | 8.0 | 4.0 | 0.0 | | 0.0 | | 2.0 | 2.0 | | 7.0 | 3.0 |
| | .016 | 0.0 | | | 0.0 | 0.0 | 2.0 | 0.0 | 0.0 | | 0.0 | | 2.0 | 0.0 | | 6.0 | 2.0 |
| 23 | 8.000 | 8.0 | 8.0 | 9.0 | 7.0 | 9.0 | 9.0 | 9.0 | 8.0 | 9.0 | 5.0 | 8.0 | 8.0 | 0.0 | | 0.0 | 1.0 |
| | .500 | 0.0 | 0.0 | 0.0 | 0.0 | 0.0 | 0.0 | 0.0 | 0.0 | | 0.0 | | 0.0 | 0.0 | 0.0 | 0.0 | 0.0 |
| | .250 | 0.0 | 0.0 | 0.0 | 0.0 | 0.0 | 0.0 | 0.0 | 0.0 | | 0.0 | | 0.0 | 0.0 | 0.0 | 0.0 | 0.0 |
| | .125 | 0.0 | 0.0 | 0.0 | 0.0 | 0.0 | 0.0 | 0.0 | 0.0 | | 0.0 | | 0.0 | 0.0 | 0.0 | 0.0 | 0.0 |
| | .063 | 0.0 | 0.0 | 0.0 | 0.0 | 0.0 | 0.0 | 0.0 | 0.0 | | 0.0 | | 0.0 | 0.0 | | 0.0 | 0.0 |
| | .032 | 0.0 | | 0.0 | 0.0 | 0.0 | 0.0 | 0.0 | 0.0 | | 0.0 | | 0.0 | 0.0 | | 0.0 | 0.0 |
| | .016 | 0.0 | | 0.0 | 0.0 | 0.0 | 0.0 | 0.0 | 0.0 | | 0.0 | | 0.0 | 0.0 | | 0.0 | 0.0 |

EXAMPLE 68

Postemergence Herbicidal Evaluation of Test Compounds

The postemergence herbicidal activity of the compounds of the present invention is determined by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures containing 0.5% TWEEN® 20, a polyoxyethylene sorbitan monolaurate surfactant of Atlas Chemical Industries, in sufficient quantities to provide the equivalent of about 0.16 kg to 8.0 kg per hectare of active compound when applied to the plants through a spray nozzle operating at 40 psig for a predetermined time. After spraying, the plants are placed on greenhouse benches and are cared for in the usual manner, commensurate with conventional greenhouse practices. From four to give weeks after treatment, the seedling plants, are examined and rated according to the rating system provided in Example 36 above. The data obtained are recorded in Table II below. The compounds evaluated are reported by compound number given in Example 36.

TABLE II

PRE-EMERGENCE TESTS - RATES IN KG/HA

| Compound No. | RATE | BARNY ARDGR | LARGE CRAB | GREEN FOX | P NUT SEDGE | WILD OATS | QUACK GRASS | FLD B INDWD | WRNGL RY SP | WILD MUSTD | RAGWE ED | PRIKY SIDA | VELVE TLEAF | MATRI CARIA | S BAR LY LA | SUGAR BEETS | CORN FIELD |
|---|---|---|---|---|---|---|---|---|---|---|---|---|---|---|---|---|---|
| 1 | 1.000 | 0.0 | | 4.0 | 0.0 | 0.0 | 0.0 | 0.0 | 1.0 | | 0.0 | | 2.0 | 0.0 | | 7.0 | 4.0 |
| | .500 | 0.0 | | 4.0 | 0.0 | 0.0 | 0.0 | 8.0 | 1.0 | | 0.0 | | 2.0 | 0.0 | | 4.0 | 3.0 |
| | .250 | 0.0 | | 3.0 | 0.0 | 0.0 | 0.0 | 6.0 | 1.0 | | 0.0 | | 0.0 | 0.0 | | 4.0 | 3.0 |
| | .125 | 0.0 | | 4.0 | 0.0 | 0.0 | 0.0 | 5.0 | 0.0 | | 0.0 | | 0.0 | 0.0 | | 4.0 | |
| 2 | 1.000 | 4.0 | | | 3.0 | 7.0 | 7.0 | 6.0 | 5.0 | | 6.0 | | 3.0 | 9.0 | | 0.0 | 4.0 |
| | .500 | 3.0 | | | 2.0 | 6.0 | 7.0 | 4.0 | 2.0 | | 5.0 | | 1.0 | 9.0 | | 0.0 | 3.0 |
| | .250 | 2.0 | | | 2.0 | 4.0 | 3.0 | 2.0 | 0.0 | | 0.0 | | 0.0 | 0.0 | | 3.0 | 2.0 |
| | .125 | 0.0 | | | 0.0 | 2.0 | 1.0 | 0.0 | 0.0 | | 0.0 | | 0.0 | 0.0 | | 1.0 | 0.0 |
| | .063 | 0.0 | | | 0.0 | 2.0 | 0.0 | 0.0 | 0.0 | | 0.0 | | 0.0 | 0.0 | | 0.0 | 0.0 |
| | .032 | 0.0 | | | 0.0 | 1.0 | 0.0 | 0.0 | 0.0 | | 0.0 | | 0.0 | 0.0 | | 0.0 | 0.0 |
| 4 | 8.000 | 9.0 | 9.0 | | 9.0 | 9.0 | 9.0 | 9.0 | 9.0 | 9.0 | 9.0 | 9.0 | 9.0 | 9.0 | | 9.0 | 9.0 |
| | 1.000 | 9.0 | | 9.0 | 4.5 | 9.0 | 9.0 | 9.0 | 8.5 | | 9.0 | | 7.5 | 9.0 | | 9.0 | 9.0 |
| | .500 | 9.0 | | | 3.5 | 9.0 | 9.0 | 9.0 | 5.5 | | 7.5 | | 6.5 | 9.0 | | 9.0 | 9.0 |
| | .250 | 9.0 | | | 1.5 | 9.0 | 8.0 | 9.0 | 5.0 | | 5.5 | | 5.5 | 8.0 | | 9.0 | 9.0 |
| | .125 | 8.0 | | | 0.5 | 9.0 | 8.0 | 6.5 | 4.5 | | 3.0 | | 3.5 | 1.5 | | 6.0 | 8.5 |
| | .063 | 5.0 | | | 0.5 | 7.5 | 3.5 | 4.0 | 3.5 | | 1.0 | | 2.5 | 1.5 | | 6.0 | 7.5 |
| | .032 | 3.5 | | | 0.0 | 3.0 | 2.0 | 1.0 | 3.0 | | 0.5 | | 1.5 | 0.5 | | 9.0 | 9.0 |
| 5 | 1.000 | 9.0 | | | 9.0 | 9.0 | 9.0 | 9.0 | 9.0 | | 7.0 | | 8.0 | 7.0 | | 9.0 | 8.0 |
| | .750 | 9.0 | | 9.0 | 7.0 | | 7.0 | 8.5 | 8.0 | | 5.5 | 7.0 | 4.0 | | | | 8.5 |
| | .500 | 9.0 | | 8.0 | 8.0 | | 8.0 | 8.0 | 8.0 | | 5.5 | 6.0 | 6.5 | | | | 8.0 |
| | .375 | 7.0 | | 8.0 | 6.0 | | 6.0 | 0.0 | 7.0 | | 6.0 | 5.0 | 4.0 | | | 9.0 | 8.5 |
| | .250 | 8.0 | | 8.0 | 5.5 | | 7.5 | 5.0 | 5.0 | | 5.0 | 4.0 | 5.5 | | | | 8.5 |
| | .125 | 6.0 | | 8.0 | 3.0 | 9.0 | 5.5 | 5.0 | 4.0 | | 4.0 | 3.0 | 3.0 | 5.0 | | 9.0 | 7.0 |
| | .100 | 7.5 | | 8.0 | 3.5 | | 5.5 | 4.0 | 5.0 | | 3.0 | 0.0 | 5.0 | | | | 8.0 |
| | .063 | 8.0 | | | 5.0 | 8.0 | 7.0 | 7.0 | 8.0 | | 3.0 | | 5.0 | 3.0 | | 9.0 | 8.0 |
| | .032 | 7.0 | | | 2.0 | 8.0 | 5.0 | 6.0 | 5.0 | | 3.0 | | 2.0 | 3.0 | | 3.0 | 8.0 |
| 6 | 1.000 | 0.0 | | | 0.0 | 6.0 | 4.0 | 7.0 | 2.0 | | 0.0 | | 0.0 | 0.0 | | 8.0 | 5.0 |
| | .500 | 0.0 | | | 0.0 | 0.0 | 0.0 | 6.0 | 1.0 | | 0.0 | | 2.0 | 0.0 | | 2.0 | 0.0 |
| | .250 | 0.0 | | | 0.0 | 0.0 | 0.0 | 0.0 | 0.0 | | 0.0 | | 0.0 | 0.0 | | 2.0 | 0.0 |
| | .125 | 0.0 | | | 0.0 | 0.0 | 0.0 | 0.0 | 0.0 | | 0.0 | | 0.0 | 0.0 | | 1.0 | 0.0 |
| | .063 | 0.0 | | | 0.0 | 0.0 | 0.0 | 0.0 | 0.0 | | 0.0 | | 0.0 | 0.0 | | 0.0 | 0.0 |
| | .032 | 0.0 | | | 0.0 | 0.0 | 0.0 | 0.0 | 0.0 | | 0.0 | | 0.0 | 0.0 | | 0.0 | 0.0 |
| 7 | 8.000 | 9.0 | 9.0 | 9.0 | 9.0 | 9.0 | 9.0 | 9.0 | 8.0 | 9.0 | 9.0 | 9.0 | 9.0 | | | 9.0 | 9.0 |
| | 1.000 | 9.0 | | | 9.0 | 9.0 | 8.0 | 9.0 | 9.0 | | 7.0 | | 9.0 | 8.0 | | 9.0 | 9.0 |
| | .500 | 9.0 | | | 8.0 | 9.0 | 8.0 | 9.0 | 9.0 | | 6.0 | | 9.0 | 7.0 | | 9.0 | 9.0 |
| | .250 | 9.0 | | | 8.0 | 9.0 | 7.0 | 9.0 | 8.0 | | 6.0 | | 9.0 | 7.0 | | 9.0 | 9.0 |
| | .125 | 9.0 | | | 6.0 | 9.0 | 7.0 | 9.0 | 7.0 | | 4.0 | | 4.0 | 7.0 | | 9.0 | 8.0 |
| | .063 | 9.0 | | | 4.0 | 8.0 | 2.0 | 8.0 | 6.0 | | 0.0 | | 4.0 | 2.0 | | 8.0 | 8.0 |
| | .032 | 9.0 | | | 0.0 | 0.0 | 0.0 | 0.0 | 0.0 | | 0.0 | | 4.0 | 0.0 | | 6.0 | 5.0 |
| 8 | 1.000 | 0.0 | | | 0.0 | 9.0 | 2.0 | 0.0 | 6.0 | | 0.0 | | 4.0 | 0.0 | | 6.0 | 0.0 |
| | .500 | 0.0 | | | 0.0 | 0.0 | 0.0 | 0.0 | 4.0 | | 0.0 | | 2.0 | 0.0 | | 2.0 | 0.0 |
| | .250 | 0.0 | | | 0.0 | 0.0 | 0.0 | 7.0 | 2.0 | | 0.0 | | 1.0 | 0.0 | | 1.0 | 0.0 |
| | .125 | 0.0 | | | 0.0 | 0.0 | 0.0 | 6.0 | 0.0 | | 0.0 | | 0.0 | 0.0 | | 0.0 | 0.0 |
| | .063 | 0.0 | | | 0.0 | 0.0 | 0.0 | 6.0 | 0.0 | | 0.0 | | 0.0 | 0.0 | | 0.0 | 0.0 |
| | .032 | 0.0 | | | 0.0 | 0.0 | 0.0 | 2.0 | 0.0 | | 0.0 | | 0.0 | 0.0 | | 0.0 | 0.0 |
| 9 | 1.000 | 6.0 | | | 4.0 | 9.0 | 2.0 | 0.0 | 6.0 | | 0.0 | | 2.0 | 0.0 | | 4.0 | 6.0 |
| | .500 | 3.0 | | | 2.0 | 9.0 | 2.0 | 0.0 | 4.0 | | 0.0 | | 2.0 | 0.0 | | 4.0 | 2.0 |
| | .250 | 1.0 | | | 0.0 | 6.0 | 1.0 | 0.0 | 2.0 | | 0.0 | | 0.0 | 0.0 | | 4.0 | 1.0 |
| | .125 | 0.0 | | | 0.0 | 2.0 | 0.0 | 0.0 | 0.0 | | 0.0 | | 0.0 | 0.0 | | 2.0 | 1.0 |
| | .063 | 0.0 | | | 0.0 | 2.0 | 0.0 | 0.0 | 0.0 | | 0.0 | | 0.0 | 0.0 | | 1.0 | 1.0 |

TABLE II-continued

PRE-EMERGENCE TESTS - RATES IN KG/HA

| Compound No. | RATE | BARNY ARDGR | LARGE CRAB | GREEN FOX | P NUT SEDGE | WILD OATS | QUACK GRASS | FLD B INDWD | WRNGL RY SP | WILD MUSTD | RAGWE ED | PRIKY SIDA | VELVE TLEAF | MATRI CARIA | S BAR LY LA | SUGAR BEETS | CORN FIELD |
|---|---|---|---|---|---|---|---|---|---|---|---|---|---|---|---|---|---|
| 11 | .032 | 0.0 | | | 0.0 | 1.0 | 0.0 | 0.0 | 0.0 | | 0.0 | | 0.0 | 0.0 | | 0.0 | 0.0 |
|    | 1.000 | 9.0 | | | 7.0 | 9.0 | 9.0 | 9.0 | 9.0 | | 6.0 | | 8.0 | 8.0 | | 9.0 | 9.0 |
|    | .500 | 9.0 | | | 7.0 | 9.0 | 9.0 | 9.0 | 9.0 | | 3.0 | | 7.0 | 6.0 | | 9.0 | 9.0 |
|    | .250 | 9.0 | | | 7.0 | 9.0 | 9.0 | 9.0 | 9.0 | | 1.0 | | 7.0 | 4.0 | | 9.0 | 9.0 |
|    | .125 | 7.0 | | | 5.0 | 9.0 | 2.0 | 9.0 | 7.0 | | 0.0 | | 7.0 | 0.0 | | 9.0 | 9.0 |
|    | .063 | 7.0 | | | 4.0 | 8.0 | 0.0 | 8.0 | 6.0 | | 0.0 | | 4.0 | 0.0 | | 9.0 | 7.0 |
|    | .032 | 4.0 | | | 4.0 | 2.0 | 0.0 | 4.0 | 0.0 | | 0.0 | | 2.0 | 0.0 | | 4.0 | 4.0 |
| 12 | 1.000 | 0.0 | | | 0.0 | 0.0 | 0.0 | 0.0 | 0.0 | | 0.0 | | 2.0 | 0.0 | | 0.0 | 0.0 |
|    | .500 | 0.0 | | | 0.0 | 0.0 | 0.0 | 0.0 | 0.0 | | 0.0 | | 0.0 | 0.0 | | 0.0 | 0.0 |
|    | .250 | 0.0 | | | 0.0 | 0.0 | 0.0 | 0.0 | 0.0 | | 0.0 | | 0.0 | 0.0 | | 0.0 | 0.0 |
|    | .125 | 0.0 | | | 0.0 | 0.0 | 0.0 | 0.0 | 0.0 | | 0.0 | | 0.0 | 0.0 | | 0.0 | 0.0 |
|    | .063 | 0.0 | | | 0.0 | 0.0 | 0.0 | 0.0 | 0.0 | | 0.0 | | 0.0 | | | 0.0 | 0.0 |
|    | .032 | 0.0 | | | 0.0 | 0.0 | 0.0 | 0.0 | 0.0 | | 0.0 | | 0.0 | | | 0.0 | 0.0 |
| 13 | 1.000 | 4.0 | | | 6.0 | 2.0 | 2.0 | 3.0 | 4.0 | | 0.0 | | 3.0 | | | 9.0 | 6.0 |
|    | .500 | 2.0 | | | 6.0 | 0.0 | 0.0 | 1.0 | 1.0 | | 0.0 | | 2.0 | | | 4.0 | 3.0 |
|    | .250 | 0.0 | | | 0.0 | 0.0 | 0.0 | 0.0 | 0.0 | | 0.0 | | 0.0 | | | 4.0 | 2.0 |
|    | .125 | 0.0 | | | 0.0 | 0.0 | 0.0 | 0.0 | 0.0 | | 0.0 | | 0.0 | | | 2.0 | 2.0 |
|    | .063 | 0.0 | | | 0.0 | 0.0 | 0.0 | 0.0 | 0.0 | | 0.0 | | 0.0 | | | 2.0 | 0.0 |
|    | .032 | 0.0 | | | 0.0 | 0.0 | 0.0 | 0.0 | 0.0 | | 0.0 | | 0.0 | | | 0.0 | 0.0 |
| 14 | 1.000 | 7.0 | | | 6.0 | 8.0 | 7.0 | 8.0 | 7.0 | | 3.0 | | 6.0 | 6.0 | | 9.0 | 8.0 |
|    | .500 | 6.0 | | | 5.0 | 5.0 | 5.0 | 9.0 | 7.0 | | 3.0 | | 7.0 | 7.0 | | 9.0 | 7.0 |
|    | .250 | 4.0 | | | 0.0 | 2.0 | 3.0 | 3.0 | 5.0 | | 2.0 | | 3.0 | 4.0 | | 7.0 | 3.0 |
|    | .125 | 3.0 | | | 0.0 | 0.0 | 0.0 | 3.0 | 0.0 | | 0.0 | | 0.0 | 0.0 | | 7.0 | 0.0 |
|    | .063 | 0.0 | | | 0.0 | 0.0 | 0.0 | 0.0 | 0.0 | | 0.0 | | 0.0 | 0.0 | | 0.0 | 0.0 |
|    | .032 | 0.0 | | | 0.0 | 0.0 | 0.0 | 0.0 | 0.0 | | 0.0 | | 0.0 | 0.0 | | 0.0 | 0.0 |
| 15 | 1.000 | 5.0 | | | 0.0 | 0.0 | 0.0 | 0.0 | 0.0 | | 0.0 | | 3.0 | 0.0 | | 0.0 | 0.0 |
|    | .500 | 0.0 | | | 0.0 | 0.0 | 0.0 | 3.0 | 0.0 | | 0.0 | | 2.0 | 0.0 | | 0.0 | 0.0 |
|    | .250 | 0.0 | | | 0.0 | 0.0 | 0.0 | 0.0 | 0.0 | | 0.0 | | 0.0 | 0.0 | | 0.0 | 0.0 |
|    | .125 | 0.0 | | | 0.0 | 0.0 | 0.0 | 0.0 | 0.0 | | 0.0 | | 0.0 | 0.0 | | 0.0 | 0.0 |
|    | .063 | 0.0 | | | 0.0 | 0.0 | 0.0 | 0.0 | 0.0 | | 0.0 | | 0.0 | 0.0 | | 0.0 | 0.0 |
|    | .032 | 0.0 | | | 0.0 | 0.0 | 0.0 | 0.0 | 0.0 | | 0.0 | | 0.0 | 0.0 | | 0.0 | 0.0 |
| 16 | 1.000 | 0.0 | | | 0.0 | 0.0 | 0.0 | 0.0 | 0.0 | | 0.0 | | 0.0 | 0.0 | | 0.0 | 0.0 |
|    | .500 | 0.0 | | | 0.0 | 0.0 | 0.0 | 0.0 | 0.0 | | 0.0 | | 0.0 | 0.0 | | 0.0 | 0.0 |
|    | .250 | 0.0 | | | 0.0 | 0.0 | 0.0 | 0.0 | 0.0 | | 0.0 | | 0.0 | 0.0 | | 0.0 | 0.0 |
|    | .125 | 0.0 | | | 0.0 | 0.0 | 0.0 | 0.0 | 0.0 | | 0.0 | | 0.0 | 0.0 | | 0.0 | 0.0 |
|    | .063 | 0.0 | | | 0.0 | 0.0 | 0.0 | 0.0 | 0.0 | | 0.0 | | 0.0 | 0.0 | | 0.0 | 0.0 |
|    | .032 | 0.0 | | | 0.0 | 0.0 | 0.0 | 0.0 | 0.0 | | 0.0 | | 0.0 | 0.0 | | 0.0 | 0.0 |
| 17 | 1.000 | 9.0 | | | 9.0 | 8.0 | 7.0 | 9.0 | 8.0 | | 3.0 | | 9.0 | 4.0 | | 9.0 | 7.0 |
|    | .500 | 7.0 | | | 8.0 | 6.0 | 3.0 | 8.0 | 7.0 | | 2.0 | | 8.0 | 4.0 | | 9.0 | 6.0 |
|    | .250 | 6.0 | | | 8.0 | 3.0 | 0.0 | 7.0 | 8.0 | | 0.0 | | 8.0 | 4.0 | | 9.0 | 5.0 |
|    | .125 | 3.0 | | | 6.0 | 0.0 | 0.0 | 5.0 | 8.0 | | 0.0 | | 7.0 | 3.0 | | 8.0 | 5.0 |
|    | .063 | 0.0 | | | 3.0 | 0.0 | 0.0 | 5.0 | 5.0 | | 0.0 | | 3.0 | 0.0 | | 4.0 | 3.0 |
|    | .032 | 0.0 | | | 0.0 | 0.0 | 0.0 | 0.0 | 0.0 | | 0.0 | | 0.0 | 0.0 | | 0.0 | 0.0 |
| 18 | 1.000 | 2.0 | | | 5.0 | 4.0 | 7.0 | 5.0 | 5.0 | | 2.0 | | 7.0 | 4.0 | | 9.0 | 7.0 |
|    | .500 | 1.0 | | | 5.0 | 3.0 | 7.0 | 6.0 | 8.0 | | 1.0 | | 7.0 | 4.0 | | 9.0 | 6.0 |
|    | .250 | 0.0 | | | 2.0 | 1.0 | 3.0 | 6.0 | 7.0 | | 0.0 | | 3.0 | 4.0 | | 9.0 | 5.0 |
|    | .125 | 0.0 | | | 1.0 | 0.0 | 2.0 | 2.0 | 0.0 | | 0.0 | | 1.0 | 3.0 | | 8.0 | 5.0 |
|    | .063 | 0.0 | | | 0.0 | 0.0 | 0.0 | 0.0 | 0.0 | | 0.0 | | 0.0 | 0.0 | | 4.0 | 3.0 |
|    | .032 | 0.0 | | | 0.0 | 0.0 | 0.0 | 0.0 | 0.0 | | 0.0 | | 0.0 | 0.0 | | 0.0 | 0.0 |
| 19 | 1.000 | 9.0 | | | 8.0 | 9.0 | 9.0 | 9.0 | 9.0 | | 9.0 | | 9.0 | 8.0 | | 9.0 | 9.0 |

TABLE II-continued

PRE-EMERGENCE TESTS - RATES IN KG/HA

| Compound No. | RATE | BARNY ARDGR | LARGE CRAB | GREEN FOX | P NUT SEDGE | WILD OATS | QUACK GRASS | FLD B INDWD | WRNGL RY SP | WILD MUSTD | RAGWE ED | PRIKY SIDA | VELVE TLEAF | MATRI CARIA | S BAR LY LA | SUGAR BEETS | CORN FIELD |
|---|---|---|---|---|---|---|---|---|---|---|---|---|---|---|---|---|---|
| | .500 | 9.0 | | | 7.0 | 9.0 | 9.0 | 9.0 | 8.0 | | 7.0 | | 9.0 | 7.0 | | 9.0 | 9.0 |
| | .250 | 9.0 | | | 6.0 | 9.0 | 9.0 | 9.0 | 8.0 | | 7.0 | | 9.0 | 7.0 | | 9.0 | 9.0 |
| | .125 | 9.0 | | | 5.0 | 9.0 | 8.0 | 9.0 | 6.0 | | 5.0 | | 6.0 | 5.0 | | 9.0 | 9.0 |
| | .063 | 9.0 | | | 2.0 | 9.0 | 8.0 | 9.0 | 2.0 | | 1.0 | | 2.0 | 3.0 | | 9.0 | 9.0 |
| | .032 | 5.0 | | | 0.0 | 9.0 | 7.0 | | 0.0 | | 0.0 | | 0.0 | 1.0 | | 9.0 | 9.0 |
| 20 | 1.000 | 9.0 | | | 0.0 | 9.0 | 9.0 | 9.0 | 5.0 | | 7.0 | | 9.0 | 9.0 | | 9.0 | 9.0 |
| | .500 | 9.0 | | | 0.0 | 9.0 | 9.0 | 5.0 | 4.0 | | 3.0 | | 8.0 | 8.0 | | 9.0 | 9.0 |
| | .250 | 9.0 | | | 0.0 | 9.0 | 9.0 | | 1.0 | | 1.0 | | 3.0 | 6.0 | | 0.0 | 9.0 |
| | .125 | 8.0 | | | 0.0 | 0.0 | 7.0 | 0.0 | 0.0 | | 1.0 | | 0.0 | 5.0 | | 0.0 | 9.0 |
| | .063 | 2.0 | | | 0.0 | 7.0 | 2.0 | 0.0 | 0.0 | | 0.0 | | 0.0 | 1.0 | | 7.0 | 9.0 |
| | .032 | 0.0 | | | 0.0 | 3.0 | 0.0 | 0.0 | 0.0 | | 0.0 | | 0.0 | 0.0 | | 7.0 | 7.0 |
| 21 | 1.000 | 9.0 | | | 9.0 | 9.0 | 7.0 | 9.0 | 9.0 | | 7.0 | | 9.0 | 6.0 | | 9.0 | 8.0 |
| | .500 | 9.0 | | | 7.0 | 9.0 | 6.0 | 8.0 | 9.0 | | 7.0 | | 9.0 | 3.0 | | 8.0 | 6.0 |
| | .250 | 9.0 | | | 7.0 | 8.0 | 7.0 | 7.0 | 7.0 | | 6.0 | | 7.0 | 1.0 | | 5.0 | 3.0 |
| | .125 | 5.0 | | | 2.0 | 0.0 | 3.0 | 7.0 | 4.0 | | 2.0 | | 6.0 | 0.0 | | 2.0 | 1.0 |
| | .063 | 2.0 | | | 1.0 | 4.0 | 1.0 | 6.0 | 0.0 | | 1.0 | | 2.0 | 0.0 | | 2.0 | 0.0 |
| | .032 | 0.0 | | | 0.0 | 2.0 | 0.0 | 2.0 | 0.0 | | 0.0 | | 1.0 | 0.0 | | 0.0 | 0.0 |
| 23 | 0.000 | 0.0 | 0.0 | 2.0 | 0.0 | 6.0 | 0.0 | 0.0 | 3.0 | | 0.0 | 0.0 | 0.0 | 0.0 | 0.0 | 0.0 | 0.0 |
| | 1.000 | 0.0 | | 0.0 | 0.0 | 0.0 | 0.0 | 0.0 | 0.0 | 0.0 | 0.0 | | 0.0 | 0.0 | 0.0 | 0.0 | 0.0 |
| | .500 | 0.0 | | 0.0 | 0.0 | 0.0 | 0.0 | 0.0 | 0.0 | | 0.0 | | 0.0 | 0.0 | 0.0 | 0.0 | 0.0 |
| | .250 | 0.0 | | 0.0 | 0.0 | 0.0 | 0.0 | 0.0 | 0.0 | | 0.0 | | 0.0 | 0.0 | 0.0 | 0.0 | 0.0 |
| | .125 | 0.0 | | 0.0 | 0.0 | 0.0 | 0.0 | 0.0 | 0.0 | | 0.0 | | 0.0 | 0.0 | | 0.0 | 0.0 |
| | .063 | 0.0 | | 0.0 | 0.0 | 0.0 | 0.0 | 0.0 | 0.0 | | 0.0 | | 0.0 | 0.0 | | 0.0 | 0.0 |
| | .032 | 0.0 | | | 0.0 | 0.0 | 0.0 | 0.0 | 0.0 | | 0.0 | | 0.0 | 0.0 | | 0.0 | 0.0 |
| 24 | 1.000 | 0.0 | | | 0.0 | 0.0 | 0.0 | 7.0 | 4.0 | | 0.0 | | 0.0 | 0.0 | | 0.0 | 2.0 |
| | .500 | 0.0 | | | 0.0 | 0.0 | 0.0 | 6.0 | 2.0 | | 0.0 | | 0.0 | 0.0 | | 0.0 | 2.0 |
| | .250 | 0.0 | | | 0.0 | 0.0 | 0.0 | 2.0 | 1.0 | | 0.0 | | 0.0 | 0.0 | | 0.0 | 2.0 |
| | .125 | 0.0 | | | 0.0 | 0.0 | 0.0 | 0.0 | 0.0 | | 0.0 | | 0.0 | 0.0 | | 0.0 | 1.0 |
| | .063 | 0.0 | | | 0.0 | 0.0 | 0.0 | 0.0 | 0.0 | | 0.0 | | 0.0 | 0.0 | | 0.0 | 1.0 |
| | .032 | 0.0 | | | 0.0 | 0.0 | 0.0 | 0.0 | 0.0 | | 0.0 | | 0.0 | 0.0 | | 0.0 | 0.0 |
| 25 | 1.000 | 4.0 | | | 7.0 | 8.0 | 9.0 | 9.0 | 2.0 | | 2.0 | | 7.0 | 2.0 | | 6.0 | 8.0 |
| | .500 | 2.0 | | | 6.0 | 4.0 | 7.0 | 9.0 | 1.0 | | 1.0 | | 7.0 | 1.0 | | 6.0 | 8.0 |
| | .250 | 0.0 | | | 4.0 | 3.0 | 3.0 | 7.0 | 0.0 | | 0.0 | | 3.0 | 0.0 | | 4.0 | 4.0 |
| | .125 | 0.0 | | | 2.0 | 1.0 | 2.0 | 6.0 | 0.0 | | 0.0 | | 2.0 | 0.0 | | 2.0 | 3.0 |

What is claimed is:

1. A compound having the structure:

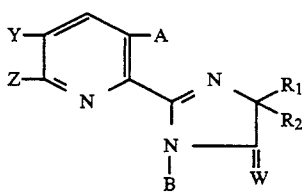   (I)

or

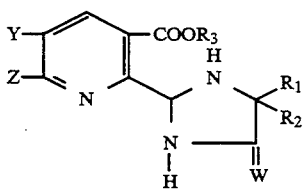   (II)

wherein $R_1$ is $C_1$-$C_4$ alkyl;

$R_2$ is $C_1$-$C_4$ alkyl or $C_3$-$C_6$ cycloalkyl; and when $R_1$ and $R_2$ are taken together with the carbon to which they are attached they may represent $C_3$-$C_6$ cycloalkyl optionally substituted with methyl;

A is $COOR_3$, $CONHR_6$, CHO, $CH_2OH$, $COCH_3$, $COC_6H_5$, CN, $CH_3$, CH=NOH, $CH_2COOH$, CONHOH, $CH_2CH_2COOH$, $CHR_8OH$,

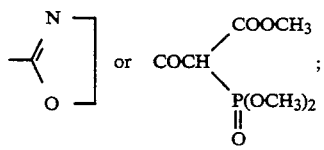;

$R_3$ is hydrogen,

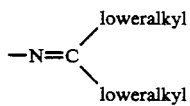

$C_1$-$C_{12}$ alkyl optionally substituted with one of the following groups: $C_1$-$C_3$ alkoxy, $C_1$-$C_3$ alkylthio, halogen, hydroxy, $C_3$-$C_6$ cycloalkyl, benzyloxy, furyl, phenyl, halophenyl, loweralkylphenyl, loweralkoxyphenyl, nitrophenyl, carboxyl, loweralkoxycarbonyl, cyano or triloweralkylammonium halide;

$C_3$-$C_{12}$ alkenyl optionally substituted with one of the following groups: $C_1$-$C_3$ alkoxy, phenyl, halogen or loweralkoxycarbonyl or with two $C_1$-$C_3$ alkoxy groups or two halogen groups;

$C_3$-$C_6$ cycloalkyl optionally substituted with one or two $C_1$-$C_3$ alkyl groups;

$C_3$-$C_{16}$ alkynyl optionally substituted with one or two $C_1$-$C_3$ alkyl groups; or a cation;

$R_6$ is hydrogen, hydroxyl, $C_3$-alkenyl, $C_3$-alkynyl or $C_1$-$C_4$ alkyl optionally substituted with one hydroxyl or one chlorine group;

B is H, $COR_4$ or $SO_2R_5$;

$R_4$ is $C_1$-$C_{11}$ alkyl, chloromethyl or phenyl optionally substituted with one chloro, one nitro or one methoxy group;

$R_5$ is $C_1$-$C_4$ alkyl or phenyl optionally substituted with one methyl group;

W is O or S;

$R_8$ is $C_1$-$C_4$ alkyl or phenyl;

Y and Z may independently be selected from the group consisting of hydrogen, halogen, $C_1$-$C_6$ alkyl, $C_1$-$C_4$ hydroxyalkyl, $C_1$-$C_6$ alkoxy, $C_1$-$C_4$ alkylthio, phenoxy, $C_1$-$C_4$ haloalkyl, nitro, cyano, $C_1$-$C_4$ alkylamino, di-$C_1$-$C_4$ alkylamino, $C_1$-$C_4$ alkylsulfonyl, difluoromethoxy, trifluoromethoxy, 1,1,2,2,-tetrafluoroethoxy, phenyl optionally substituted with one $C_1$-$C_4$ alkyl, $C_1$-$C_4$ alkoxy or halogen;

$C_3$-$C_8$ straight or branched alkenyloxy optionally substituted with 1 to 3 halogens;

$C_3$-$C_8$ straight or branched alkynyloxy optionally substituted with 1 to 3 halogens;

$C_2$-$C_6$ straight or branched alkynyl substituted with hydroxy;

$C_3$-$C_6$ cycloalkyl interrupted by 1 oxygen, sulfur, amino or $C_1$-$C_4$ alkylamino; and oxiranyl optionally substituted by one or two $C_1$-$C_4$ alkyl;

And at least one member of Y and Z must be selected from the group consisting of:

$C_2$-$C_6$ straight or branched alkenyl optionally substituted with phenyl, $C_1$-$C_4$ alkoxy or 1 to 3 halogens;

$C_2$-$C_6$ straight or branched alkynyl optionally substituted with phenyl, $C_1$-$C_4$ alkoxy or 1 to 3 halogens;

$C_3$-$C_6$ cycloalkyl optionally substituted with methyl, halogen or $C_1$-$C_4$ alkoxy;

$C_1$-$C_4$ alkylcarbonyl optionally substituted with $C_1$-$C_4$ alkoxy or 1 to 3 halogens;

$C_1$-$C_4$ alkylcarbonylamino optionally substituted on nitrogen with $C_1$-$C_2$ alkyl or $C_1$-$C_4$ alkoxy and on carbon with $C_1$-$C_4$ alkoxy or 1 to 3 halogens;

$C_1$-$C_4$ alkylcarbonyloxy optionally substituted with $C_1$-$C_4$ alkoxy or 1 to 3 halogens;

$C_1$-$C_4$ alkyl substituted with one or more of the following groups: $C_1$-$C_4$ alkoxy optionally substituted with phenyl, thienyl, furyl, cyclopropyl, tetrahydrofuryl, $C_1$-$C_4$ alkoxy, $C_1$-$C_4$ dialkylamino, $C_1$-$C_4$ alkylamino, $C_1$-$C_4$ trialkylammonium or 1 to 3 halogens; with the proviso that when the substituent on the $C_1$-$C_4$ alkoxy group is $C_1$-$C_4$ alkoxy, $C_1$-$C_4$ alkylamino, $C_1$-$C_4$ dialkylamino or $C_1$-$C_4$ trialkylammonium, the respective heteroatoms are separated by at least 2 carbon atoms;

$C_1$-$C_4$ alkenyloxy optionally substituted with 1 to 3 halogens;

$C_1$-$C_4$ alkynyloxy optionally substituted with 1 to 3 halogens;

$C_3$-$C_6$ cycloalkoxy; phenylthio;

$C_1$-$C_4$ alkylthio optionally substituted with phenyl or 1 to 3 halogens;

$C_1$-$C_4$ alkylsulfinyl optionally substituted with phenyl or 1 to 3 halogens;

$C_1$-$C_4$ alkylsulfonyl optionally substituted with phenyl or 1 to 3 halogens;

$C_1$-$C_4$ alkylamino optionally substituted on carbon by phenyl or 1 to 3 halogens;

$C_1$-$C_4$ dialkylamino;

$C_1$-$C_4$ trialkylammonium;

$C_1$-$C_4$ alkylcarbonyloxy; cyano;

phenylamino, optionally substituted in the ring by 1 to 3 halogens, $C_1$-$C_4$ alkyl, or $C_1$-$C_4$ alkoxy;

phenoxy, optionally substituted in the ring by 1 to 3 halogens, $C_1$-$C_4$ alkyl, or $C_1$-$C_4$ alkoxy;

2(or 3)-furyl optionally substituted with halogen or $C_1$–$C_3$ alkyl;

2(or 3)-thienyl optionally substituted with halogen or $C_1$–$C_3$ alkyl;

N-methyl-2(or 3)-pyrrolyl; hydroxy; formyl;

amino optionally substituted with $C_1$–$C_4$ alkoxy, $C_1$–$C_4$ alkylsulfonyl, $C_1$–$C_2$ alkyl and $C_1$–$C_4$ alkoxy, $C_1$–$C_4$ alkylsulfonyl and $C_1$–$C_2$ alkyl, amino, $C_1$–$C_4$ monoalkylamino, or $C_1$–$C_4$ dialkylamino;

2(or 4)-pyridyloxy optionally substituted with $C_1$–$C_4$ alkyl, trifluoromethyl or 1 or 2 halogens;

$C_1$–$C_4$ mono or dialkylaminocarbonylamino, optionally substituted on the nitrogen attached to the ring with $C_1$–$C_2$ alkyl or $C_1$–$C_4$ alkoxy;

$C_1$–$C_4$ alkoxycarbonylamino, optionally substituted on nitrogen with $C_1$–$C_2$ alkyl or $C_1$–$C_4$ alkoxy; and $C_1$–$C_4$ mono or dialkylaminocarbonyloxy;

Provided also that when Y is hydroxy, Z cannot be hydrogen;

Provided also that when B is $COR_4$ or $SO_2R_5$, A is $CH_3$, CN or $COOR_3$ in which $R_3$ is other than H or a cation and W is O, then Y and Z cannot be alkylamino, hydroxyl or hydroxyloweralkyl;

an N-oxide thereof when W is O, provided that $R_3$ cannot be unsaturated alkyl and Y and Z cannot be alkylthioalkyl, alkylaminoalkyl, dialkylaminoalkyl, trialkylammoniumalkyl, amino, 2(or 4)-pyridyloxy, alkoxyamino or unsaturated alkyl;

an optical isomer thereof when $R_1$ and $R_2$ are not the same;

a tautomer thereof;

or an agronomically acceptable acid addition salt thereof except when $R_3$ is a cation.

2. A compound according to claim 1 having the structure:

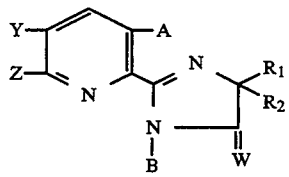

(I)

wherein A, B, W, $R_1$, $R_2$, Y and Z are as described in said claim 1.

3. A compound according to claim 2 having the structure:

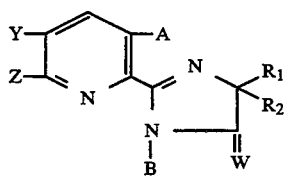

(I)

wherein A, B, W, $R_1$ and $R_2$ are as described in claim 1, one of Y and Z represents hydrogen or methyl and the other of Y and Z represents:

$C_2$–$C_6$ straight or branched alkenyl optionally substituted with phenyl, $C_1$–$C_4$ alkoxy or 1 to 3 halogens;

$C_2$–$C_6$ straight or branched alkynyl optionally substituted with phenyl, $C_1$–$C_4$ alkoxy or 1 to 3 halogens;

$C_3$–$C_6$ cycloalkyl optionally substituted with methyl, halogen or $C_1$–$C_4$ alkoxy;

$C_1$–$C_4$ alkylcarbonyl optionally substituted with $C_1$–$C_4$ alkoxy or 1 to 3 halogens;

$C_1$–$C_4$ alkylcarbonylamino optionally substituted on nitrogen with $C_1$–$C_2$ alkyl or $C_1$–$C_4$ alkoxy and on carbon with $C_1$–$C_4$ alkoxy or 1 to 3 halogens;

$C_1$–$C_4$ alkylcarbonyloxy optionally substituted with $C_1$–$C_4$ alkoxy or 1 to 3 halogens;

$C_1$–$C_4$ alkyl substituted with one or more of the following groups:

$C_1$–$C_4$ alkoxy optionally substituted with phenyl, thienyl, furyl, cyclopropyl, tetrahydrofuryl, $C_1$–$C_4$ alkoxy, $C_1$–$C_4$ dialkylamino, $C_1$–$C_4$ alkylamino, $C_1$–$C_4$ trialkylammonium, or 1 to 3 halogens; with the proviso that when the substituent on the $C_1$–$C_4$ alkoxy group is $C_1$–$C_4$ alkoxy, $C_1$–$C_4$ alkylamino, $C_1$–$C_4$ dialkylamino, or $C_1$–$C_4$ trialkylammonium, the respective heteroatoms are separated by at least 2 carbon atoms;

$C_1$–$C_4$ alkenyloxy optionally substituted with 1 to 3 halogens;

$C_1$–$C_4$ alkynyloxy optionally substituted with 1 to 3 halogens;

$C_3$–$C_6$ cycloalkoxy; phenylthio;

$C_1$–$C_4$ alkylthio optionally substituted with phenyl or 1 to 3 halogens;

$C_1$–$C_4$ alkylsulfinyl optionally substituted with phenyl or 1 to 3 halogens;

$C_1$–$C_4$ alkylsulfonyl optionally substituted with phenyl or 1 to 3 halogens;

$C_1$–$C_4$ alkylamino optionally substituted on carbon by phenyl or 1 to 3 halogens;

$C_1$–$C_4$ dialkylamino;

$C_1$–$C_4$ trialkylammonium;

$C_1$–$C_4$ alkylcarbonyloxy; cyano phenylamino, optionally substituted in the ring by 1 to 3 halogens, $C_1$–$C_4$ lower alkyl, or $C_1$–$C_4$ lower alkoxy;

phenoxy, optionally substituted in the ring by 1 to 3 halogens, $C_1$–$C_4$ lower alkyl, or $C_1$–$C_4$ lower alkoxy;

2(or 3)-furyl optionally substituted with halogen or $C_1$–$C_3$ alkyl;

2(or 3)-thienyl optionally substituted with halogen or $C_1$–$C_3$ alkyl;

N-methyl-2(or 3)-pyrrolyl; hydroxy; formyl;

amino optionally substituted with $C_1$–$C_4$ alkoxy, $C_1$–$C_4$ alkylsulfonyl, $C_1$–$C_2$ alkyl and $C_1$–$C_4$ alkoxy, $C_1$–$C_4$ alkylsulfonyl and $C_1$–$C_2$ alkyl, amino, $C_1$–$C_4$ monoalkylamino, or $C_1$–$C_4$ dialkylamino;

2(or 4)-pyridyloxy optionally substituted with $C_1$–$C_4$ alkyl, trifluoromethyl or 1 or 2 halogens;

$C_1$–$C_4$ mono or dialkylaminocarbonylamino, optionally substituted on the nitrogen attached to the ring with $C_1$–$C_2$ alkyl or $C_1$–$C_4$ alkoxy;

$C_1$–$C_4$ alkoxycarbonylamino, optionally substituted on nitrogen with $C_1$–$C_2$ alkyl or $C_1$–$C_4$ alkoxy;

$C_1$–$C_4$ mono or dialkylaminocarbonyloxy;

an N-oxide thereof when W is O, provided that $R_3$ cannot be unsaturated alkyl;

an optical isomer thereof when $R_1$ and $R_2$ are not the same;

a tautomer or a geometric isomer thereof; or an agronomically acceptable acid addition salt thereof except when $R_3$ is a salt forming cation.

4. The compound according to claim 2, 5-isopropenyl-2-(4-isopropyl-4-methyl-5-oxo-2-imidazolin-2-yl)nicotinic acid or an agronomically acceptable salt or ester thereof.

5. The compound according to claim 2, 2-(4-isopropyl-4-methyl-5-oxo-2-imidazolin-2-yl)-5-styrylnicotinic acid or an agronomically acceptable salt or ester thereof.

6. The compound according to claim 2, 2-(4-isopropyl-4-methyl-5-oxo-2-imidazolin-2-yl)-5-propenylnicotinic acid or an agronomically acceptable salt or ester thereof.

7. The compound according to claim 2, 5-acetyl-2-(4-isopropyl-4-methyl-5-oxo-2-imidazolin-2-yl)nicotinic acid or an agronomically acceptable salt or ester thereof.

8. The compound according to claim 2, 5-acetyl-2-(4-isopropyl-4-methyl-5-oxo-2-imidazolin-2-yl)-6-methyl nicotinic acid or an agronomically acceptable salt or ester thereof.

9. The compound according to claim 2, 2-(4-isopropyl-4-methyl-5-oxo-2-imidazolin-2-yl)-5-[(methylthio)methyl]nicotinic acid or an agronomically acceptable salt or ester thereof.

10. The compound according to claim 2, 6-(2-furyl)-2-(4-isopropyl-4-methyl-5-oxo-2-imidazolin-2-yl)nicotinic acid or an agronomically acceptable salt or ester thereof.

11. The compound according to claim 2, 2-(4-isopropyl-4-methyl-5-oxo-2-imidazolin-2-yl)-5-(2-thienyl)nicotinic acid or an agronomically acceptable salt or ester thereof.

12. The compound according to claim 2, 2-(4-isopropyl-4-methyl-5-oxo-2-imidazolin-2-yl)-6-(2-thienyl)nicotinic acid or an agronomically acceptable salt or ester thereof.

13. The compound according to claim 2, 2-(4-isopropyl-4-methyl-5-oxo-2-imidazolin-2-yl)-5-(3-thienyl)nicotinic acid or an agronomically acceptable salt or ester thereof.

14. The compound according to claim 2, 1,6-dihydro-2-(4-isopropyl-4-methyl-5-oxo-2-imidazolin-2-yl)-6-oxynicotinic acid or an agronomically acceptable salt or ester thereof.

15. The compound according to claim 2, 2-(4-isopropyl-4-methyl-5-oxo-2-imidazolin-2-yl)-6-[(methylthio)methyl]nicotinic acid or an agronomically acceptable salt or ester thereof.

16. The compound according to claim 2, isopropylammonium 6-(2-furyl)-2-(4-isopropyl-4-methyl-5-oxo-2-imidazolin-2-yl)nicotinate.

17. A method for the control of undesirable plant species comprising: applying to the foliage of said plants or to soil or water containing seeds or other propagating organs thereof, a herbicidally effective amount of a compound having the structure:

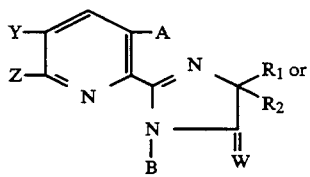

I.

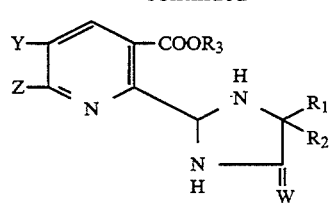

II.

wherein
$R_1$ is $C_1$–$C_4$ alkyl;
$R_2$ is $C_1$–$C_4$ alkyl or $C_3$–$C_6$ cycloalkyl; and when $R_1$ and $R_2$ are taken together with the carbon to which they are attached they may represent $C_3$–$C_6$ cycloalkyl optionally substituted with methyl;
A is $COOR_3$, $CONHR_6$, CHO, $CH_2OH$, $COCH_3$, $COC_6H_5$, CN, $CH_3$, $CH=NOH$, $CH_2COOH$, CONHOH, $CH_2CH_2COOH$, $CHR_8OH$,

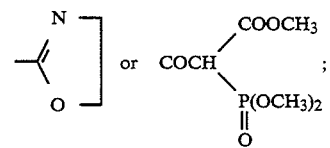

$R_3$ is hydrogen,

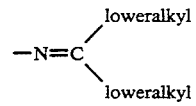

$C_1$–$C_{12}$ alkyl optionally substituted with one of the following groups: $C_1$–$C_3$ alkoxy, $C_1$–$C_3$ alkylthio, halogen, hydroxyl, $C_3$–$C_6$ cycloalkyl, benzyloxy, furyl, phenyl, halophenyl, loweralkylphenyl, loweralkoxyphenyl, nitrophenyl, carboxyl, loweralkoxycarbonyl, cyano or triloweralkylammonium halide;
$C_3$–$C_{12}$ alkenyl optionally substituted with one of the following groups: $C_1$–$C_3$ alkoxy, phenyl, halogen or loweralkoxycarbonyl or with two $C_1$–$C_3$ alkoxy groups or two halogen groups;
$C_3$–$C_6$ cycloalkyl optionally substituted with one or two $C_1$–$C_3$ alkyl groups;
$C_3$–$C_{16}$ alkynyl optionally substituted with one or two $C_1$–$C_3$ alkyl groups; or a cation;
$R_6$ is hydrogen, hydroxyl, $C_3$-alkenyl, $C_3$-alkynyl or $C_1$–$C_4$ alkyl optionally substituted with one hydroxyl or one chlorine group;
B is H, $COR_4$ or $SO_2R_5$;
$R_4$ is $C_1$–$C_{11}$ alkyl, chloromethyl or phenyl optionally substituted with one chloro, one nitro or one methoxy group;
$R_5$ is $C_1$–$C_4$ alkyl or phenyl optionally substituted with one methyl group;
W is O or S;
$R_8$ is $C_1$–$C_4$ alkyl or phenyl;
Y and Z may independently be selected from the group consisting of hydrogen, halogen, $C_1$–$C_6$ alkyl, $C_1$–$C_4$ hydroxyalkyl, $C_1$–$C_6$ alkoxy, $C_1$–$C_4$ alkylthio, phenoxy, $C_1$–$C_4$ haloalkyl, nitro, cyano, $C_1$–$C_4$ alkylamino, di-$C_1$–$C_4$ alkylamino, $C_1$–$C_4$ alkylsulfonyl, difluoromethoxy, trifluoromethoxy, 1,1,2,2,-tetrafluoroethoxy, phenyl optionally substituted with one $C_1$-$C_4$ alkyl, $C_1$-$C_4$ alkoxy or halogen;

$C_3$-$C_8$ straight or branched alkenyloxy optionally substituted with 1 to 3 halogens;

$C_3$-$C_8$ straight or branched alkynyloxy optionally substituted with 1 to 3 halogens;

$C_2$-$C_6$ straight or branched alkynyl substituted with hydroxy;

$C_3$-$C_6$ cycloalkyl interrupted by 1 oxygen, sulfur, amino or $C_1$-$C_4$ alkylamino; and oxiranyl optionally substituted by one or two $C_1$-$C_4$ alkyl;

And at least one member of Y and Z must be selected from the group consisting of:

$C_2$-$C_6$ straight or branched alkenyl optionally substituted with phenyl, $C_1$-$C_4$ alkoxy or 1 to 3 halogens;

$C_2$-$C_6$ straight or branched alkynyl optionally substituted with phenyl, $C_1$-$C_4$ alkoxy or 1 to 3 halogens;

$C_3$-$C_6$ cycloalkyl optionally substituted with methyl, halogen or $C_1$-$C_4$ alkoxy;

$C_1$-$C_4$ alkylcarbonyl optionally substituted with $C_1$-$C_4$ alkoxy or 1 to 3 halogens;

$C_1$-$C_4$ alkylcarbonylamino optionally substituted on nitrogen with $C_1$-$C_2$ alkyl or $C_1$-$C_4$ alkoxy and on carbon with $C_1$-$C_4$ alkoxy or 1 to 3 halogens;

$C_1$-$C_4$ alkylcarbonyloxy optionally substituted with $C_1$-$C_4$ alkoxy or 1 to 3 halogens;

$C_1$-$C_4$ alkyl substituted with one or more of the following groups: $C_1$-$C_4$ alkoxy optionally substituted with phenyl, thienyl, furyl, cyclopropyl, tetrahydrofuryl, $C_1$-$C_4$ alkoxy, $C_1$-$C_4$ dialkylamino, $C_1$-$C_4$ alkylamino, $C_1$-$C_4$ trialkylammonium or 1 to 3 halogens; with the proviso that when the substituent on the $C_1$-$C_4$ alkoxy group is $C_1$-$C_4$ alkoxy, $C_1$-$C_4$ alkylamino, $C_1$-$C_4$ dialkylamino or $C_1$-$C_4$ trialkylammonium, the respective heteroatoms are separated by at least 2 carbon atoms;

$C_1$-$C_4$ alkenyloxy optionally substituted with 1 to 3 halogens;

$C_1$-$C_4$ alkynyloxy optionally substituted with 1 to 3 halogens;

$C_3$-$C_6$ cycloalkoxy;

$C_3$-$C_6$ cycloalkoxy; phenylthio;

$C_1$-$C_4$ alkylthio optionally substituted with phenyl or 1 to 3 halogens;

$C_1$-$C_4$ alkylsulfinyl optionally substituted with phenyl or 1 to 3 halogens;

$C_1$-$C_4$ alkylsulfonyl optionally substituted with phenyl or 1 to 3 halogens;

$C_1$-$C_4$ alkylamino optionally substituted on carbon by phenyl or 1 to 3 halogens;

$C_1$-$C_4$ dialkylamino;

$C_1$-$C_4$ trialkylammonium;

$C_1$-$C_4$ alkylcarbonyloxy; cyano;

phenylamino, optionally substituted in the ring by 1 to 3 halogens, $C_1$-$C_4$ alkyl, or $C_1$-$C_4$ alkoxy;

phenoxy, optionally substituted in the ring by 1 to 3 halogens, $C_1$-$C_4$ alkyl, or $C_1$-$C_4$ alkoxy;

2(or 3)-furyl optionally substituted with halogen or $C_1$-$C_3$ alkyl;

2(or 3)-thienyl optionally substituted with halogen or $C_1$-$C_3$ alkyl;

N-methyl-2(or 3)-pyrrolyl; hydroxy; formyl;

amino optionally substituted with $C_1$-$C_4$ alkoxy, $C_1$-$C_4$ alkylsulfonyl, $C_1$-$C_2$ alkyl and $C_1$-$C_4$ alkoxy, $C_1$-$C_4$ alkylsulfonyl and $C_1$-$C_2$ alkyl, amino, $C_1$-$C_4$ monoalkylamino, or $C_1$-$C_4$ dialkylamino;

2(or 4)-pyridyloxy optionally substituted with $C_1$-$C_4$ alkyl, trifluoromethyl or 1 or 2 halogens;

$C_1$-$C_4$ mono or dialkylaminocarbonylamino, optionally substituted on the nitrogen attached to the ring with $C_1$-$C_2$ alkyl or $C_1$-$C_4$ alkoxy;

$C_1$-$C_4$ alkoxycarbonylamino, optionally substituted on nitrogen with $C_1$-$C_2$ alkyl or $C_1$-$C_4$ alkoxy; and $C_1$-$C_4$ mono or dialkylaminocarbonyloxy;

Provided that when Y is hydroxy, Z cannot be hydrogen;

Provided also that when B is $COR_4$ or $SO_2R_5$, A is $CH_3$, CN or $COOR_3$ in which $R_3$ is other than H or a cation and W is O, then Y and Z cannot be alkylamino, hydroxyl or hydroxyloweralkyl;

an N-oxide thereof when W is O, provided that $R_3$ cannot be unsaturated alkyl and Y and Z cannot be alkylthioalkyl, alkylaminoalkyl, dialkylaminoalkyl, trialkylammoniumalkyl, amino, 2(or 4)-pyridyloxy, alkoxyamino or unsaturated alkyl;

an optical isomer thereof when $R_1$ and $R_2$ are not the same;

a tautomer thereof;

or an agronomically acceptable acid addition salt thereof except when $R_3$ is a cation.

18. The method according to claim 17 for controlling undesirable plant species comprising: applying to the foliage of said plants or to soil or water containing seeds or other propagating organs thereof, a herbicidally effective amount of a compound having the structure:

(I)

wherein A, B, W, $R_1$ and $R_2$ are as described in claim 1, one of Y and Z represents hydrogen or methyl and the other of Y and Z represents:

$C_2$-$C_6$ straight or branched alkenyl optionally substituted with phenyl, $C_1$-$C_4$ alkoxy or 1 to 3 halogens;

$C_2$-$C_6$ straight or branched alkynyl optionally substituted with phenyl, $C_1$-$C_4$ alkoxy or 1 to 3 halogens;

$C_3$-$C_6$ cycloalkyl optionally substituted with methyl, halogen or $C_1$-$C_4$ alkoxy;

$C_1$-$C_4$ alkylcarbonyl optionally substituted with $C_1$-$C_4$ alkoxy or 1 to 3 halogens;

$C_1$-$C_4$ alkylcarbonylamino optionally substituted on nitrogen with $C_1$-$C_2$ alkyl or $C_1$-$C_4$ alkoxy and on carbon iwth $C_1$-$C_4$ alkoxy or 1 to 3 halogens;

$C_1$-$C_4$ alkylcarbonyloxy optionally substituted with $C_1$-$C_4$ alkoxy or 1 to 3 halogens;

$C_1$-$C_4$ alkyl substituted with one or more of the following groups:

$C_1$-$C_4$ alkoxy optionally substituted with phenyl, thienyl, furyl, cyclopropyl, tetrahydrofuryl, $C_1$-$C_4$ alkoxy, $C_1$-$C_4$ dialkylamino, $C_1$-$C_4$ alkylamino, $C_1$-$C_4$ trialkylammonium, or 1 to 3 halogens; with the proviso that when the substituent on the $C_1$-$C_4$ alkoxy group is $C_1$-$C_4$ alkoxy, $C_1$-$C_4$ alkylamino, $C_1$-$C_4$ dialkylamino, or $C_1$-$C_4$ trialkylammonium, the respective heteroatoms are separated by at least 2 carbon atoms;

$C_1$-$C_4$ alkenyloxy optionally substituted with 1 to 3 halogens;

$C_1$-$C_4$ alkynyloxy optionally substituted with 1 to 3 halogens;

$C_3-C_6$ cycloalkoxy; phenylthio;

$C_1-C_4$ alkylthio optionally substituted with phenyl or 1 to 3 halogens;

$C_1-C_4$ alkylsulfinyl optionally substituted with phenyl or 1 to 3 halogens;

$C_1-C_4$ alkylsulfonyl optionally substituted with phenyl or 1 to 3 halogens;

$C_1-C_4$ alkylamino optionally substituted on carbon by phenyl or 1 to 3 halogens;

$C_1-C_4$ dialkylamino;

$C_1-C_4$ trialkylammonium;

$C_1-C_4$ alkylcarbonyloxy; cyano;

phenylamino, optionally substituted in the ring by 1 to 3 halogens, $C_1-C_4$ lower alkyl, or $C_1-C_4$ lower alkoxy;

phenoxy, optionally substituted in the ring by 1 to 3 halogens, $C_1-C_4$ lower alkyl, or $C_1-C_4$ lower alkoxy;

2(or 3)-furyl optionally substituted with halogen or $C_1-C_3$ alkyl;

2(or 3)-thienyl optionally substituted with halogen or $C_1-C_3$ alkyl;

N-methyl-2(or 3)-pyrrolyl; hydroxy; formyl;

amino optionally substituted with $C_1-C_4$ alkoxy, $C_1-C_4$ alkylsulfonyl, $C_1-C_2$ alkyl and $C_1-C_4$ alkoxy, $C_1-C_4$ alkylsulfonyl and $C_1-C_2$ alkyl, amino, $C_1-C_4$ monoalkylamino, or $C_1-C_4$ dialkylamino;

2(or 4)-pyridyloxy optionally substituted with $C_1-C_4$ alkyl, trifluoromethyl or 1 or 2 halogens;

$C_1-C_4$ mono or dialkylaminocarbonylamino, optionally substituted on the nitrogen attached to the ring with $C_1-C_2$ alkyl or $C_1-C_4$ alkoxy;

$C_1-C_4$ alkoxycarbonylamino, optionally substituted on nitrogen with $C_1-C_2$ alkyl or $C_1-C_4$ alkoxy;

$C_1-C_4$ mono or dialkylaminocarbonyloxy;

an N-oxide thereof when W is O, provided that $R_3$ cannot be unsaturated alkyl;

an optical isomer thereof when $R_1$ and $R_2$ are not the same;

a tautomer or a geometric isomer thereof; or an agronomically acceptable acid addition salt thereof except when $R_3$ is a salt forming cation.

19. The compound according to claim 2, 2-(4-isopropyl-4-methyl-5-oxo-2-imidazolin-2-yl)-5-(methoxymethyl)nicotinic acid or an agronomically acceptable salt or ester thereof.

20. The compound according to claim 2, 5-(ethoxymethyl)-2-(4-isopropyl-4-methyl-5-oxo-2-imidazolin-2-yl)nicotinic acid or an agronomically acceptable salt or ester thereof.

21. The compound according to claim 2, 5-(dimethoxymethyl)-2-(4-isopropyl-4-methyl-5-oxo-2-imidazolin-2-yl)nicotinic acid or an agronomically acceptable salt or ester thereof.

22. The compound according to claim 2, 5-(n-propoxymethyl)-2-(4-isopropyl-4-methyl-5-oxo-2-imidazolin-2-yl)nicotinic acid or an agronomically acceptable salt or ester thereof.

23. The compound according to claim 2, 5-(sec-butoxymethyl)-2-(4-isopropyl-4-methyl-5-oxo-2-imidazolin-2-yl)nicotinic acid or an agronomically acceptable salt or ester thereof.

24. The compound according to claim 2, 5-[(2-methoxyethoxy)methyl]-2-(4-isopropyl-4-methyl-5-oxo-2-imidazolin-2-yl)nicotinic acid or an agronomically acceptable salt or ester thereof.

25. The compound according to claim 2, 5-[(2,2,2-trifluoroethoxy)methyl]-2-(4-isopropyl-4-methyl-5-oxo-2-imidazolin-2-yl)nicotinic acid or an agronomically acceptable salt or ester thereof.

26. The compound according to claim 2, 5-(n-butoxymethyl)-2-(4-isopropyl-4-methyl-5-oxo-2-imidazolin-2-yl)nicotinic acid or an agronomically acceptable salt or ester thereof.

27. The compound according to claim 2, 5-(isopropoxymethyl)-2-(4-isopropyl-4-methyl-5-oxo-2-imidazolin-2-yl)nicotinic acid or an agronomically acceptable salt or ester thereof.

28. The compound according to claim 2, 5-[(2-fluoroethoxy)methyl]-2-(4-isopropyl-4-methyl-5-oxo-2-imidazolin-2-yl)nicotinic acid or an agronomically acceptable salt or ester thereof.

29. The compound according to claim 2, 5-[(2,2,2-trichloroethoxy)methyl]-2-(4-isopropyl-4-methyl-5-oxo-2-imidazolin-2-yl)nicotinic acid or an agronomically acceptable salt or ester thereof.

30. The compound according to claim 2, 5-(isobutoxymethyl)-2-(4-isopropyl-4-methyl-5-oxo-2-imidazolin-2-yl)nicotinic acid or an agronomically acceptable salt or ester thereof.

* * * * *